(12) United States Patent
Ogembo et al.

(10) Patent No.: US 12,012,446 B2
(45) Date of Patent: Jun. 18, 2024

(54) EPSTEIN-BARR VIRUS ANTIBODIES AND USES THEREOF

(71) Applicant: CITY OF HOPE, Duarte, CA (US)

(72) Inventors: Javier Gordon Ogembo, San Dimas, CA (US); Lorraine Zvichapera Mutsvunguma, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 17/807,363

(22) Filed: Jun. 16, 2022

(65) Prior Publication Data

US 2023/0056712 A1 Feb. 23, 2023

Related U.S. Application Data

(63) Continuation of application No. 16/940,304, filed on Jul. 27, 2020, now abandoned, which is a continuation-in-part of application No. 16/609,078, filed as application No. PCT/US2018/030030 on Apr. 27, 2018, now Pat. No. 11,401,323.

(60) Provisional application No. 62/880,024, filed on Jul. 29, 2019, provisional application No. 62/491,945, filed on Apr. 28, 2017.

(51) Int. Cl.
C07K 16/08 (2006.01)
A61K 39/00 (2006.01)

(52) U.S. Cl.
CPC ...... *C07K 16/085* (2013.01); *A61K 2039/505* (2013.01); *C07K 2317/24* (2013.01); *C07K 2317/565* (2013.01)

(58) Field of Classification Search
CPC .............. C07K 16/085; C07K 2317/24; C07K 2317/34; C07K 2317/76; A61K 35/763; A61K 38/162; A61K 39/245; A61K 47/65; A61K 47/6811; A61K 47/6839; A61K 39/42; A61K 47/6803; A61K 2039/505; C12N 2710/16222
See application file for complete search history.

(56) References Cited

U.S. PATENT DOCUMENTS

| 4,707,358 A | * | 11/1987 | Kieff | C07K 14/005 |
| | | | | 514/3.7 |
| 2015/0064174 A1 | | 3/2015 | Wang et al. | |
| 2016/0303224 A1 | * | 10/2016 | Kanekiyo | C07K 16/085 |

FOREIGN PATENT DOCUMENTS

WO 2018/200742 A1 11/2018

OTHER PUBLICATIONS

Tanner JE, Coinçon M, et al. Peptides designed to spatially depict the Epstein-Barr virus major virion glycoprotein gp350 neutralization epitope elicit antibodies that block virus-neutralizing antibody 72A1 interaction with the native gp350 molecule. J Virol. May 2015;89(9):4932-41. Epub Feb. 18, 2015. (Year: 2015).*
Alfarano, C., et al., "The biomolecular interaction network database and related tools 2005 update," Nucleic Acids Res. 33:D418-D424 (2005).
Babcock, G. J., et al., "EBV persistence in memory B cells in vivo," Immunity 9:395-404 (1998).
Baghian, A., et al., "Glycoprotein B of human herpesvirus 8 is a component of the virion in a cleaved form composed of amino- and carboxyl-terminal fragments," Virol. 269:18-25 (2000).
Balfour, H. H., et al., "Progress, prospects, and problems in Epstein-barr virus vaccine development," Curr. Opin. Virol. 0:1-5 (2014).
Benkerrou, M., et al., "Anti-B-cell monoclonal antibody treatment of severe posttransplant B-lymphoproliferative disorder: Prognostic factors and long-term outcome," Blood 92(9):3137-3147 (1998).
Biggar, R. J., et al., "Primary Epstein-Barr virus infections in African infants. I. Decline of Maternal antibodies and time of infection," Int. J. Cancer 22:239-243 (1978).
Biggar, R. J., et al., "Primary Epstein-Barr virus infections in African Infants. II. Clinical and Serological Observations during seroconversion," Int. J. Cancer 22: 244-250 (1978).
Bowie, J. U., et al., "Deciphering the Message in Protein Sequences: Tolerance to Amino Acid Substitutions," Science 247:1306-1310 (1990).
Brochet, X., et al., "IMGT/V-QUEST: the highly customized and integrated system for IG and TR standardized V-J and V-D-J sequence analysis," Nucleic Acids Res. 36:W503-W508 (2008).
Broering, T. J., et al., "Identification and characterization of broadly neutralizing human monoclonal antibodies directed against the E2 envelope glycoprotein of Hepatitis C virus," J. Virol. 83(23):12473-12482 (2009).
Bu, W., et al., "Immunization with components of the viral fusion apparatus elicits antibodies that neutralize Epstein-Barr virus in B cells and epithelial cells," Immunity 50(5):1305-1316 (2019).
Chen, J., et al., "Ephrin receptor A2 is a functional entry receptor for Epstein-barr virus," Nat. Microbiol. 3(2):172-180 (2018).
Chen, Z., et al., "Human monoclonal antibodies targeting the haemagglutinin glycoprotein can neutralize H7N9 influenza virus," Nat. Commun. 6:6714 (2015).
Chesnokova, L. S., et al., "Fusion of epithelial cells by Epstein-barr virus proteins is triggered by binding of viral glycoproteins gHgL to integrins αvβ6 or αvβ8," Proc. Natl. Acad. Sci. USA 106(48):20464-20469 (2009).

(Continued)

*Primary Examiner* — Rachel B Gill
(74) *Attorney, Agent, or Firm* — Perkins Coie LLP; Lara J. Dueppen; Gregory J. Logan

(57) ABSTRACT

Disclosed herein are antibodies or immunogenic fragments thereof that specifically bind to Epstein-Barr virus (EBV) glycoprotein 350 (gp350) or 220 or one or more immunogenic peptides. Also disclosed are immunogenic peptides comprising fragments of gp350 amino acid sequence, EBV antibody-small molecule conjugates and pharmaceutical compositions comprising the antibody or an immunogenic fragment thereof, one or more immunogenic peptides, or the EBV antibody-small molecule conjugate. The antibodies, immunogenic peptides, conjugates, and pharmaceutical compositions can be used to treat or prevent EBV infections and EBV-associated conditions and diseases.

21 Claims, 34 Drawing Sheets

Specification includes a Sequence Listing.

(56) References Cited

OTHER PUBLICATIONS

Chiuppesi, F., et al., "Vaccine-derived neutralizing antibodies to the human cytomegalovirus gH/gL pentamer potently block primary cytotrophoblast infection," J. Virol. 89(23):11884-11898 (2015).
Cohen, J. I., "Epstein-barr virus infection," New Engl. J. Med. 343(7):481-492 (2000).
Cohen, J. I., et al., "Epstein-barr virus: an important vaccine target for cancer prevention," Sci. Transl. Med. 3(107):107fs7 (2011).
Cohen, J. I., et al., "Epstein-barr virus vaccines," Clin. Transl. Immunol. 4:e32 (2015).
Collis, A. V. J., et al., "Analysis of the antigen combining site: Correlations between length and sequence composition of the hypervariable loops and the nature of the antigen," J. Mol. Biol. 325:337-354 (2003).
Connolly, S. A., et al., "Fusing structure and function: a structural view of the herpesvirus entry machinery," Nat. Rev. Microbiol. 9(5):369-381 (2011).
Cote, T. R., et al., "Non-Hodgkin's lymphoma among people with AIDS: Incidence, presentation and public health burden," Int. J. Cancer 73:645-650 (1997).
Cruz, R. J., et al., "Surgical management of gastrointestinal post-transplant lymphoproliferative disorders in liver transplant recipients," Transplantation 94:417-423 (2012).
Cui, X., et al., "Rabbits immunized with Epstein-Barr virus gH/gL or GB recombinant proteins elicit higher serum virus neutralizing activity than gp350," Vaccine 34:4050-4055 (2016).
Donaldson, J. M., et al., "Identification and grafting of a unique peptide-binding site in the Fab framework of monoclonal antibodies," Proc. Natl. Acad. Sci. USA 110(43):17456-17461 (2013).
Dondelinger, M., et al., "Understanding the significance and implications of antibody numbering and antigen-binding surface/residue definition," Front. Immunol. 9(2278):1-15 (2018).
Dubowchik, G. M., et al., "Cathepsin B-sensitive dipeptide prodrugs. 1. A model study of structural requirements for efficient release of doxorubicin," Bioorg. Med. Chem. Ltr. 8:3341-3346 (1998).
Dzeng, R. K., et al., "Small molecule growth inhibitors of human oncogenic gammaherpesvirus infected B-cells," Mol. Oncol. 9:365-376 (2015).
Eisenberg, R. J., et al., "Herpes virus fusion and entry: a story with many characters," Viruses 4:800-832 (2012).
Faro, A., et al., "Interferon-alpha affects the immune response in post-transplant lymphoproliferative disorder," Am. J. Respir. Crit. Care Med. 153:1442-1447 (1996).
Ferrara, N., et al., "Discovery and development of Bevacizumab, an anti-VEGF antibody for treating cancer," Nat. Rev. Drug Discov. 3:391-400 (2004).
Finerty, S., et al., "Immunization of cottontop tamarins and rabbits with a candidate vaccine against the Epstein-Barr virus based on the major viral envelope glycoprotein gp340 and alum," Vaccine 12(13):1180-1184 (1994).
Fingeroth, J. D., et al., "Epstein-barr virus receptor of human B lymphocytes is the C3d receptor CR2," Proc. Natl. Acad. Sci. USA 81:4510-4514 (1984).
Glotz, D., et al., "The Seville expert workshop for progress in posttransplant lymphoproliferative disorders," Transplantation 94:784-793 (2012).
Goedert, J. J., et al., "Spectrum of AIDS-associated malignant disorders," Lancet 351:1833-1839 (1998).
Gu, S. Y., et al., "First EBV vaccine trial in humans using recombinant vaccinia virus expressing the major membrane antigen," Dev. Biol. Stand. 84:171-177 (1995).
Han, T., et al., "Structural basis of influenza virus neutralization," Ann. N.Y. Acad. Sci. 1217:178-190 (2011).
Haque, T., et al., "A mouse monoclonal antibody against Epstein-barr virus envelope glycoprotein 350 prevents infection both in vitro and in vivo," J. Infect. Dis. 194:584-587 (2006).
Henle, G., et al., "Relation of Burkitt's tumor-associated herpes-type virus to infectious mononucleosis," Microbiol. 59:94-101 (1968).
Henle, G., et al., "The virus as the etiologic agent of infectious mononucleosis," The Epstein-Barr Virus (1979) pp. 297-320.
Herrman, M., et al., "Epstein-barr virus gp350 can functionally replace the rhesus lymphocryptovirus major membrane glycoprotein and does not restrict infection of rhesus macaques," J. Virol. 90(3):1222-1230 (2016).
Hoffman, G. J., et al., "Monoclonal antibody against a 250,000-dalton glycoprotein of Epstein-barr virus identifies a membrane antigen and a neutralizing antigen," Proc. Natl. Acad. Sci. USA 77(5):2979-2983 (1980).
Hudis, C. A., "Trastuzumab—Mechanism of action and use in clinical practice," New Engl. J. Med. 357:39-51 (2007).
Jangalwe, S., et al., "Improved B cell development in humanized NOD-scid IL2R$\gamma^{null}$ mice transgenically expressing human stem cell factor, granulocyte-macrophage colony-stimulating factor and interleukin-3," Immunity, Inflammation and Disease 4(4):427-440 (2016).
Jiang, L., et al., "EBNA1-targeted probe for the imaging and growth inhibition of tumours associated with the Epstein-Barr virus," Nat. Biomed. Engineering 1:0042 (2017).
Jones, S. T., et al., "Rapid PCR-Cloning of Full-Length Mouse Immunoglobulin Variable Regions," Biotechnology 9:579 (1991).
Jonker, D. J., et al., "Cetuximab for the Treatment of Colorectal Cancer," New Engl. J. Med. 357:2040-2048 (2007).
Kanekiyo, M., et al., "Rational design of an Epstein-Barr virus vaccine targeting the receptor-binding site," Cell 162:1090-1100 (2015).
Khanna, R., et al., "EBV structural antigens, gp350 and gp85, as targets for ex vivo virus-specific CTL during acute infectious mononucleosis: Potential use of gp350/gp85 CTL epitopes for vaccine design," J. Immunol. 162:3063-3069 (1999).
Khyatti, M., et al., "Epstein-barr virus (EBV) glycoprotein gp350 expressed on transfected cells resistant to natural killer cell activity serves as a target antigen for EBV-specific antibody-dependent cellular cytotoxicity," J. Virol. 65(2):996-1001 (1991).
Kussie, P. H., et al., "A single engineered amino acid substitution changes antibody fine specificity," J. Immunol. 152:146-152 (1994).
Luzuriaga, K., et al., "Infectious mononucleosis," New Engl. J. Med. 362:1993-2000 (2010).
Milpied, N., et al., "Humanized anti-CD20 monoclonal antibody (Rituximab) in post transplant B-lymphoproliferative disorder: a retrospective analysis on 32 patients," Annals of Oncology 11(Suppl. 1): S113-S116 (2000).
Mok, H., et al., "Evaluation of measles vaccine virus as a vector to deliver respiratory syncytial virus fusion protein or Epstein-barr virus glycoprotein gp350," Open Virol. J. 6:12-22 (2012).
Mold, C., et al., "Activation of the alternative complement pathway by EBV and the viral envelope glycoprotein, gp350," J. Immunol. 140:3867-3874 (1988).
Moutschen, M., et al., "Phase I/II studies to evaluate safety and immunogenicity of a recombinant gp350 Epstein-Barr virus vaccine in healthy adults," Vaccine 25:4697-4705 (2007).
Mulama, D. H., et al., "A multivalent Kaposi sarcoma-associated herpesvirus-like particle vaccine capable of eliciting high titers of neutralizing antibodies in immunized rabbits," Vaccine 37(30):4184-4194 (2019).
Mutsvunguma, L. Z., et al., "Identification of multiple potent neutralizing and non-neutralizing antibodies against Epstein-Barr virus gp350 protein with potential for clinical application and as reagents for mapping immunodominant epitopes," Virol. 536:1-15 (2019).
Nemerow, G. R., et al., "Identification of gp350 as the viral glycoprotein mediating attachment of Epstein-barr virus (EBV) to the EBV/C3d receptor of B cells: Sequence homology of gp350 and C3 complement fragment C3d," J. Virol. 61(5):1416-1420 (1987).
Nemerow, G. R., et al., "Identification of an epitope in the major envelope protein of Epstein-Barr virus that mediates viral binding to the B lymphocyte EBV receptor (CR2)," Cell 56:369-377 (1989).
Ogembo, J. G., et al., "Human complement receptor type 1/CD35 is an Epstein-barr virus receptor," Cell Rep. 3(2):371-385 (2013).

(56) References Cited

OTHER PUBLICATIONS

Ogembo, J. G., et al., "A chimeric EBV gp350/220-based VLP replicates the virion B-cell attachment mechanism and elicits long-lasting neutralizing antibodies in mice," J. Transl. Med. 13:50 (2015).

Papadopoulos, E. B., et al., "Infusions of donor leukocytes to treat Epstein-barr virus-associated lymphoproliferative disorders after allogenic bone marrow transplantation," N. Engl. J. Med. 330(17):1185-1191 (1994).

Pei, J., et al., "PROMALS3D: a tool for multiple protein sequence and structure alignments," Nucleic Acids Res. 36(7):2295-2300 (2008).

Perez, E. M., et al., "Novel Epstein-barr virus-like particles incorporating gH/gL-EBNA1 or GB-LMP2 induce high neutralizing antibody titers and EBV-specific T-cell responses in immunized mice," Oncotarget 8(12):19255-19273 (2017).

Piedimonte, G., et al., "A humanized monoclonal antibody against respiratory syncytial virus (Palivizumab) inhibits RSV-induced neurogenic-mediated inflammation in rat airways," Pediat. Res. 47(3):351-356 (2000).

Qualtiere, L. F., et al., "Epitope mapping of the major Epstein-barr virus outer envelope glycoprotein gp350/220," J. Gen. Virol. 68:535-543 (1987).

Rees, L., et al., "A phase I trial of Epstein-barr virus Gp350 vaccine for children with chronic kidney disease awaiting transplantation," Transplant. 88:1025-1029 (2009).

Rickinson, A. B., "Epstein-Barr Virus," Fields Virology, 5th Ed., Lippincott Williams & Wilkins, 78 pages (2007).

Sashihara, J., et al., "Human antibody titers to Epstein-barr virus (EBV) gp350 correlate with neutralization of infectivity better than antibody titers to EBV gp42 using a rapid flow cytometry-based EBV neutralization assay," Virol. 391(2):249-256 (2009).

Sela, M., et al., "Antibodies to sequential and conformational determinants," Cold Spring Harbor Symposia on Quantitative Biology 32:537-545 (1967).

Sela-Culang, I., et al., "The structural basis of antibody-antigen recognition," Front. Immunol. 4(302):1-13 (2013).

Senter, P. D., et al., "The discovery and development of brentuximab vedotin for use in relapsed Hodgkin lymphoma and systemic anaplastic large cell lymphoma," Nat. Biotechnol. 30(7):631-637 (2012).

Sirin, S., et al., "AB-Bind: Antibody binding mutational database for computational affinity predictions," Protein Sci. 25:393-409 (2016).

Sitompul, L. S., et al., "Epitope mapping of gp350/220 conserved domain of epstein barr virus to develop nasopharyngeal carcinoma (npc) vaccine," Bioinformation 8(10):479-482 (2012).

Sokal, E. M., et al., "Recombinant gp350 vaccine for infectious mononucleosis: a phase 2, randomized, double-blind, placebo-controlled trial to evaluate the safety, immunogenicity, and efficacy of an Epstein-barr virus vaccine in healthy young adults," J. Infect. Dis. 196:1749-1753 (2007).

Speck, P., et al., "Epstein-Barr virus (EBV) infection visualized by EGFP expression demonstrates dependence on known mediators of EBV entry," Arch. Virol. 144:1123-1137 (1999).

Stamatatos, L., et al., "Neutralizing antibodies generated during natural HIV-1 infection: Good news for an HIV-1 vaccine?" Nat. Med. 15(8):866-870 (2009).

Sui, J., et al., "Structural and functional bases for broad-spectrum neutralization of avian and human influenza A viruses," Nat. Struct. Mol. Biol. 16(3):265-273 (2009).

Szakonyi, G., et al., "Structure of the Epstein-Barr virus major envelope glycoprotein," Nat. Struct. Mol. Biol. 13(11):996-1001 (2006).

Tanner, J., et al., "Epstein-Barr virus gp350/220 binding to the B lymphocyte C3d receptor mediates adsorption, capping, and endocytosis," Cell 50:203-213 (1987).

Tanner, J., et al., "Soluble gp350/220 and deletion mutant glycoproteins block Epstein-barr virus adsorption to lymphocytes," J. Virol. 62(12):4452-4464 (1988).

Tanner, J. E., et al., "Peptides designed to spatially depict the Epstein-barr virus major virion glycoprotein gp350 neutralization epitope elicit antibodies that block virus-neutralizing antibody 72A1 interaction with the native gp350 molecule," J. Virol. 89:4932-4941 (2015).

Tanner, J. E., et al., "Construction and characterization of a humanized anti-Epstein-barr virus gp350 antibody with neutralizing activity in cell culture," Cancers 10:112 (2018).

Thorley-Lawson, D. A., et al., "Monoclonal antibodies against the major glycoprotein (gp350/220) of Epstein-barr virus neutralize infectivity," Proc. Natl. Acad. Sci. USA 77(9):5307-5311 (1980).

Thorley-Lawson, D. A., et al., "Identification and isolation of the main component (gp350-gp220) of Epstein-barr virus responsible for generating neutralizing antibodies in vivo," J. Virol. 43(2):730-736 (1982).

Tsuchiya, Y., et al., "The diversity of H3 loops determines the antigen-binding tendencies of antibody CDR loops," Protein Sci. 25:815-825 (2016).

Tugizov, S. M., et al., "Epstein-Barr virus infection of polarized tongue and nasopharyngeal epithelial cells," Nat. Med. 9(3):307-314 (2003).

United States Patent and Trademark Office, International Search Report and Written Opinion dated Aug. 7, 2018 for PCT/US18/30030.

Urquiza, M., et al., "Identification of three gp350/220 regions involved in Epstein-barr virus invasion of host cells," J. Biol. Chem. 280(42):35598-35605 (2005).

Walker, L. M., et al., "Broad and potent neutralizing antibodies from an African donor reveal a new HIV-1 vaccine target," Science 326(5950):285-289 (2009).

Weiss, E. R., et al., "High Epstein-barr virus load and genomic diversity are associated with generation of gp350-specific neutralizing antibodies following acute infectious mononucleosis," J. Virol. 91(1):e01562-16 (2016).

Winkler, K., et al., "Changing the antigen binding specificity by single point mutations of an anti-p24 (HIV-1) antibody," J. Immunol. 165:4505-4514 (2000).

Wrammert, J., et al., "Rapid cloning of high affinity human monoclonal antibodies against influenza virus," Nature 453(7195):667-671 (2008).

Zhang, P.F., et al., "Mapping of the epitopes of Epstein-barr virus gp350 using monoclonal antibodies and recombinant proteins expressed in *Escherichia coli* defines three antigenic determinants," J. Gen. Virol. 72:2747-2755 (1991).

Zhang, H., et al., "Ephrin receptor A2 is an epithelial cell receptor for Epstein-Barr virus entry," Nat. Microbiol. 3:164-171 (2018).

\* cited by examiner

FIG. 3A

```
                   FR-1                                    FR-2                                              FR-3
              95 96  6   69 6 9   55 5             9565 75 757 5 9   5 95       7 6            77  7 6 66      77
Conservation:
72A1        1 --PELVKPGTSMKISCKAS SSSFTDY TMNWMKQSHGKNLRWIGI KPYNKP RYNQKFKGKATLTLDKSSTAYMEVTLSL  78
HB1         1 --PGLVAPSQSLSITCTVSG FLITTY SVHWVRQPPGKGLEWLGV WAGG-S MYNSAALMSRLS INKDISKSQVFLKMNSL  77
HB2         1 --PELKKPGETVKISCKASG YTFTAV SMHWVKLFPGKGLKWMCM INTKTGEF TYADDFKGRFAFSLETSASTAYLQINNL      78
HB3         1 --AELVRPGASVKLSCKAPG YTFTFNH INWVKQRPGQGLDWIGV NPYNDY SYNQFKGKATLTVDKSSNTAYMLSSL       78
HB5         1 --PELRKPGETVKISCKASG YTFTDY KWHWVKQTPGKGLKWMCV NTKTGEF PKYADDFKGRFAFSLETSASTAILQINNL      78
HB6         1 --AELVRPGASVKLSCKASG YTFTFD EMHWVKQTPGHGLEWIGI SPGRSG AYNQKFKGKATLTADKSSRTAYMLSNL       78
HB7         1 --PELKKPGETVKISCKASG STFTN EMHWVKQAPGKGLKWMCW NTYYCEF TYADDFKGRFAFSLETSASTAFLQINNL       78
HB8         1 --GGIVKPGGSIRLSCAAS FTFSSY RMHWVRQPTPEKRLEWVAT SSGGSV YYPDSVKGRFTTSRDMAKNTLYLQMSSL       78
HB9         1 --AELVRPGASVRLSCKASG YTFTSY MSWVRQFPGNGLEWIGH MPSNGH NYNERFKMKATLTVDKSSTAYMQLSSL        78
HB10        1 --PSLVKPSQTLSLTCSVTG PESITS GFWNWIRKFPGNKLEYMGY ISYG-S TYNPSLKSRISITRDTSKMQYYLQLNSV       77
HB11        1 --AELVRPGASVKLSCKASG YTFTNYH HWVKQAPGSOGLEWIGM INPNNGHN NYNERFKNKASLTVDKSSTAYMQLSSL      78
HB12        1 SGAELVRPGASVNLSCKALG YTFTDY MEWVKQTPVYGLEWIGTI HPRRGG AYNQRFKGKAALTADKSSTAYMELSSL        80
HB14        1 --AELVIPGASVKVSCKASG YTFTTSY WIEWVKQWPGQSLEWIGE INPNNGH NYNEKFKSKATLTVDKSSTAYMQLSSL      78
HB17        1 --PELKKPGETVKISCKASG YTFTSY NIQWVKQRPGQSLEWIGE INPTNGHN NYNEKFKTKATLTVDKSSTAYMRLSSL      78
HB20        1 --PGLVAPSQSLSITCTVSG HSFTN WSDG-S TVNSALKSRLSISKDNSKSQVFLKMNSL       77
HB22        1 --PGLVAPSQSLSITCTVSG HSLTN .Yspp Kt+hsio.DpSpsp.ndppns SL
Consensus_aa: ..s.IV.Pt.c.p.cCpbc GenTGY .pWV+Q.Psp.L-W.GI.                                                77
Consensus_ss:                              CDR-1                             CDR-2
```

```
                                                   FR-4
              7969  95955                         6699699   9799699999999966696699969999
Conservation:
72A1     79 TSEDSAVYYC AGGLRR-VN----WFA WGQGTLVSVSAAKTPPSVYPLAPGSAAQTNSMVTLG  137 SEQ ID NO: 100
HB1      78 QTDTAMYYC QTRDRGI-GYLY--AMD WGQGTSVTVSSAKTTPSVYPLAPSVYPLAPGSAAQTNSMVTLG  138 SEQ ID NO: 102
HB2      79 KNEDTATYFC APYGYA------LD WGQGTSVTVSSAKTTPSVYPLAPSVYPLAPGSAAQTNSMVTLG  134 SEQ ID NO: 104
HB3      79 TSEDSAVYYC ARSEGW-LRRG-AWFA WGQGTLVTVSSAKTTAPSVYPLAPSVYPLAPGSAAQTNSMVTLG  137 SEQ ID NO: 106
HB5      79 KNEDTATYFC APYGYA------LD WGQGTSVTVSSAKTTPSVYPLAPSVYPLAPGSAAQTNSMVTLG  140 SEQ ID NO: 108
HB6      79 TSEDSAVYYC GSR------YGHP-SYLF WGAGTSVTVSSAKTTPSVYPLAPSVYPLAPGSAAQTNSMVTLG  134 SEQ ID NO: 110
HB7      79 KNEDTAIYYC ARYYGSVYSA-WFA WGAGTSVTVSSAKTTPSVYPLAPSVYPLAPGSAAQTNSMVTLG  135 SEQ ID NO: 112
HB8      79 KSEDTAIYYC TREDFY-YGSSGFFD WGAGTSVTVFSSAKTTPSVYPLAPSVYPLAPGSAAQTNSMVTLG  140 SEQ ID NO: 114
HB9      79 TSEDSAVYYC ARNLYY-YGRP---D WGQGTSVTVSSAKTTPSVYPLAPSVYPLAPGSAAQTNSMVTLG  141 SEQ ID NO: 116
HB10     79 TTEDTATYYC ARGMGG-NYDW--YFD WGQGTSVTVSS------------------------------  137 SEQ ID NO: 118
HB11     78 TSEDSAVYYC AR----YGNP-WYFD WGQGTSVTVSS------------------------------  138 SEQ ID NO: 120
HB12     79 TSEDSAVYYC AR----YGYP-WYFD WGAGTTVTVSS------------------------------  111 SEQ ID NO: 122
HB14     81 TSEDSAVYYC ARMLFY-YGRP---D WGQGTSVTVSSAKTTPSVYPLAPSVYPLAPGCGDTTGSSVTLG  112 SEQ ID NO: 124
HB17     79 TSEDSAVYYC ARNLYY-YGRP---D WGQGTSVTVSSAKTTPSVYPLAPSVYPLAPGSAAQTNSMVTLG  137 SEQ ID NO: 126
HB20     79 TSEDSAVYYC ARNYYGNSYPA--WFA WGQGTLVTVSSAKTTPSVYPLAPSVYPLAPGSAAQTNSMVTLG  137 SEQ ID NO: 128
HB22     78 QTDDTAMYYC R--------------D WGQGTLVTVSSAKTTPSVYPLAPSVYPLAPGSAAQTNSMVTLG  139 SEQ ID NO: 130
Consensus_aa:  poEDoAhYYC.R                  .WG.GT.VTVS tAKTTsPSVYPLAPstts pS.VTLG
Consensus_ss:  hhh                 CDR-3
```

```
Conservation:        6   996  6      69666
72A1       1  QAVLTQESALTTSPGETVTLTCRSSTGAVT--TSN
HB1        1  ------KFMSTSVGDRVSVTCKASQNV-----GTN
HB2        1  ------AILSASPGEKVTMTCRATSS---------
HB3        1  ------SSLSASLGDRVTISCRASQS---------
HB5        1  ------AILSVSPGHRVSFSCRASQS---------
HB6        1  ------AILSASPGEKVTMTCRATSS---------
HB7        1  ------KFMSTSVGDRVNITCKASQD---------
HB8        1  ------LSLPVSLGDQASISCRSSQSIVHSNGNTY
HB9        1  ------LSLPVSLGDQASISCRSSQSIVHSNGNTY
HB10       1  ------SSLSASLGDRVTMSCRASSQ---------
HB11       1  ------AIMSASLGEKVTMSCRASSQ---------
HB12       1  ------LSLPVSLGDQASISCRSSQSLVHSNGNTY
HB14       1  ------LSLPVSLGDQASISCRSSQSIVHDNGNTY
HB17       1  ------SSLSASLGDRVTISCRASQS---------
HB20       1  ------SSLSASLGDRVTISCRASQS---------
HB22       1  ------LSLPVSLGDQASISCRSSQSIVHSNGNTY
Consensus_aa: ......hsbS.G-pbohoCRtSps.......sss
Consensus_ss:
                                  CDR-1
```

FR-2

```
     6   966  69  99669  6    966 69 99669
ANWVQEKPDHLFTGLIGTN NRVPGVPARFSGSLIGDKAALTIT      78   SEQ ID NO: 101
VAWYQQKPGQSPKALIYSTS RYTGVPDRFAGSGSGTDYTLTIS      69   SEQ ID NO: 103
VNMHWYQQKPGSSPKPWIYATS NLASGVPARFSGSGSGTSYSLTIS   68   SEQ ID NO: 105
LHWYQQRTNDSPRLLIYASF SISGIPPRFSGSGSGTDFTLSIN       67   SEQ ID NO: 107
IGTS VNMHWYQQKPGSSPKPWIYATS NLASGVPARFSGSGSGTSYSLTIS  68  SEQ ID NO: 107
GNR VAWFQQKPGQSPKLLIY LEWYLQKAGSPKALIY...         68   SEQ ID NO: 109
IVHSNGNTY LEWYLQKAGSPKLLIY KVSNRFSGVPDRFSGSGSGTDFTLKIS  68  SEQ ID NO: 111
IGMLNWYQQKPGQSPKLLIY KVSNRFSGVPDRFSGSGSGNSYSLTIS  73   SEQ ID NO: 113
V-NPMNWYQQKPDGTVKLLIY ISNLAFGVPARFSGSGSGSGTDFTLKIS  69  SEQ ID NO: 115
IGMLNWYQQKPGQSPKLLIY KVSNRFSGVPSRFSGSGSGTDFTLKIS  67   SEQ ID NO: 117
IGMLNWYQQKPGQSPKLLIY KVSNRFSGVLDKFSGSGSGTDFTLKIS  73   SEQ ID NO: 119
IGNLNWYQQKPGQSPKLLIY KVSNRFSGVPSRFSGSGSGTDFTLKIS  73   SEQ ID NO: 121
IGMLNWYQQKPGQSPKLLIY KVSNRFSGVPSRFSGSGSGTDFTLKIS  73   SEQ ID NO: 123
IGMLNWYQQKPGQSPKLLIY KVSNRFSGVPSRFSGSGSGTDYSLTIS  68   SEQ ID NO: 125
IGMLNWYQQKPGQSPKLLIY KVSNRFSGVPSRFSGSGSGTDYSLTIS  69   SEQ ID NO: 127
IGMLNWYQQKPDGTVKLLIY KVSNRFSGVPSRFSGSGSGTDYSLTIS  73   SEQ ID NO: 129
                                                      SEQ ID NO: 131
```

FR-3

```
Conservation:        6   99  6   99  6
72A1      79  GAQTEDEAIYFCQ VLMHS-NHWVEGGTKLTVL          109  SEQ ID NO: 101
HB1       69  NVQSEDLAEYFCQ QYNT--YPYTF GGTRLDIKRADAAPTV   107  SEQ ID NO: 103
HB2       68  RVEAEDAATYYCQ QWSSNPP-TF GAGTKLELKRADAAPTV    106  SEQ ID NO: 105
HB3       69  NLEEDIATYFCQ QGNTLPP-TF GGGTKLEIKRADAAPTV     107  SEQ ID NO: 107
HB5       69  SVESEDIADYHCQ QNSWPMLIF GAGTKLELKRADAAPTV     108  SEQ ID NO: 109
HB6       68  RVEAEDAATYYCQ QWSSNPP-TF GAGTKLELKRADAAPTV    106  SEQ ID NO: 111
HB7       69  NMQSEDIADYFCQ QYSS-YPITF AGTKLELKRADAAPTV     112  SEQ ID NO: 113
HB8       74  RVEAEDLGVYYCFQ GSH-VPYTF GGTKLEIKRADAAPTV     115  SEQ ID NO: 115
HB9       74  RVEAEDLGVYYCFQ GSH-VPYTF GGTKLEIKRADAAPTV     117  SEQ ID NO: 117
HB10      59  NLEEDIATYFCQ QFTSSPSWTF GGGTKLEIKRADAAPTV     119  SEQ ID NO: 119
HB11      68  GMEGEDAATYYCQ QFSQSTH-VPLTF SGTKLEIK----      121  SEQ ID NO: 121
HB12      74  RVEAEDLGVYFCQ QVPPTF-VPPTF GGTKLEIK----        123  SEQ ID NO: 123
HB14      74  RVEAEDLGIYYCFQ GSH-VPPTF GGGTKLEIKRADAAPTV    104  SEQ ID NO: 125
HB17      69  NLEEDIATYFCQ QGNALPP-TF GGGTKLEIKRADAAPTV     107  SEQ ID NO: 127
HB20      69  NLEQEDIATYFCQ QGSH-VPWTF GGGTKLEIKRADAAPTV    107  SEQ ID NO: 129
HB22      74  RVEAEBLGVYFCQ QGSH-VPWTF GGGTKLEIKRADAAPTV    112  SEQ ID NO: 131
Consensus_aa:  .hpsEDts.Y.Cp.sp.s..TFG+GTKL-lKRADAAPTV
Consensus_ss:                      hhhh
                                  CDR-3
```

Fig. 4A i. Heavy chain (VH)

```
m72A1  MGWRWIFLFLLSGTAGVHSEVQLQQSGPELVKPGTSMKISCKASGSSFTDYTMNWMKQSH
h72A1  ------------------EVQLVESGGGLVQPGGSLRLSCAASGSSFTDYTMNWMRQSP
                          **::**  **:;** *::;**  *************:***:

m72A1  GKNLEWIGLINPYNGGTRYNQKFKGRATTLTDKSSSTAYMEVLSLTSEDSAVYYCAGGLR
h72A1  GKGLEWIGLINPYNGGTRYADSVKGRATLSLIDESKNTAYLQMNSLRAEDTAIYYCAGGLR
        **********  . :**:;*::.: :: :**:*:******* m72A1  RVNWFAYWCQGTLVEVSA
h72A1  RVNWFAYWGQGTLVTVSS
       ******** *****.***
``` ii. Light chain (VL)

```
m72A1  MAWISLILSLLALSSGAISQAVLTQESSALTTSPGETVILTCRSSTGAVTTSNYANWVQEK
h72A1  -------------------DAQLTQSPILLSASVGDRVTITCRSSTGAVTTSNYANWVQER
                          *  ****.* *:***: *:*:***:**********:****

m72A1  PDHLFTGLIGTNNRVEGVPARFSGSLIGDKAALTITGAQTEDEAIYFCVLWHSNHWVFG
h72A1  TNGSPRGLIGSTNNRVPGVPSRFSGSLSGSDDATLTISSLQPEDEADYFCVLWHSNHWVFG
       ..   *.**:* *:****** * **** *  * :** *********** m72A1  GGTKLTVL-
h72A1  AGTKVEIKR
       .***: :
```

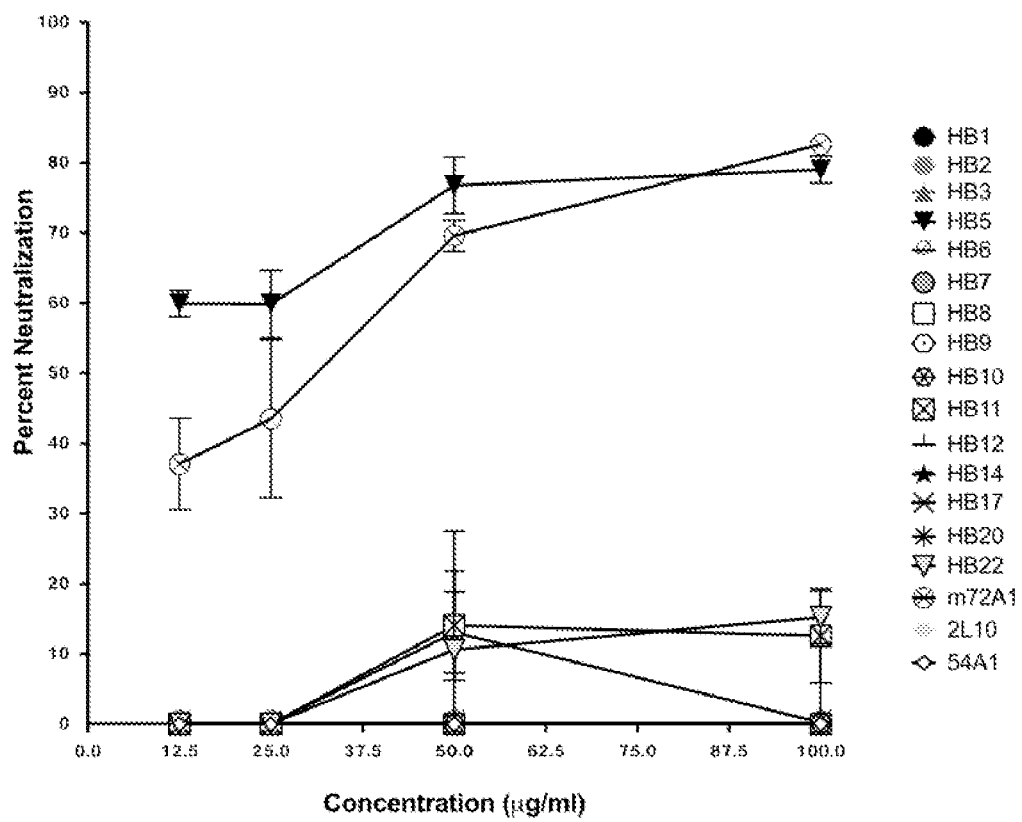

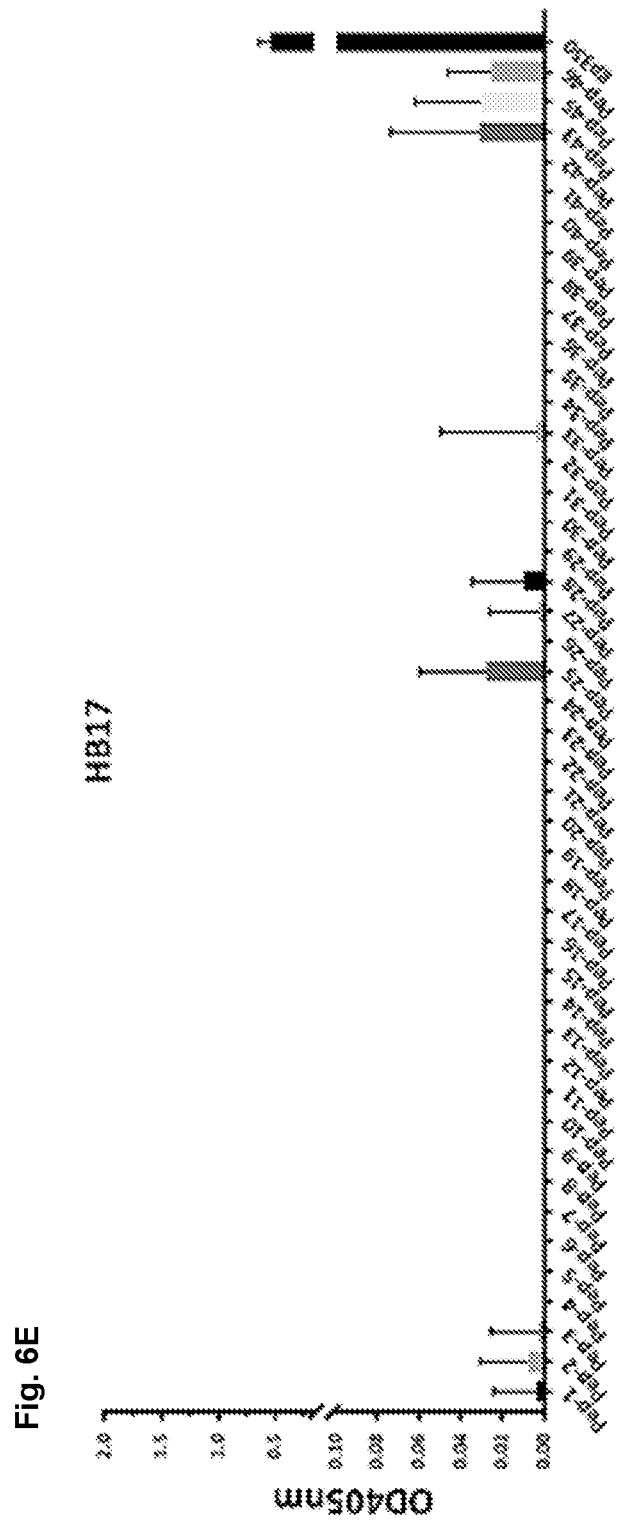

Fig. 7A

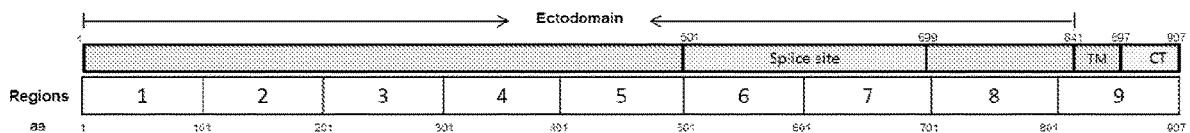

Fig. 7B

```
  1 MEAALLVCQY TIQSLIHLTG EDPGFFNVEI PEFPFYPTCN VCTADVNVTI NFDVGGKKHQ
 61 LDLDFGQLTP HTKAVYQPRG AFGGSENATN LFLLELLGAG ELALTMRSKK LPINVTTGEE
121 QQVSLESVDV YFQDVFGTMN CHHAEMQNPV YLIPETVPYI KWDNCNSTNI TAVVRAQGLD
181 VTLPLSLPTS AQDSNFSVKT EMLGNEIDIE CIMEDGEISQ VLPGDNKFNI TCSGYESHVP
241 SGGILTSTSP VATPIPGTGY AYSLRLTPRP VSRFLGNNSI LYVFYSGNGP KASGGDYCIQ
301 SNIVFSDEIP ASQDMPTNIT DITYVGDNAT YSVPMVTSED ANSPNVTVTA FWANPMNIET
361 DFKCKWTLTS GTPSGCENIS GAFASNRTFD ITVSGLGTAP KTLIITRTAT NATTTTHKVI
421 FSKAPESTTT SPTLNTTGFA DPNTITGLPS STHVPTNLIA PASTGPTVST ADVTSPTPAG
481 TTSGASPVTP SPSPWDNGTE SKAPDMTSST SPVTTPTPNA TSPTPAVTTP TPNATSPTPA
541 VTTPTPNATS PTLGKTSPTS AVTTPTPNAT SPTLGKTSPT SAVTTPTPNA TSPTLGKTSP
601 TSAVTTPTPN ATGPTVGETS PQANATNHTL GGTSPTPVVT SQPKNATSAV TTGQHNITSS
661 STSSMSLRPS SNPETLSPST SDNSTSHMPL LTSAHPTGGE NITQVTPASI STHHVSTSSP
721 APRPGTTSQA SGPGNSSTST KPGEVNVTKG TPPQNATSPQ APSGQKTAVP TVTSTGGKAN
781 SITGGKHTTG HGARTSTEPT TDYGGDSTTP RPRYNATTYL PPSTSSKLRP RWTFTSPPVT
841 TAQATVPVPP TSQPRFSNLS MLVLQWASLA VLTLLLLLVM ADCAFRRNLS TSHTYTTFPY
901 DDAETYV
```

Fig. 10A i. Heavy chain

```
mE1D1  LPEFEVKLQESGPELVKPGASVKMSCKASGYTFTDYVISWKQRTGQGLEWIGEIYPESG
hE1D1  ----EVQLVESGGGLVQPGGSLRLSCAASGYTFTDYVISWVRQSPGKGLEWIGEIYPESG
             *::******  :*:*************  :* ************* mE1D1  NTYYNEKFKGEATLTADKSSNTAYMQLSRLTSEDSAVYFCAEGYAMDFWGQGTSVTVSSA
hE1D1  NTYYADSVKGRATLSADKSKNTAYLQMNSLRAEDTAIYFCAEGYAMDFWGQGTLVTVSS-
       ****   :* **:*.****:*:.::::*************.*** mE1D1  KTTPPSVYPLAPGSAAQTNSMVTLGCLVKGYFPE
hE1D1  ------------------------------
``` ii. Light chain

```
mE1D1  DIVMTQTPLSLPVSLGDQASISCRSSQSLLHSNGNTYLHWYLQRPGQSPKLLIYKVSNRF
hE1D1  DIQMTQSPILLSASVGDRVTITCRSSQSLLHSNGNTYLHWYQQRTNGSPRLLIYKVSNRF
       :*:*:*:*:*** .:*:***************  *.**************** mE1D1  SGVPDRFSGSGSGTDFTLMISRVEAEDLGVYFCSQSIHVPRTFGGGTKLEIKRADAAPTV
hE1D1  SGVPSRFSGSGSGTDFTLTISSLQPEDEADYFCSQSIHVPRTFGAGTKVEIKR-------
       **.***********  :*: :*:*: **********.*:**** mE1D1  SIFPPSSKLG
hE1D1  ------------
```

SDS-PAGE analysis of purified antibodies under reducing conditions

Schematic diagram of murine, chimeric, humanized and human antibodies

ELISA binding of (i) anti-gp350 and (ii) anti-gH/gL to soluble gp350 and gH/gL proteins

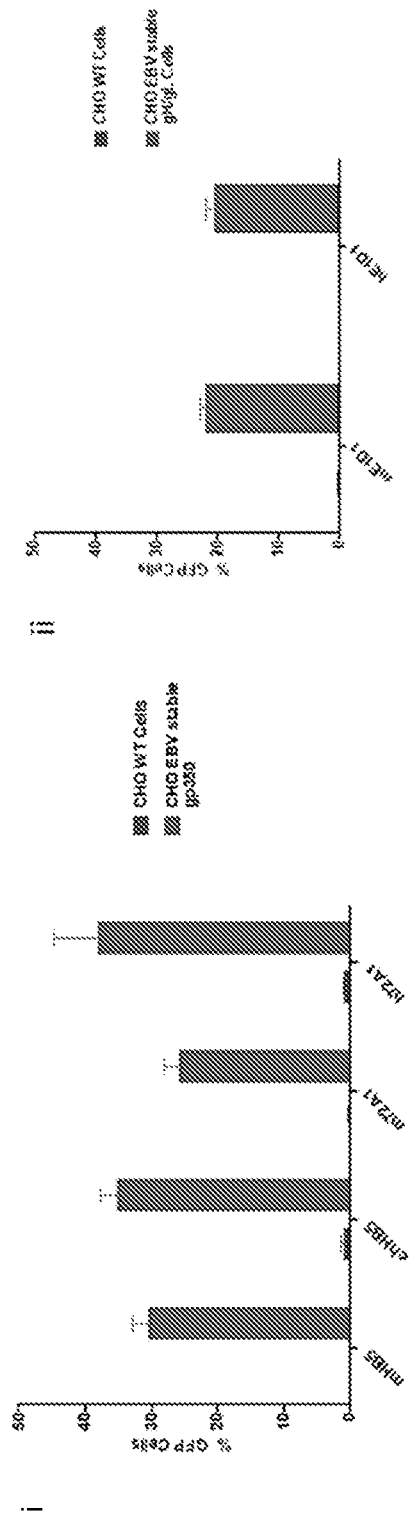

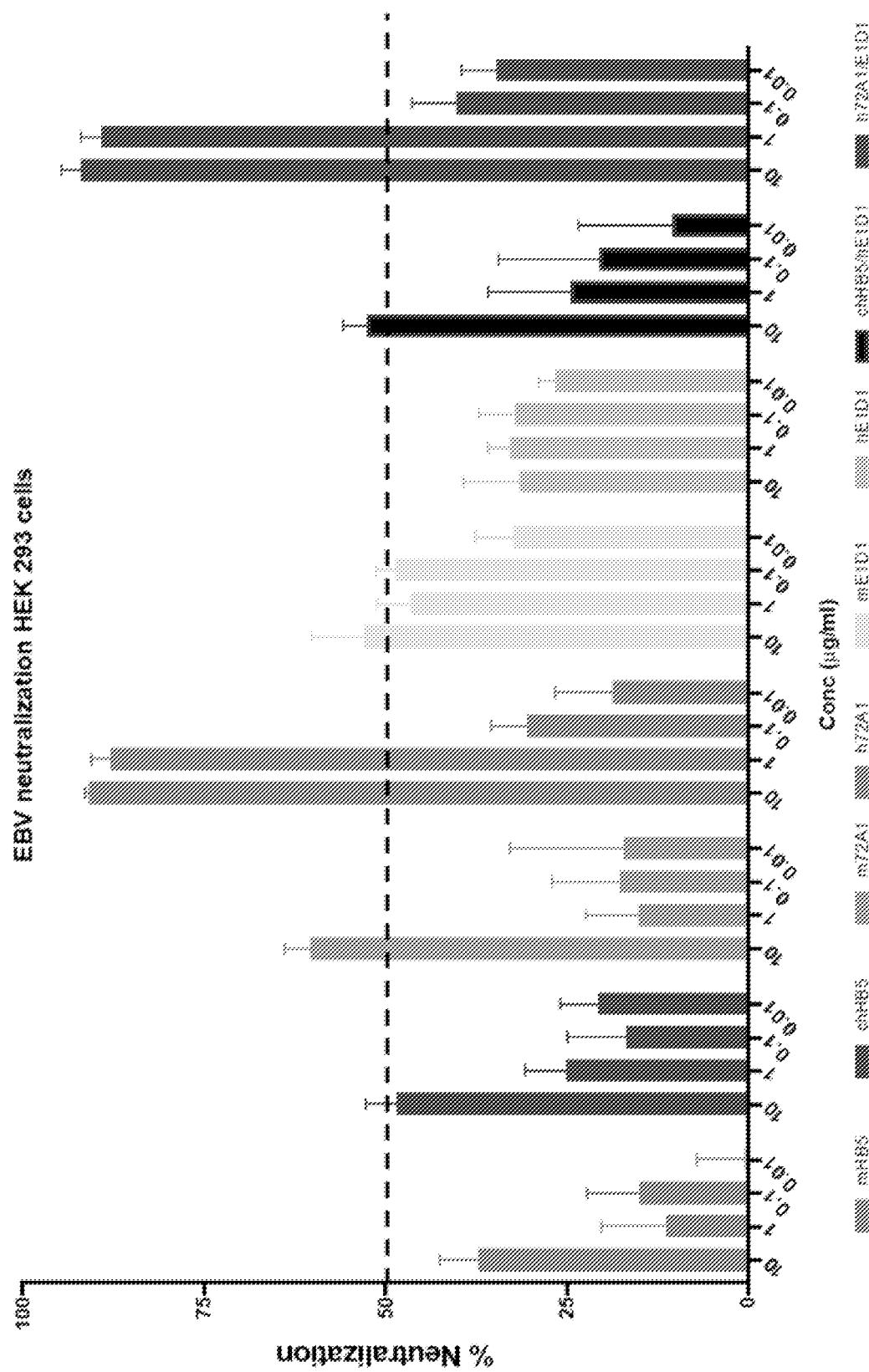

EPSTEIN-BARR VIRUS ANTIBODIES AND USES THEREOF

STATEMENT OF GOVERNMENT INTEREST

The present invention was made with government support under Grant Nos. R21CA205106 and R21CA232275, awarded by the National Institutes of Health. The Government has certain rights in the invention.

PRIORITY CLAIM

The present disclosure provides antibodies or immunogenic fragments thereof that bind to Epstein-Barr virus (EBV) glycoprotein 350 (gp350) or 220 or one or more immunogenic peptides. Immunogenic peptides comprising fragments of gp350 amino acid sequence, EBV antibody-small molecule conjugates and pharmaceutical compositions comprising the antibody or an immunogenic fragment thereof, one or more immunogenic peptides, or the EBV antibody-small molecule conjugate are also provided. The antibodies, immunogenic peptides, conjugates, and pharmaceutical compositions provided by the present disclosure can be used to treat or prevent EBV infections and EBV-associated conditions and diseases.

SEQUENCE LISTING

This disclosure includes a sequence listing, which is submitted in ASCII format via EFS-Web, and is hereby incorporated by reference in its entirety. The ASCII copy, created on Jun. 16, 2022, is named SequenceListing.txt and is 83 kilobytes in size.

BACKGROUND

Epstein-Barr virus (EBV) infection is the causal agent of acute infectious mononucleosis (62, 63). Persistent EBV infection in immunodeficient individuals is associated with numerous epithelial and lymphoid malignancies, such as nasopharyngeal carcinoma, gastric carcinoma, Burkitt lymphoma, Hodgkin lymphoma, and post-transplant lymphoproliferative diseases (PTLD) (1). Transplantation is the treatment of choice for a variety of patients with end-stage organ failure or hematologic malignancies, or in need of reconstructive transplantation (1). Transplantation success depends entirely on potent immunosuppressive drugs to prevent stem cell/organ rejection. However, these drugs impose several serious side effects, including an increased risk of infection with or reactivation of Epstein-Barr virus (EBV), and the resultant development of PTLDs, which are aggressive, life-threatening complications (2, 3). Through the early 2000s, PTLD patients who had been EBV-naïve prior to transplantation showed mortality rates of 50-90% for stem cell and solid organ transplants; while recent data suggest outcomes have improved, challenges remain. PTLDs usually develop in EBV-naïve patients, particularly pediatric patients, who receive organs from EBV+ donors. A variety of non-standardized, non-specific treatments are used to treat EBV+ PTLD cases (4-9). Initial clinical management typically involves reduction of immunosuppression; however, this can lead to graft-versus-host disease. Other treatments including radiation/chemotherapy and excision of PTLD lesions all have undesirable side effects. Second-line treatment often includes antibodies (Abs) against the B cell antigen, CD20; however, this also targets healthy B cells, further weakening the immune system and exposing patients to other opportunistic infections.

In over 50 years of EBV vaccine research, few candidates have demonstrated partial clinical efficacy, and none have been efficacious enough to elicit sterilizing immunity and be licensed (24). Antibodies, whether elicited in the host naturally or via passive immunization, provide an effective first-line of defense against viral infection.

Thus, there is an urgent need for a novel EBV-specific therapy that targets EBV+ cells to neutralize EBV infection and prevent subsequent PTLD development in EBV-naïve patients.

SUMMARY

In one aspect, this disclosure relates to an Epstein-Barr virus (EBV) antibody or an immunogenic fragment thereof. In some embodiments, the EBV antibody or an immunogenic fragment thereof specifically binds to EBV glycoprotein 350/220. In some embodiments, the EBV antibody comprises a VH region comprising CDR-1, CDR-2, and CDR-3 represented by SEQ ID NOs: 5-19, 21-35, and 37-51, respectively. In some embodiments, the EBV antibody comprises a VL region comprising CDR-1, CDR-2, and CDR-3 represented by SEQ ID NOs: 53-67, 69-83, and 85-99, respectively. In some embodiments, the EBV antibody is a monoclonal antibody. In some embodiments, the EBV antibody is a chimeric antibody, a human antibody, or a humanized antibody. In some embodiments, the EBV antibody is a neutralizing antibody. In some embodiments, the EBV antibody is humanized 72A1 or humanized E1D1. For example, the EBV antibody comprises one or more CDRs of antibody clone 72A1. In another example, the EBV antibody comprises one or more CDRs of antibody clone E1D1. In some embodiments, the EBV antibody comprises a heavy chain having an amino acid sequence of SEQ ID NO: 180, SEQ ID NO: 185, or a sequence at least 90%, at least 95%, at least 98%, or at least 99% identical to SEQ ID NO: 180 or SEQ ID NO: 185. In some embodiments, the EBV antibody comprises a light chain having an amino acid sequence of SEQ ID NO: 181, SEQ ID NO: 186, or a sequence at least 90%, at least 95%, at least 98%, or at least 99% identical to SEQ ID NO: 181 or SEQ ID NO: 186.

In another aspect, this disclosure relates to an immunogenic peptide comprising the amino acid sequence of a fragment of EBV350 such as AA1-101, AA102-201, or AA402-501, or an amino acid sequence identical to or sharing at least 60% similarity to the fragment. In some embodiments, the immunogenic peptide further comprises a known immunogenic peptide such as keyhole limpet hemocyanin (KLH) peptide.

In another aspect, this disclosure relates to an EBV antibody-small molecule conjugate. The EBV antibodies disclosed herein can be conjugated to small molecules having activities against EBV-transformed cells. For example, the small molecules have anti-proliferative activities against EBV-transformed B lymphoma cells. In some embodiments, the small molecules are growth inhibitors of EBV infected B cells. In some embodiments, the small molecule is $L_2P_4$, 2-butynediamide, or a derivative thereof. In some embodiments, the small molecule is conjugated to the antibody via a linker or an adaptor. In some embodiments, the small molecule is conjugated to the constant region of the heavy chain or the light chain of the antibody.

In a related aspect, this disclosure relates to a pharmaceutical composition comprising one or more EBV antibodies disclosed herein or one or more immunogenic fragments thereof, one or more immunogenic peptides disclosed herein, or the EBV antibody-small molecule conjugate disclosed herein. The pharmaceutical composition can further comprise one or more pharmaceutically acceptable excipients. The pharmaceutical composition can be formulated into any suitable formulation depending on the administration route. In some embodiments, the pharmaceutical composition comprising a humanized 72A1, a humanized E1D1, or both.

In another aspect, this disclosure relates to a method of neutralizing EBV infection. The method includes administering to a subject infected with EBV a therapeutically effective amount of one or more EBV antibodies disclosed herein or one or more immunogenic fragments thereof, the EBV antibody-small molecule conjugate, one or more immunogenic peptides disclosed herein, or the pharmaceutical composition described above. In some embodiments, the subject is human. In some embodiments, the subject suffers from or at an elevated risk of suffering from EBV infection, such as EBV+ post-transplant lymphoproliferative diseases (PTLDs).

In another aspect, this disclosure relates to a method of treating or preventing EBV infection. The method includes administering to a subject at an elevated risk of EBV infection a therapeutically effective amount of one or more EBV antibodies disclosed herein or an immunogenic fragment thereof, the EBV antibody-small molecule conjugate, one or more immunogenic peptides disclosed herein, or the pharmaceutical composition described above. In some embodiments, the subject is human. In some embodiments, the EBV antibody is a humanized 72A1, or a humanized E1D1.

In another aspect, this disclosure relates to a method of preventing a post-transplant lymphoproliferative disease (PTLD). PTLD is associated with EBV infection of B cells, either as a consequence of reactivation of the virus post transplantation or from primary EBV infection. The method includes administering to a subject who is a transplant recipient a prophylactically or therapeutically effective amount of one or more EBV antibodies disclosed herein or an immunogenic fragment thereof, the EBV antibody-small molecule conjugate, one or more immunogenic peptides disclosed herein, or the pharmaceutical composition described above. The administration can be before, during, and/or after the transplant. In some embodiments, the subject is a pediatric transplant recipient who is EBV naïve. In some embodiments, the subject is an adult transplant recipient. In some embodiments, the subject is human.

In another aspect, this disclosure relates to a method of treating an EBV-associated cancer. The method includes administering to a subject suffering from an EBV-associated cancer a prophylactically or therapeutically effective amount of one or more EBV antibodies disclosed herein or an immunogenic fragment thereof, the EBV antibody-small molecule conjugate, one or more immunogenic peptides disclosed herein, or the pharmaceutical composition described above. In some embodiments, the examples of EBV-associated cancer include but are not limited to Hodgkin lymphoma, Burkitt lymphoma, gastric cancer, and nasopharyngeal carcinoma. In some embodiments, the subject is human. In some embodiments, the EBV antibody is a humanized 72A1, or a humanized E1D1.

In another aspect, this disclosure relates to a method of immunizing or vaccinating a subject against an EBV infection. The method includes administering to a subject suffering from an EBV infection a therapeutically effective amount of one or more EBV antibodies disclosed herein or an immunogenic fragment thereof, one or more immunogenic peptides disclosed herein, or the pharmaceutical composition thereof as described above. In some embodiments, the subject is human.

In another aspect, this disclosure relates to a method of inducing the production of neutralizing antibodies against an EBV in a subject. The method includes administering to a subject an effective amount of one or more immunogenic peptides disclosed herein. In some embodiments, the subject is human.

BRIEF DESCRIPTION OF THE DRAWINGS

FIG. 1A: SDS-PAGE analysis of anti-EBV gp350 antibodies purified from indicated hybridoma (HB) supernatants. FIG. 1B: ELISA screening of hybridoma (HB) supernatants for anti-gp350-specific antibodies. Soluble EBV gp350 protein was used as the target antigen at 0.5 μg/ml. m72A1 at 10 μg/ml and KSHV anti-gH/gL (54A1) were used as positive and negative (not shown) controls, respectively. Bound antibodies were detected using HRP-conjugated anti-mouse IgG (1:2,000). Twenty-three HB clones with ELISA signals two times greater than those of 54A1 control were considered to be positive/reactive to gp350. FIG. 1C: Immunoblot analysis with gp350-transfected stable CHO lysate to determine specificity of anti-gp350-producing HB supernatants. FIG. 1D: Flow cytometric analysis of surface expression of gp350 protein on gp350 expressing CHO cells. Cells were stained with indicated anti-gp350 mAb (1:250), followed by secondary goat anti-mouse conjugated to AF488. FIG. 1E: Flow cytometric analysis of HB5, HB17 and HB19.

FIGS. 3A and 3B show PROMALS3D multiple sequence alignment of VH (FIG. 3A) and VL (FIG. 3B) regions of 15 mAbs and nAb-72A1 (SEQ ID NOS:100-131). The highly variable complementarity determining regions (CDR) 1-3, indicated by black boxes, define the antigen binding specificity. The conserved framework regions (FR) 1-4 flank the CDRs. Consensus amino acid (AA) are in bold and upper case. Consensus predicted secondary structure (ss) symbols: alpha-helix: h and beta-strand: e.

FIGS. 4A-4D show the comparison of murine 72A1 (m72A1) and humanized 72A1 (h72A1). FIG. 4A: Sequence comparison of murine (m72A1) and humanized (h72A1) 72A1. ClustalW alignment of heavy chain (i) and light chain (ii) variable region amino acid sequences. Murine 72A1 heavy chain and light chain AA sequences are represented by SEQ ID NOs: 178 and 179, respectively, and humanized 72A1 heavy chain and light chain AA sequences are represented by SEQ ID NOs: 180 and 181, respectively. Regions of identical sequence are represented by *. Regions of similarity are represented by :. FIG. 4B: ELISA comparison screening of m72A1 and h72A1 for anti-gp350-specificity. Soluble EBV gp350 protein was used as the target antigen at 0.5 μg/ml. m72A1 and h72A1 were serially diluted (5-0.062 μg/ml) and 1× phosphate buffered saline (PBS) was used as a negative control (data not shown). Bound h72A1 and m72A1 antibodies were detected using HRP-conjugated anti-mouse IgG and anti-human IgG (1:2,000) as relevant. FIG. 4C: ELISA determining the reactivity of humanized 72A1 to murine IgG. Soluble EBV gp350 protein was used as the target antigen at 0.5 μg/ml. Plates were incubated with 10 µg/ml of m72A1 and h72A1, followed by three washes. Bound antibodies were detected using HRP-conjugated anti-mouse IgG or anti-human IgG (1:2,000). FIG. 4D: Flow cytometric analysis of m72A1 and h72A1 gp350 specificity. CHO wild-type cells and gp350-expressing CHO cells were stained with m72A1 and h72A1, followed by secondary goat anti-mouse or anti-human conjugated to AF488. Unstained cells and cells stained with secondary goat anti-mouse or anti-human conjugated to AF488 alone were used as negative controls.

FIGS. 5A-5C show neutralization activity of novel anti-gp350 mAbs against EBV-eGFP in Raji cells. FIG. 5A: EBV-eGFP titration in Raji cells to determine optimal dose of infection. FIG. 5B: EBV-eGFP was pre-incubated with 15 indicated serial diluted (12.5-100 µg/ml), maxispin column-purified anti-gp350 mAbs, followed by incubation with $10^5$ Raji cells for 48 hours. EBV-eGFP+ cells were enumerated using flow cytometry. Anti-gp350 (m72A1) nAb served as positive control and non-neutralizing anti-gp350 (2L10) mAb and anti-KSHV gH/gL mAb (54A1) served as negative controls. FIG. 5C: EBV-eGFP was pre-incubated with 7 indicated serially diluted (12.5-100 µg/ml) protein G affinity chromatography- and size-exclusion chromatography-purified anti-gp350 mAbs, followed by incubation with $10^5$ Raji cells for 48 hours. EBV-eGFP+ cells were enumerated using flow cytometry. Anti-gp350 (m72A1 and h72A1) nAbs served as positive controls and anti-KSHV gH/gL mAb (54A1) served as negative control.

FIGS. 6A-6I show the linear peptide epitope mapping of gp350 of various antibodies. ELISA was used to detect the responses of the indicated antibodies against each linear peptide. ELISA plates were coated overnight with 10 µg/ml of each of the indicated 45 linear peptides and 0.5 µg/ml of recombinant purified gp350 protein was used as a positive control. Plates were blocked for 1 hour, washed three times, and incubated with 10 µg/ml of each antibody for 2 hours. Bound antibodies were detected using HRP-conjugated anti-mouse IgG or anti-human IgG (1:2,000).

FIGS. 7A-7B show the schematic diagram (FIG. 7A) and the amino acid sequence (FIG. 7B, SEQ ID NO:182) of EBV gp350 protein, illustrating the ectodomain and the splice site (AA 501-699) for making gp220, the transmembrane domain, TM (AA 841-897) and the cytoplasmic domain, CT (AA 898-907). To analyze and classify binding of anti-gp350 mAbs to linear epitopes on the protein, EBV gp350 was separated into 9 regions of ~100 AA.

FIG. 8A: Construction of chimeric Ab. FIG. 8B: Example of the cloning strategy of heavy chain and light chain variable regions into expression vectors. FIG. 8C: PCR amplification of heavy chain and light chain variable regions. 72A1 and clone 19 were used as examples of PCR amplification.

FIGS. 10A-10B show the comparison of murine E1D1 (mE1D1) and humanized E1D1 (hE1D1). FIG. 10A: Sequence comparison of mE1D1 and hE1D1. Alignment of heavy chain (i) and light chain (ii) variable region amino acid sequences by the Clustal W. Murine E1D1 heavy chain and light chain AA sequences are represented by SEQ ID NOs: 183 and 184, respectively, and humanized E1D1 heavy chain and light chain AA sequences are represented by SEQ ID NOs: 185 and 186, respectively. Regions of identical sequence are represented by *. Regions of similarity are represented by :. FIG. 10B: Flow cytometric analysis of mE1D1 and hE1D1 gH/gL specificity. CHO wild type cells and gH/gL-expressing CHO cells were stained with mE1 D1 and hE1 D1, followed by secondary goat anti-mouse or anti-human conjugated to AF488. Unstained cells and cells stained with secondary goat anti-mouse or anti-human conjugated to AF488 alone, were used as negative controls.

FIGS. 11A-11F demonstrate biochemical characterization of chimeric and humanized antibodies. FIG. 11A is a schematic diagram of murine (m), chimeric (ch), humanized (h) and human antibodies. FIG. 11B shows SDS-PAGE analysis of antibodies under reducing conditions after purification using size exclusion chromatography. FIG. 11C shows ELISA determining the reactivity of chimeric and humanized antibodies to murine IgG. FIG. 11D shows Western blot analysis of anti-gp350 antibodies detecting liner epitopes. FIG. 11E shows ELISA binding of (i) anti-gp350 and (ii) anti-gH/gL to soluble gp350 and gH/gL proteins. FIG. 11F shows flow cytometric analysis of (i) gp350 and (ii) gH/gL specificity.

FIGS. 12A-12C show the EBV inhibitory effect of anti-gp350 and anti-gH/gL neutralizing antibodies in epithelial and B cells in vitro. Neutralization activity of single and combination anti-gp350 and anti-gH/gL in HEK 293 cells (12A), SVKCR2 cells (12B) and Raji cells (12C). Black dotted line represents 50% neutralization activity.

DETAILED DESCRIPTION

Figure 1A:
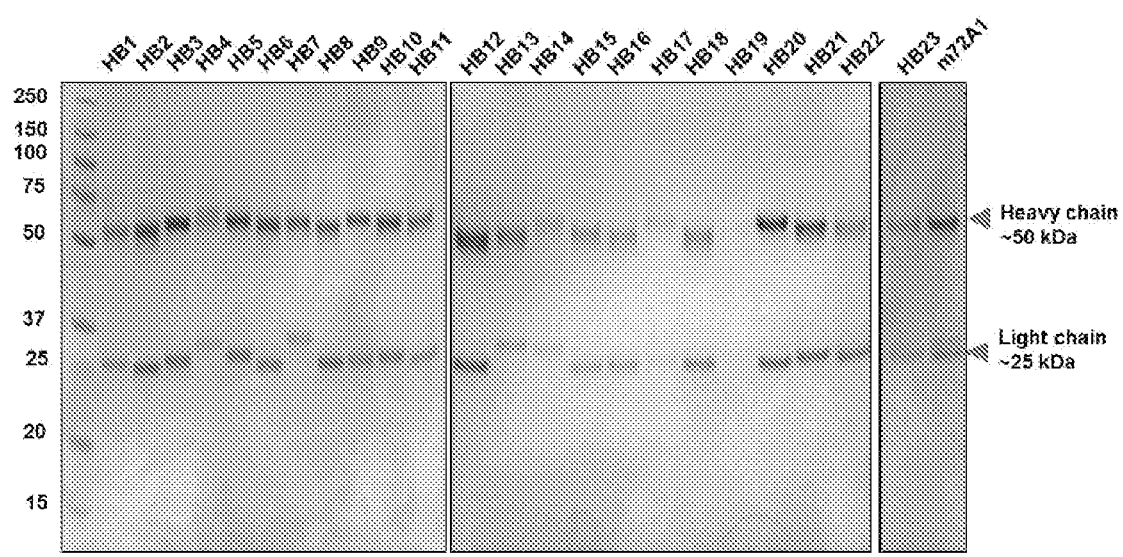
FIGS. 1A-1E show specificity of the novel anti-gp350 mAbs.

Epstein-Barr virus (EBV) predominantly infects epithelial cells and B cells, reflecting the viral tropism and cellular ontogeny characteristic of most EBV-associated malignancies (1). Despite the fact that EBV infection is associated with more than 200,000 cases of a variety of human malignancies every year, and has significant public health impacts, there is no licensed vaccine to date (20). The EBV glycoprotein gp350/220 (gp350) is a known target for a host's virus neutralizing antibody (nAb) response upon natural EBV infection (52, 67, 71) or immunization, and thus has been tested as a viable target for vaccines and therapeutics in five clinical trials to prevent B cell infection (30, 32-35). However, not all of the potential nAb epitopes on gp350 have been identified or fully characterized.

EBV infects at least 90% of the human population globally, irrespective of geographical location. Currently, there are two models describing how initial EBV infection of human host cells occurs in vivo (72). In the first infection model, the incoming virus first targets epithelial cells and engages with host ephrin receptor tyrosine kinase A2 via heterodimeric glycoproteins gH/gL (73, 74) or with host integrins via BMRF-2 (75, 76). This triggers fusion of EBV glycoprotein gB with the host epithelial cell membrane to enhance viral entry into the cytoplasm. This interaction is thought to occur in the oral mucosa; there, EBV undergoes lytic replication in epithelial cells to release virions that subsequently infect resting B cells in tonsillar crypts or circulating naïve B cells. In the alternative infection model, the incoming virus binds to B cells in the oral mucosa via host CD35 (45) and/or CD21 through its major immunodominant glycoprotein, gp350 (55, 65). The interaction between gp350 and CD35 and/or CD21 triggers viral adsorption, capping, and endocytosis into B cells (66). This subsequently leads to the heterotrimeric EBV glycoprotein complex gp42/gH/gL binding to host HLA class II molecules to activate gB membrane fusion and infection of B cells (17). Once infected, B cells typically remain latent and harbor the virus for life, but may also traffic back to the oropharynx, where EBV is amplified by lytic replication in epithelial cells, and shed into the saliva (72). Thus, B cells are the main reservoirs for EBV reactivation and for the development of virus-related malignancies (77). Novel strategies that could block interactions between EBV glycoproteins and cellular receptors that mediate viral infection could be beneficial in the development of effective antiviral therapies.

Antibodies are the first line of defense against viral infection and nearly all EBV-infected individuals develop nAbs directed to the ectodomain of EBV gp350 (52, 67, 71). A recent study showed that polyclonal serum antibodies against gp350 from naturally infected individuals or immunized animals block EBV infection of B cells in vitro better than antibodies against EBV gH/gL or gp42 (78). Thus, gp350 is a promising candidate for development of EBV vaccines against B cell infection; however, to make effective vaccines, the nAbs epitopes on the gp350 ectodomain must be identified and fully characterized.

Disclosed herein are EBV antibodies or immunogenic fragments thereof that specifically bind to gp350/gp220, immunogenic peptides, and EBV antibody-small molecule conjugates for treating or preventing EBV infection, in particular, in subjects receiving a transplant. In some embodiments, chimeric (human/mouse) anti-gp350 nAbs or humanized antibodies or functional fragments thereof are conjugated to $L_2P_4$ to obtain an EBV-specific ADC that improves the therapeutic efficacy of treating EBV-associated PTLDs. $L_2P_4$ described by Jiang et al., *Nature Biomedical Engineering* 1: 0042 (2017), is an example of the small molecules encompassed by this disclosure.

The term "antibody" as used herein refers to an immunoglobulin molecule or an immunologically active portion thereof that specifically binds to, or is immunologically reactive with a particular antigen, for example, EBV gp350/gp220, or a particular domain or fragment of gp350/gp220 such as AA1-101, 102-201, and 402-501.

In certain embodiments an antibody for use in the present methods or compositions is a full-length immunoglobulin molecule, which comprises two heavy chains and two light chains, with each heavy and light chain containing three complementary determining regions (CDRs). The CDRs of various antibodies are identified and listed in Table 1 below.

TABLE 1

| Antibodies | CDR Sequences | | | | | |
|---|---|---|---|---|---|---|
| | VH | | | VL | | |
| | CDR-1 | CDR-2 | CDR-3 | CDR-1 | CDR-2 | CDR-3 |
| m72A1 | GSSFTDY (SEQ ID NO: 4) | INPYNGG (SEQ ID NO: 20) | GGLRRVNWFAYW (SEQ ID NO: 36) | TGAVTTSNY (SEQ ID NO: 52) | GTN (SEQ ID NO: 68) | VLWHSNHWV (SEQ ID NO: 84) |
| h72A1 | GSSFTDY (SEQ ID NO: 4) | INPYNGG (SEQ ID NO: 20) | GGLRRVNWFAYW (SEQ ID NO: 36) | TGAVTTSNY (SEQ ID NO: 52) | GTN (SEQ ID NO: 68) | VLWHSNHWV (SEQ ID NO: 84) |
| HB-1 | GFLLTTY (SEQ ID NO: 5) | IWAGGS (SEQ ID NO: 21) | RDRGYGYLYAMDYW (SEQ ID NO: 37) | QNVGTN (SEQ ID NO: 53) | STD (SEQ ID NO: 69) | QQYNTYPYT (SEQ ID NO: 85) |
| HB-2 | GYTFTAY (SEQ ID NO: 6) | INYKTGE (SEQ ID NO: 22) | PYGYALDYW (SEQ ID NO: 38) | SSVNY* (SEQ ID NO: 54) | ATS* (SEQ ID NO: 70) | QQWSSNPPT* (SEQ ID NO: 86) |
| HB-3 | GYTFASY (SEQ ID NO: 7) | INPNNGH* (SEQ ID NO: 23) | RNLYYYGRPDYW* (SEQ ID NO: 39) | QDIGNY* (SEQ ID NO: 55) | YTS* (SEQ ID NO: 71) | QQGNTLPPT* (SEQ ID NO: 87) |
| HB-5 | GYTFTNH (SEQ ID NO: 8) | INPYNDY (SEQ ID NO: 24) | RSEGWLRRGAWFAY (SEQ ID NO: 40) | QSIGTS (SEQ ID NO: 56) | YAS (SEQ ID NO: 72) | QQSNSWPMLT (SEQ ID NO: 88) |
| HB-6 | GYTFTDY* (SEQ ID NO: 9) | INTRTGE (SEQ ID NO: 25) | PYGYALDYW (SEQ ID NO: 41) | SSVNY* (SEQ ID NO: 57) | ATS* (SEQ ID NO: 73) | QQWSSNPPT* (SEQ ID NO: 89) |
| HB-7 | GYTFTDY* (SEQ ID NO: 10) | ISPGRSG (SEQ ID NO: 26) | RYGHPSYLDVW (SEQ ID NO: 42) | QSVGNA (SEQ ID NO: 58) | SAS (SEQ ID NO: 74) | QQYSSYPLT (SEQ ID NO: 90) |
| HB-8 | GYSFTNY* (SEQ ID NO: 11) | INTYTGE (SEQ ID NO: 27) | RYYYGSVYSAWFAYW (SEQ ID NO: 43) | QSIVHSNGNTY* (SEQ ID NO: 59) | KVS* (SEQ ID NO: 75) | FQGSHVPYT* (SEQ ID NO: 91) |
| HB-9 | GFTFSSY (SEQ ID NO: 12) | ISSGGSY (SEQ ID NO: 28) | REDFYYGSSYGFFDVW (SEQ ID NO: 44) | QSIVHSNGNTY* (SEQ ID NO: 60) | KVS* (SEQ ID NO: 76) | FQGSHVPYT* (SEQ ID NO: 92) |
| HB-10 | GYTFTSY* (SEQ ID NO: 13) | INPSNGH (SEQ ID NO: 29) | RNLYYYGRPDYW (SEQ ID NO: 45) | QDIGNY* (SEQ ID NO: 61) | YTS* (SEQ ID NO: 77) | QQNTLPPT (SEQ ID NO: 93) |
| HB-11 | GDSITSG (SEQ ID NO: 14) | ISYSGS (SEQ ID NO: 30) | RGNGGNYDWYFDVW (SEQ ID NO: 46) | SSVNF (SEQ ID NO: 62) | YIS (SEQ ID NO: 78) | QQFTSSPSWT (SEQ ID NO: 94) |
| HB-12 | GYTFTNY* (SEQ ID NO: 15) | INPNNGH* (SEQ ID NO: 31) | RNLYYYGRPDYW* (SEQ ID NO: 47) | QSLVHSNGNTY (SEQ ID NO: 63) | KVS* (SEQ ID NO: 79) | SQSTHVPLT (SEQ ID NO: 95) |
| HB-14 | GYTFTDY* (SEQ ID NO: 16) | IHPRRGG (SEQ ID NO: 32) | RYGYPWYFDVW (SEQ ID NO: 48) | QSIVHDNGNTY (SEQ ID NO: 64) | KVS* (SEQ ID NO: 80) | FQGSHVPPT (SEQ ID NO: 96) |
| HB-17 | GYTFTSY* (SEQ ID NO: 17) | INPNNGH* (SEQ ID NO: 33) | RNLFYYSRPDYW (SEQ ID NO: 49) | QDIGNY* (SEQ ID NO: 65) | YTS* (SEQ ID NO: 81) | QQGNTLPPT* (SEQ ID NO: 97) |
| HB-20 | GYTFTSY* (SEQ ID NO: 18) | INPTNGH (SEQ ID NO: 34) | RNLYYYGRPDYW* (SEQ ID NO: 50) | QDIGNY* (SEQ ID NO: 66) | YTS* (SEQ ID NO: 82) | QQGNALPPT (SEQ ID NO: 98) |

TABLE 1-continued

CDR Sequences

| Anti-bodies | VH | | | VL | | |
|---|---|---|---|---|---|---|
| | CDR-1 | CDR-2 | CDR-3 | CDR-1 | CDR-2 | CDR-3 |
| HB-22 | GFSLTNY (SEQ ID NO: 19) | IWSDGS (SEQ ID NO: 35) | RNYYGNSYPAWFAYW (SEQ ID NO: 51) | QSIVHSNGNTY (SEQ ID NO: 67) | KVS* (SEQ ID NO: 83) | FQGSHVPWT (SEQ ID NO: 99) |

The term "antibody," in addition to natural antibodies, also includes genetically engineered or otherwise modified forms of immunoglobulins, such as synthetic antibodies, intrabodies, chimeric antibodies, fully human antibodies, humanized antibodies, peptibodies and heteroconjugate antibodies (e.g., bispecific antibodies, multispecific antibodies, dual-specific antibodies, anti-idiotypic antibodies, diabodies, triabodies, and tetrabodies). For example, humanized bispecific nAbs comprising E1 D1 and 72A1 targeting two EBV gps, gp350 and gH/gL complex, respectively, can be produced for use as a prophylactic agent against EBV infection or re-infection. In some embodiments, bispecific or multispecific antibodies comprising a combination of the mAbs identified herein or immunogenic fragments thereof can be produced. The bispecific or multispecific antibodies can be humanized according to known technologies. Alternatively, the bispecific or multispecific antibodies can be chimeric antibodies. The antibodies disclosed herein can be monoclonal antibodies or polyclonal antibodies. In those embodiments wherein an antibody is an immunologically active portion of an immunoglobulin molecule, the antibody may be, for example, a Fab, Fab', Fv, Fab' F(ab')2, disulfide-linked Fv, single chain Fv antibody (scFv), single domain antibody (dAb), or diabody. The antibodies disclosed herein, including those that are immunologically active portion of an immunoglobulin molecule, retain the ability to bind a specific antigen such as EBV gp350/220, or to bind a specific fragment of gp350/gp220 such as AA1-101, AA102-201, and AA402-501.

In some embodiments, the EBV antibodies disclosed herein have undergone post-translational modifications such as phosphorylation, methylation, acetylation, ubiquitination, nitrosylation, glycosylation, or lipidation associated with expression in a mammalian cell line, including a human or a non-human host cell. Techniques for producing recombinant antibodies and for in vitro and in vivo modifications of recombinant antibodies are known in the art.

Provided in certain embodiments herein are chimeric, and/or humanized EBV antibodies. Various techniques are known in the art for humanizing antibodies from non-human species such that the antibodies are modified to increase their similarity to antibodies naturally occurring in humans. Six CDRs are present in each antigen binding domain of a natural antibody. These CDRs are short, non-contiguous sequences of amino acids that are specifically positioned to form the antigen binding domain as the antibody assumes its three-dimensional configuration. CDR sequences of certain antibodies identified herein are shown in Table 1. The remainder of the amino acids in the antigen binding domains, referred to as "framework" regions, show less inter-molecular variability and form a scaffold to allow correct positioning of the CDRs. This disclosure also relates to antibodies comprising VH and VL regions comprising the CDRs shown in Table 1.

"Treating" or "treatment" of a disease or a condition may refer to preventing the disease or condition, slowing the onset or rate of development of the disease or condition, reducing the risk of developing the disease or condition, preventing or delaying the development of symptoms associated with the disease or condition, reducing or ending symptoms associated with the disease or condition, generating a complete or partial regression of the disease or condition, or some combinations thereof.

As used herein, the term "subject" refers to mammalian subject, preferably a human. The phrases "subject" and "patient" are used interchangeably herein.

The method for treating a condition or a viral infection includes administering a therapeutically effective amount of a therapeutic agent or a pharmaceutical composition. An "effective amount," "therapeutically effective amount" or "effective dose" is an amount of a composition (e.g., a therapeutic agent or a pharmaceutical composition) that produces a desired therapeutic effect in a subject, such as preventing or treating a target disease or condition, or alleviating symptoms associated with the disease or condition. The precise therapeutically effective amount is an amount of the composition that will yield the most effective results in terms of efficacy of treatment in a given subject. This amount will vary depending upon a variety of factors, including but not limited to the characteristics of the therapeutic agent (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy 21$^{st}$ Edition, Univ. of Sciences in Philadelphia (USIP), Lippincott Williams & Wilkins, Philadelphia, PA, 2005.

The pharmaceutical composition may include, among other things, one or more EBV antibodies disclosed herein or one or more immunogenic fragments thereof, one or more immunogenic peptides disclosed herein, or an EBV antibody-small molecule conjugate disclosed herein.

The pharmaceutical composition may also include one or more pharmaceutically acceptable carriers. A "pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

The pharmaceutical compositions described herein may be administered by any suitable route of administration. A route of administration may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. In some embodiments, the therapeutic compositions described herein are administered by intravenous injection or intraperitoneal injection.

In certain embodiments, disclosed herein is a method of treating or preventing EBV infection in a subject, comprising administering a therapeutically effective amount of one or more anti-gp350 antibodies disclosed herein or one or more immunogenic fragments thereof, one or more immunogenic peptides described herein, an EBV antibody-drug conjugate described herein, or a pharmaceutical composition comprising the anti-gp350 antibody or an immunogenic fragment thereof, one or more immunogenic peptides, or the EBV antibody-drug conjugate.

In certain embodiments, disclosed herein is a method of treating or preventing EBV infection in a subject, comprising administering a therapeutically effective amount of an anti-gp350 antibody disclosed herein or an immunogenic fragment thereof, an immunogenic peptide described herein, an EBV antibody-drug conjugate described herein, or a pharmaceutical composition comprising the anti-gp350 antibody or an immunogenic fragment thereof, one or more immunogenic peptides, or the EBV antibody-drug conjugate.

In certain embodiments, disclosed herein is a method of treating or preventing EBV-associated PTLD in a subject, comprising administering a therapeutically effective amount of an anti-gp350 antibody disclosed herein or an immunogenic fragment thereof, one or more immunogenic peptides described herein, an EBV antibody-drug conjugate described herein, or a pharmaceutical composition comprising the anti-gp350 antibody or an immunogenic fragment thereof, one or more immunogenic peptides, or the EBV antibody-drug conjugate, before or after the transplant in the subject.

As shown in the working examples, 15 novel EBV gp350-specific mAbs were generated, their binding to gp350 was characterized, their neutralization activity against EBV infection in vitro was determined, and their epitopes were mapped. The newly developed mAbs have many uses in vaccine development, diagnosis of viral infection, and therapeutic/prophylactic management of post-transplant lymphoproliferative diseases, either individually, in combination with nAb-72A1, or with other mAbs such as anti-gH/gL (E1D1).

To overcome the existing challenges facing PTLD treatment, novel EBV antibodies and EBV antibody-drug conjugates (ADCs) are developed. The EBV neutralizing antibodies (nAbs) that specifically block new or reactivated EBV infection are conjugated with small molecules that specifically target latent viral protein, EBV nuclear antigen 1 expressed in all EBV+ malignancies. The recent identification and isolation of nAbs against the highly variable viruses HIV-1 (10, 11), influenza (12-14), and respiratory syncytial virus (15) has direct implications for successful EBV protection. Indeed, in 2012, an international, multidisciplinary expert panel recommended use of intravenous (IV) anti-viral nAbs for preventing or treating EBV+ PTLD (16). EBV uses multiple surface glycoproteins (gps), including the major gp350, to infect host cells (17, 18). These gps are expressed on EBV virions and in EBV+ cells (19, 20), and stimulate immune responses in humans and in animal models (21-23), making them attractive targets for an EBV vaccine (24). Multiple lines of evidence suggest that use of anti-gp350 nAbs to protect against EBV-PTLDs is feasible (16): (A) Maternal Abs protect against EBV infection in neonates (25, 26); (B) gp350-expressing EBV+ cells activate complement (27) and mediate Ab-dependent cellular cytotoxicity (28); (C) gp350 vaccines reduce EBV load and protect against EBV+ lymphomas in marmosets (29-32) and protect EBV-naïve adults from EBV-induced mononucleosis (32-34); (D) Compared to control mice, SCID mice injected with peripheral blood mononuclear cells from EBV-naïve donors and immunized with anti-gp350 (72A1) mouse nAb are completely protected against EBV and development of EBV+ tumors or PTLD-like lesions (35); and (E) 72A1 also conferred short-term protection against acquiring EBV after transplantation in 3 out of 4 pediatric patients in a small phase 1 clinical trial (35). However, there was a major drawback: all 4 patients who received 72A1 developed human anti-mouse Abs (HAMA), which can cause side effects and limit treatment efficacy, with one developing a hypersensitivity reaction. This suggests that 72A1 in its native form is not a safe treatment for humans (35). Thus, chimeric (human/mouse), humanized, or human nAbs, which are safe and effective in the treatment of various cancers, are needed (7, 36-38).

Pre-existing antibodies provide the primary defense against viral infection. Prophylactic prevention of EBV primary infection has mainly focused on blocking the first step of viral entry by generating neutralizing antibodies (nAbs) that target EBV envelope glycoproteins. Five glycoproteins, in particular, gp350/220 (gp350), gp42, gH, gL, and gB, are required for efficient infection of permissible host cells and have emerged as potential prophylactic targets (23, 24, 61, 64).

Several studies have indicated that the EBV gp350 as the major immunodominant glycoprotein is an ideal target for EBV nAbs production. Although the ectodomain of EBV gp350 (AA 1-841) has been shown to contains at least seven unique CD21 binding epitopes located in the ectodomain of gp350 (58), at least one of these epitopes (AA 142-161) is capable of eliciting nAbs (57-58). The AA residues 142-161 are also one of the binding epitopes for nAb 72A1 (59, 68). The AA residues that constitute the other epitopes and their role in generating nAb has not been elucidated, as this information would be valuable in the precise design of effective EBV peptide vaccine. To date, nAb-72A1 remains the only EBV antibody with proven clinical prophylactic efficacy, as its been shown to confer short-term protection by reducing and delaying EBV infection onset in immunized pediatric transplant patients (35).

EBV predominantly infects epithelial cells and B cells, reflecting the viral tropism and the cellular ontogeny for EBV-associated malignancies (17). There are two schools of thought on how the initial EBV transmission into the human host occurs. In the first infection model, the incoming virus engages with ephrin receptor A2 via heterodimeric gH/gL, which triggers gB fusion with the epithelial cell membrane and entry of the virus into the cytoplasm (17). This interaction is thought to occur in the oral mucosa, where the virus undergoes lytic replication to release virions that subsequently infect B cells. In the alternative model, the incoming virus binds to the host cell via complement receptor type 1 (CR1)/CD35 (45) and/or CR2/CD21 through its major immunodominant glycoprotein, gp350 (65). The interaction between gp350 and CD35 and/or CD21 triggers viral adsorption, capping, and endocytosis into the B cell (66), which subsequently leads to interaction between heterotrimeric viral glycoproteins complex, gp42/gH/gL, binding to HLA class II molecules to activate gB membrane fusion and entry. Because these two models are not necessarily mutually exclusive, and given that both gp350 and gH/gL complex are important in initiating the first viral contact with host cells, use of nAbs that target either gp350 or gH/gL complex or both may potently block incoming virus at the oral mucosa.

Nearly all EBV-infected individuals develop nAbs directed to the ectodomains of these glycoproteins (52, 67). These antibodies can prevent neonatal infection, and can protect against acute infectious mononucleosis in adolescents and several human lymphoid and epithelial malignancies associated with EBV infection (30, 32-34). Although numerous monoclonal antibodies (mAbs) have been generated against EBV gp350 (53, 68, 69), only two murine mAbs, the non-neutralizing 2L10 and the neutralizing 72A1, have been extensively characterized and made commercially available (68, 69). Importantly, nAb-72A1 conferred short-term clinical protection against EBV transmission after transplantation in pediatric patients in a small phase I clinical trial (35).

EBV gp350 is the most immunogenic envelope glycoproteins on the virions. It is a type 1 membrane protein that encodes for 907 amino acid residues. A single splice of the primary transcript deletes 197 codons between codons 501 and 699, and joins two fragments of gp350 codons in frame to generate the gp220 messenger RNA. Both gp350 and gp220 are comprised of the same 18-AA residue at the C terminus that is located within the viral membrane, a 25-AA residue at the transmembrane-spanning domain, and a large highly glycosylated N-terminal ectodomain, AA 1-841 (57). The first 470 AA of gp350 are sufficient for binding CD21 in B cells, as demonstrated by a truncated gp350 (AA 1-470) blocking the binding of EBV to B cells and reducing viral infectivity (17). The gp350-binding domain on CD21 is mapped to N-terminal short consensus repeats (SCRs) 1 and 2, which also bind to a bioactive fragment of complement protein 3 (C3d) (34, 68). A soluble truncated EBV gp350 fragment (AA 1-470) and soluble CD21 SCR1 and SCR2 can block EBV infection and immortalization of primary B cells (57). However, gp350 binding to CD35 is not restricted to N-terminal SCRs; it binds long homologous repeat regions as well as SCRs 29-30 (57).

The gp350 ectodomain is heavily glycosylated, with both N- and O-linked sugars, which accounts for over half of the molecular mass of the protein. Currently there is only one crystal structure available for gp350, comprised of a truncated structure between 4-443 AA, with at least 14 glycosylated asparagine residues coating the protein with sugars, with the exception of a single glycan-free patch (59). Mutational studies of several residues in the glycan-free patch resulted in the loss of CD21 binding (59), suggesting that binding of CD35 and CD21 by gp350 is mediated within this region.

Using gp350 synthetic peptides binding to CD21 on the surface of a B cell line, additional gp350 epitope was identified in the C-terminal region of gp350 (AA 822-841), suggesting that this region is involved in EBV infection of B cells (58). The role of other epitopes in eliciting nAbs has not been fully investigated. Furthermore, the exact AA residues that comprise the core binding epitopes capable of eliciting neutralization and non-neutralization antibodies have not been determined. Mapping the EBV gp350 protein residues defining immunodominant epitopes, identifying the critical AA residues of the epitopes, and defining their roles in generating nAbs and non-nAbs will guide rational design and construction of an efficacious EBV gp350-based vaccine that would focus the B-cell responses to the protective epitopes.

As demonstrated in the working examples, 23 hybridomas producing antibodies against EBV gp350 were generated. To assess their clinical and diagnostic potential and utility in informing future prophylactic and therapeutic vaccine design: (1) the ability of the antibodies produced by the new hybridomas to detect gp350 protein was tested by enzyme-linked immunosorbent assay (ELISA), flow cytometry, and immunoblot; (2) the unique CDRs of the heavy and light chains of all 23 hybridomas were sequenced to identify novel mAbs; (3) the efficacy of each mAb to neutralize EBV infection in vitro was measured; and (4) competitive cell and/or linear peptide binding assays were used to identify gp350 regions recognized by neutralizing and non-neutralizing mAbs; and (5) peptide binding assays were used to identify gp350 core linear AA residues recognized by neutralizing and non-neutralizing mAbs.

Out of the 23 hybridomas, 15 were monoclonal and novel, based on their VH and VL CDR sequences, compared to the reported sequence of m72A1 (50). Following confirmation that the new 15 mAbs recognized gp350 antigen and contained unique VH-VL sequences, further characterization revealed that mAbs HB1, HB5, HB11, and HB20 inhibited EBV infection of a human B-cell line in a dose-dependent manner, with HB5 being the best neutralizer, comparable to m72A1 and h72A1. Thus, provided herein are four new nAbs against EBV infection of B cells with potential clinical utility in blocking viral infection in immunosuppression settings. The amino acid sequences of the heavy chain and light chain of the mAbs are provided in Table 2 below.

TABLE 2

Sequences of Heavy Chain and Light Chain

| | Heavy Chain | Light Chain |
|---|---|---|
| 72A1 | PELVKPGTSMKISCKASGSSFTDY<br>TMNWMKQSHGKNLEWIGLINPYNG<br>GTRYNQKFKGKATLTLDKSSSTAY | QAVLTQESALTTSPGETVTLTCRSST<br>GAVTTSNYANWVQEKPDHLFTGLIGG<br>TNNRVPGVPARFSGSLIGDKAALTIT |

TABLE 2-continued Sequences of Heavy Chain and Light Chain

| | Heavy Chain | Light Chain |
|---|---|---|
| | MEVLSLTSEDSAVYYCAGGLRRVN WFAYWGQGTLVSVSAAKTTPPSVY PLAPGSAAQTNSMVTLG (SEQ ID NO: 100) | GAQTEDEAIYFCVLWHSNHWVFGGGT KLTVL (SEQ ID NO: 101) |
| HB1 | PGLVAPSQSLSITCTVSGFLLTTY GVHWVRQPPGKGLEWLGVIWAGGS TNYNSALMSRLSINKDISKSQVFL KMNSLQTDDTAMYYCTRDRGYGYL YAMDYWGQGTSVTVSSAKTTPPSV YPLAPGSAAQTNSMVTLG (SEQ ID NO: 102) | KFMSTSVGDRVSVTCKASQNVGTNVA WYQQKPGQSPKALIYSTSSRYTGVPD RFAGSGSGTDYTLTISNVQSEDLAEY FCQQYNTYPYTFGGGTRLDIKRADAA PTV (SEQ ID NO: 103) |
| HB2 | PELKKPGETVKISCKASGYTFTAY SMHWVKLTPGKGLKWMGWINTKTG EPTYADDFKGRFAFSLETSASTAY LQINNLKNEDTATYFCAPYGYALD YWGQGTSVTVSSAKTTPPSVYPLA GPSAAQTNSMVTLG (SEQ ID NO: 104) | AILSASPGEKVTMTCRATSSVNYMHW YQQKPGSSPKPWIYATSNLASGVPAR FSGSGSGTSYSLTISRVEAEDAATYY CQQWSSNPPTFGAGTKLELKRADAAP TV (SEQ ID NO: 105) |
| HB3 | AELVRPGASVKLSCKASGYTFASY WMQWVKQWPGQGLEWIGEINPNNG HTNYNERFKNKASLTVDKSSSTAY MQLSSLTSEDSAVYYCARNLYYYG RPDYWGQGTSVTVSSAKTTAPSVY PLAPVCGDTTGSSVTLG (SEQ ID NO: 106) | SSLSASLGDRVTISCRASQDIGNYLN WYQQKPDGTIKLLIYYTSRLHSGVPS RFSGSGSGTDYSLTISNLEEEDIATY FCQQGNTLPPTFGGGTKLEIKRADAA PTV (SEQ ID NO: 107) |
| HB5 | AELVRPGASVKISCKAFGYTFTNH NINWVKQRPGQGLDWIGYINPYND YTSYNQKFKGKATLTVDKSSNTAY MELSSLTSEDSAVYYCARSEGWLR RGAWFAYWGQGTLVTVSAAKTTAP SVYPLAPVCGDTTGSSVTLG (SEQ ID NO: 108) | AILSVSPGERVSFSCRASQSIGTSIH WYQQRTNDSPRLLIKYASESISGIPP RFSGSGSGTDFTLSINSVESEDIADY HCQQSNSWPMLTFGAGTKLELKRADA APTV (SEQ ID NO: 109) |
| HB6 | PELRKPGETVKISCKASGYTFTDY SMHWVKQTPGKGLKWMGWINTRTG EPRYADDFKGRFAFSLETSASTAY LQINNLKNEDTATYFCAPYGYALD YWGQGTSVTVSSAKTTPPSVYPLA PGSAAQTNSMVTLG (SEQ ID NO: 110) | AILSASPGEKVTMTCRATSSVNYMHW YQQKPGSSPKPWIYATSNLASGVPAR FSGSGSGTSYSLTISRVEAEDAATYY CQQWSSNPPTFGAGTKLELKRADAAP TV (SEQ ID NO: 111) |
| HB7 | AELVRPGASVKLSCKALGYTFTDY EMHWVKQTPVHGLEWIGTISPGRS GTAYNQKFKGKATLTADKSSRTAY MELNSLTSEDSAVYYCSRYGHPSY LDVWGAGTTVTVSSAKTTPPSVYP LAPGSAAQTNSMVTLG (SEQ ID NO: 112) | KFMSTSVGDRVNITCKASQSVGNAVA WFQQKPGQSPKLLIYSASNRYTGIPD RFTGSGSGTDFTLTCNNMQSEDLADY FCQQYSSYPLTFGAGTKLELKRADAA PTV (SEQ ID NO: 113) |
| HB8 | PELKKPGETVKISCKASGYSFTNY GMNWVKQAPGKGLKWMGWINTYTG EPTYADDFKGRFAFSLETSASTAF LQINNLKNEDTATYLCARYYYGSV YSAWFAYWGQGTLVTVSSAKTTPP SVYPLAPGSAAQTNSMVTLG (SEQ ID NO: 114) | LSLPVSLGDQASISCRSSQSIVHSNG NTYLEWYLQKAGQSPKLLIYKVSNRF SGVPDRFGGSGSGTDFTLKISRVEAE DLGVYYCFQGSHVPYTFGGGTKLEIK RADAAPTV (SEQ ID NO: 115) |
| HB9 | GGLVKPGGSLKLSCAASGFTFSSY TMSWVRQTPEKRLEWVATISSGGS YIYYPDSVKGRFTISRDNAKNTLY LQMSSLKSEDTAIYYCTREDFYYG SSYGFFDVWGAGTTVTVSSAKTTA PSVYPLAPVCGDTTGSSVTLG (SEQ ID NO: 116) | LSLPVSLGDQASISCRSSQSIVHSNG NTYLEWYLQKAGQSPKLLIYKVSNRF SGVPDRFGGSGSGTDFTLKISRVEAE DLGVYYCFQGSHVPYTFGGGTKLEIK RADAAPTV (SEQ ID NO: 117) |
| HB10 | AELVRPGASVKLSCKASGYTFTSY WMHWVKQWPGQGPEWIGEINPSNG HTNYNERFKNKATLTVDKSSSTAY MQLSSLTSEDSAVYYCARNLYYYG RPDYWGQGTSVTVSSAKTTPPSVY PLAPGSAAQTNSMVTLG (SEQ ID NO: 118) | SSLSASLGDRVTISCRASQDIGNYLN WYQQKPDGTVKLLIYYTSRLHSGVPS RFSGSGSGTDYSLTISNLEEEDIATY FCQQGNTLPPTFGGGTKLEIKRADAA PTV (SEQ ID NO: 119) |

TABLE 2-continued

Sequences of Heavy Chain and Light Chain

| | Heavy Chain | Light Chain |
|---|---|---|
| HB11 | PSLVKPSQTLSLTCSVTGDSITSG FWNWIRKFPGNKLEYMGYISYSGS TYYNPSLKSRISITRDTSKNQYYL QLNSVTTEDTATYYCARGNGGNYD WYFDVWGAGTTVTVSSAKTTPPSV YPLAPGSAAQTNSMVTLG (SEQ ID NO: 120) | AIMSASLGEKVTMSCRASSSVNFMNW YQQKSDDSPKLLIYYISNLAPGVPAR FSGSGSGNSYSLTISGMEGEDAATYY CQQFTSSPSWTFGGGTKLEIKRADAA PTV (SEQ ID NO: 121) |
| HB12 | AELVRPGASVKLSCKASGYTFTNY WIHWVKQWPGQGLEWIGEINPNNG HTNYNERFKNKASLTVDKSSSTAY MQLSSLTSEDSAVYYCARNLYYYG RPDYWGQGTSVTVSS (SEQ ID NO: 122) | LSLPVSLGDQASISCRSSQSLVHSNG NTYLHWYLQKPGQSPKLLIYKVSNRF SGVPDRFSGSGSGTDFTLKISRVEAE DLGVYFCSQSTHVPLTFGSGTKLEIK (SEQ ID NO: 123) |
| HB14 | SGAELVRPGASVNLSCKALGYTFT DYEMHWVKQTPVYGLEWIGTIHPR RGGTAYNQRFKGKAALTADKSSST AYMELSSLTSEDSAVYYCARYGYP WYFDVWGAGTTVTVSS (SEQ ID NO: 124) | LSLPVSLGDQASISCRSSQSIVHDNG NTYLEWYLQKPGQSPKLLIYKVSNRF SGVLDKFSGSGSGTDFTLKISRVEAE DLGIYYCFQGSHVPPTFGGGTKLEIK (SEQ ID NO: 125) |
| HB17 | AELVIPGASVKVSCKASGYTFTSY WIHWVKQWPGQGLEWIGEINPNNG HTNYNEKFKSKATLTVDKSSSTAY MQLSSLTSEDSAVYYCARNLFYYS RPDYWGQGTSVTVSSAKTTPPSVY PLAPGCGDTTGSSVTLG (SEQ ID NO: 126) | SSLSASLGDRVTISCRASQDIGNYLN WYQQKPDGTIKLLIYYTSRLHSGVPS RFSGSGSGTDYSLTISNLEEEDIATY FCQQGNTLPPTFGGGTKLEIKRADAA PTV (SEQ ID NO: 127) |
| HB20 | AELVKPGASVKLSCKASGYTFTSY WIQWVKQRPGQGLEWIGEINPTNG HTNYNEKFKTKATLTVDKSSSTAY MRLSSLTSEDSAVYYCARNLYYYG RPDYWGQGTSVTVSSAKTTAPSVY PLAPVCGDTTGSSVTLG (SEQ ID NO: 128) | SSLSASLGDRVTISCRASQDIGNYLN WYQQKPDGTVKLLIYYTSRLHSGVPS RFSGSGSGTDYSLTISNLEQEDIATY FCQQGNALPPTFGGGTKLEIKRADAA PTV (SEQ ID NO: 129) |
| HB22 | PGLVAPSQSLSITCTVSGFSLTNY GIHWVRQPPGKGLEWLVVIWSDGS TIYNSALKSRLSISKDNSKSQVFL KMNSLQTDDTAMYYCARNYYGNSY PAWFAYWGQGTLVTVSAAKTTPPS VYPLAPGSAAQTNSMVTLG (SEQ ID NO: 130) | LSLPVSLGDQASISCRSSQSIVHSNG NTYLEWYLQKPGQSPKLLIYKVSNRF SGVPDRFSGSGSGTDFTLRISRVEAE DLGVYYCFQGSHVPWTFGGGTKLEIK RADAAPTV (SEQ ID NO: 131) |

The identification of four new potent nAbs (HB1, HB5, HB11 and HB20) and sequencing of their CDR regions, as well as the humanization of m72A1 and E1D1, opens the possibility of using these nAbs for clinical applications, such as reducing or preventing EBV infection in transplant settings, with the consequent potential to reduce the incidence of EBV+ PTLDs. The h72A1 IgG1 antibody recognized both native gp350 as well as gp350 peptides that constitute the principal gp350 neutralizing epitope (142-161) and completely eliminated anti-murine IgG immunoreactivity. Importantly, h72A1—and the four newly generated nAbs (HB1, HB5, HB11, and HB20)—significantly blocked in vitro EBV infection of B cells to a degree comparable to or better than m72A1. Combining two or more nAbs that bind to different peptides on gp350 and gH/gL can significantly reduce infection in both B cells and epithelial cells.

In addition, both nAbs and non-nAbs can be used as research tools to provide insight into epitope targets important for vaccine development. In the past, various methods, including lectin/ricin immune-affinity assay, purified mAbs, purified soluble gp350 mutants, synthetic peptides, cell binding assays, and X-ray crystallography of partial gp350 protein (AA 4-443), have been used to identify the critical gp350 epitopes responsible for its interaction with the CD21 and CD35 cellular receptors (summarized in Table 3). Despite several attempts to identify gp350 epitopes important for eliciting nAbs, to date only a single epitope, AA 142-161, has been identified, which is also the binding epitope for nAb 72A1. Currently, the lack of a crystal structure of full-length gp350 protein and the unavailability of multiple nAbs hinder the opportunity to identify other gp350 epitopes that might elicit nAbs and inform design of effective vaccine strategies. To identify gp350 epitopes responsible for eliciting nAbs, the newly generated nAbs (HB1, HB5, HB11, and HB20) and non-nAbs (HB10, HB17, and HB22) were used to perform competitive cell binding and ELISA-based linear peptide binding assays. Although both approaches have various limitations, they offer useful information that when combined might inform and/or advance vaccine development efforts. Competitive cell binding assays can provide information on whether two antibodies bind overlapping or non-overlapping epitopes, although they are unable to indicate whether the competing antibodies bind the same or nearby epitopes, nor identify actual AA residues involved in the binding. On the other hand, the ELISA peptide binding assay is only reactive to linear epitopes and may or may not take into consideration post-translational protein modifications, depending on whether a full protein or peptides are used as the target antigen(s).

Using biotinylated antibodies, it was shown that the newly generated gp350 nAbs (HB1, HB5, HB11, and HB20) bound targets that overlapped with those of both m72A1 and h72A1, although HB20 showed only partial binding to the overlapping targets. The non-Ab, HB17 showed little to no competitive binding when compared to nAbs, suggesting that they bound different gp350 epitopes. These results strongly suggest that two distinct binding regions have been identified, one bound predominantly by nAbs and the other by non-nAbs, and that nAbs potentially bind targets within the same proximity, if not the same AA sequences. Thus, the current antibodies provide the first step toward generating reagents required for mapping neutralizing versus non-neutralizing epitopes on gp350, should the full-length crystal structure of the protein remain unavailable. Using linear peptide epitope mapping, three major mAb-binding regions, 1-101, 102-201, and 402-501 were identified; all three regions incorporable previously identified linear epitopes (58, 51, 56). Regions 1-101 and 402-501 were bound by both nAbs and non-nAbs, suggesting that these regions are immunodominant. However, the 102-201 region containing the nAb epitope 142-161 was only bound by nAbs (HB5, HB11, HB20, and both m72A1 and h72A1), with the exception of the nAb HB1. These results suggest that epitopes/regions capable of eliciting nAbs are located within the N-terminus of gp350.

Previous studies have generated and characterized several anti-gp350 mAbs, both neutralizing and non-neutralizing. Some of these have been effectively used to map the immunodominant or neutralizing epitopes present in the gp350 ectodomain, which has relevance for future strategies to design sterilizing prophylactic vaccines (Table 3).

TABLE 3

Summary of published gp350 epitope mapping using various methodologies

| Method | mAbs/protein/peptides | Number of epitopes identified | Reference |
|---|---|---|---|
| Competitive binding assay | mAbs | 7 epitopes - Sequence not defined | (53) |
| Binding studies: Determine the effects of anti-gp350 mAbs on gp350 binding to CR2 | mAbs | 2 possible regions identified by sequence alignment to C3d sequence: 1. aa 21-28 2. aa 372-378 | (54) |
| Peptide digest and immunoprecipitation | Truncated and mutant protein; mAbs (72A1 and BOS-1) | Narrowed down to the first 470 residues | (57) |
| Binding studies | Peptide and protein | 2 sequences defined: 1. aa 21-28 2. N-terminus of gp350 | (55) |
| Dot Blot immunoassay: Purified truncated protein incubated with mAbs | Protein - 8 clones overlapping N- and C- terminal portions of protein; mAbs from Qualtiere et al., 1987 | 3 sequences defined: 1. aa 310-325 2. aa 326-439 3. aa 733-841 | (56) |
| Peptide cell binding assay to 2 CR2-positive (Raji and Ramos) and 1 -negative (P3HR-1) cell lines | Synthesized peptides covering gp350 (907 aa) | 7 regions, 3 identified: 1. aa 142-161 2. aa 282-301 3. aa 822-841 | (58) |
| Crystal structure and binding studies | Mutant proteins; mAbs 72A1 | 3 epitopes (based on 72A1 binding and gp350 4-443) 1. aa 16-29 2. aa 142-161 3. aa 282-301 | (59) |
| Structural docking studies and antigenicity mapping | gp350 and CR2 crystal structure alignment/docking | Single epitope (based on gp350 aa 1-470) 1. aa 147-165 | (60) |
| Structural alignment: computer modeling of gp350 and 72A1 and docking studies | Peptides (used in immunization); mAb (72A1) | 4 epitopes: identified 1. aa 14-20 2. aa 144-161 3. aa 194-211 4. aa 288-291 | (51) |

Virus-specific treatments are less likely to target basic metabolic mechanisms of healthy cells, making them more likely to efficiently kill virus-infected cells with fewer side effects. Until recently, few drug regimens have specifically targeted EBV+ lymphomas. However, in 2015, a few small molecules showed activity against EBV-transformed cells (39). Furthermore, in 2017, Jiang et al. described a novel small molecule ($L_2P_4$) that shows discriminating anti-proliferative activities against EBV-transformed B lymphoma cells (40).

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLES

Example 1: Materials and Methods

Cells and viruses.

AGS-EBV-eGFP, a human gastric carcinoma cell line infected with a recombinant Akata virus expressing enhanced fluorescent green protein (eGFP) was a kind gift of Dr. Lisa Selin (University of Massachusetts Medical School). Anti-EBV gH/gL (E1D1) hybridoma cell line was a kind gift of Dr. Lindsey Hutt-Fletcher (Louisiana State University Health Sciences Center). Chinese hamster ovary cells (CHO); human embryonic kidney cells expressing SV-40 T antigen (HEK-293T); HEK-293 6E suspension cells; EBV-positive Burkitt lymphoma cells (Raji); myeloma cells (P3X63Ag8.653); and anti-EBV gp350 nAb-72A1 hybridoma cells (HB168) were purchased from American Type Culture Collection (ATCC). ExpiCHO cells were purchased from ThermoFisher Scientific.

AGS-EBV-eGFP cells were maintained in Ham's F-12 media supplemented with 500 µg/ml neomycin (G418, Gibco). Raji, P3X63Ag8.653, and HB168 hybridoma cells were maintained in RPMI 1640. CHO and HEK-293T cells were maintained in DMEM. HEK-293 6E cells and ExpiCHO cells were maintained in FreeStyle F17 Expression Medium supplemented with 0.1% Pluronic F-68 and Gibco ExpiCHO Expression Media, respectively. All culture media were supplemented with 10% fetal bovine serum (FBS) from Millipore Sigma, 2% penicillin-streptomycin, and 1% I-glutamine, with the exception of Freestyle F17 expression medium and Gibco ExpiCHO Expression Media. All media were purchased from ThermoFisher Scientific unless otherwise specified.

Antibodies and Plasmids.

Primary antibodies: EBV anti-gp350 nAb (m72A1) and anti-gH/gL (E1D1) were purified from the supernatant of HB168 and E1D1 hybridoma cell lines, respectively, using Capturem™ Protein A Maxiprep spin columns (Takara) or protein G affinity and size-exclusion chromatography. The non-nAb anti-gp350/220 mAb (2L10) was purchased from Millipore Sigma. Anti-KSHV gH/gL 54A1 mAb was generated and characterized as previously disclosed (79).

Secondary antibodies: Horseradish peroxidase (HRP)-conjugated goat anti-mouse IgG for immunoblot or ELISA were purchased from Bio-Rad. HRP-conjugated goat anti-human IgG for ELISA was purchased from ThermoFisher Scientific. Alexa Fluor (AF) 488-conjugated goat anti-mouse IgG (H+L) for flow cytometry was purchased from Life Sciences Tech. Goat anti-mouse IgG (H+L) secondary antibody and DyLight 650 for epitope mapping were purchased from Thermo Fisher Scientific. Anti-biotin monoclonal antibody conjugated to AF488 for competitive binding assay was purchased from ThermoFisher Scientific.

The construction of the pCI-puro vector and pCAGGS-gp350/220-F has been described (23, 45).

Virus Production and Purification.

eGFP-tagged EBV was produced from the EBV-infected AGS cell line as described (46). Briefly, AGS-EBV-eGFP cells were seeded to 90% confluency in T-75 flasks in Ham's F-12 medium containing G418 antibiotic. After the cells reached confluency, G418 media was replaced with Ham's F-12 medium containing 33 ng/ml 12-O-tetradecanoylphorbol-13-acetate (TPA) and 3 mM sodium butyrate (NaB) to induce lytic replication of the virus. Twenty-four hours post-induction, the media was replaced with complete Ham's F-12 media without G418, TPA, or NaB and cells were incubated for 4 days at 37° C. in a 50% $CO_2$ incubator. The cell supernatant was collected, centrifuged, and filtered using 0.8 µm filter to remove cell debris. The filtered supernatant was ultra-centrifuged using a Beckman-Coulter type 19 rotor for 70 min at 10,000 rpm to pellet the virus. EBV-eGFP virus was titrated in both HEK-293T cells and Raji cells, and stocks were stored at −80° C. for subsequent experiments.

Generation and Purification of Gp350 Virus-Like Particles.

To generate gp350 VLPs, equal amounts (8 µg/plasmid) of the relevant plasmids (pCAGGS-Newcastle disease virus (NDV) matrix (M), and nucleocapsid proteins (NP), and gp350 ectodomain fused to NDV fusion (F) protein cytoplasmic and transmembrane domains) were co-transfected into 80% confluent CHO cells seeded in T-175 $cm^2$ flasks; supernatant from transfected cells containing VLPs was collected and VLPs were purified and composition characterized as previously described (47).

Production of Hybridoma Cell Lines.

Seven days prior to immunization, two eight-week-old BALB/c mice were bled for collection of pre-immune serum. The mice were immunized with purified UV-inactivated EBV three times (Day 0, 21, and 35), and then boosted every 7 days three times (Day 42, 49, and 56) with VLPs incorporating gp350 on the surface after Day 35. The mice were sacrificed, and their splenocytes were isolated, purified, and used to fuse with P3X63Ag8.653 myeloma cells at a ratio of 3:1 in the presence of polyethylene glycol (PEG, Sigma). Hybridoma cells were seeded in flat-bottom 96-well plates and selected in specialized hybridoma growth media with HAT (Sigma) and 10% FBS as previously described (80).

Indirect ELISA.

Hybridoma cell culture supernatant from wells that had colony-forming cells were tested for antibody production by indirect ELISA. Briefly, immunoplates (Costar 3590; Corning Incorporated) were coated with 50 µl of 0.5 µg/ml recombinant EBV gp350 ectodomain (Immune Technology Corporation) diluted in 1× phosphate buffered saline (PBS, pH 7.4) and incubated overnight at 4° C. After washing three times with 1×PBS containing 0.05% (v/v) Tween 20 (washing buffer), plates were blocked with 100 µl washing buffer containing 2% (w/v) bovine serum albumin (BSA) (blocking buffer) then incubated for 1 h at room temperature and washed as above. 100 µl of hybridoma supernatant or 50 µl of 10 µg/ml purified mAbs was added to each well (in triplicate) and incubated for 2 h at room temperature. Anti-KSHV gH/gL 54A1 and m72A1 mAbs were added as negative and positive controls, respectively. The plates were washed as described above, followed by incubation with 50 µl of goat anti-mouse IgG HRP-conjugated secondary antibody (1:2,000 diluted in 1×PBS) at room temperature for 1 h. The plates were washed again and 100 µl of chromogenic substrate 2,2'-azino-bis (3-ethylbenzothiazoline-6-sulphonic acid) (ABTS, Life Science Technologies) was added. The reaction was stopped using 100 µl of ABTS peroxidase stop solution containing 5% sodium dodecyl sulfate (SDS) in water. The absorbance was read at an optical density of 405 nm using an ELISA reader (Molecular Devices). All experiments were performed in triplicate and confirmed in three independent experiments.

Antibody Purification, Quantification, and Isotyping.

Hybridoma cells from selected individual positive clones were expanded stepwise from 96-well plates to T-75 flasks. At confluence in T-75 flasks, supernatant from individual clones was collected, clarified by centrifugation (4,000 g, 10 min, 4° C.), and filtered through a 0.22-µm membrane filter (Millipore). Antibodies were further purified by Capturem™ Protein A Maxiprep (Takara) and stored in 1×PBS (pH 7.4) at 4° C. Alternatively, antibodies were purified using protein G affinity chromatography followed by size-exclusion chromatography at the Beckman Institute of City of Hope X-ray Crystallography Core facility. Antibodies were analyzed by SDS-PAGE to determine purity. Bicinchoninic acid assay (BCA assay; Thermo Fisher Scientific) was conducted to determine the concentration of purified antibodies. Isotype identification was performed with the Rapid ELISA mouse mAb isotyping kit (Thermo Fisher Scientific). Two independent experiments were performed.

RNA Extraction, cDNA Synthesis, and Sequencing and Analysis of the Variable Region of the mAbs.

Total RNA was extracted from $1\times10^6$ hybridoma cells using the RNeasy Mini Kit (Qiagen). Each hybridoma clone cDNA was synthesized in a total volume of 20 µl using Tetro Reverse Transcriptase (200 u), RiboSafe RNase Inhibitor, Oligo(dT)18 primer, dNTP mix (10 mM each nucleotide), and 100-200 ng RNA. Reverse transcription was performed at 45° C. for 30 min, and terminated at 85° C. for 5 min. The cDNA was stored at −20° C. Immunoglobulin (Ig) VH and VL were amplified using the mouse Ig-specific primer set purchased from Novagen (48). The VH and VL genes were amplified in separate reactions and PCR products were visualized on 1% agarose gel.

The VH and VL amplicons were sequenced using an Illumina MiSeq platform: duplicate 50 µl PCR reactions were performed, each containing 50 ng of purified cDNA, 0.2 mM dNTPs, 1.5 mM $MgCl_2$, 1.25 U Platinum Taq DNA polymerase, 2.5 µl of 10×PCR buffer, and 0.5 µM of each primer designed to amplify the VH and VL. The amplicons were purified using an AxyPrep Mag PCR Clean-up kit (Thermo Fisher Scientific). The Illumina primer PCR PE1.0 and index primers were used to allow multiplexing of samples. The library was quantified using ViiA™ 7 Real-Time PCR System (Life Technologies) and visualized for size validation on an Agilent 2100 Bioanalyzer (Agilent Technologies) using a high-sensitivity cDNA assay. The sequencing library pool was diluted to 4 nM and run on a MiSeq desktop sequencer (Illumina). The 600-cycle MiSeq Reagent Kit (Illumina) was used to run the 6 pM library with 20% PhiX (Illumina), and FASTQ files were used for data analysis (81). The determination of immunoglobulin families was analyzed using the IMGT/V-QUEST tool 210 (www.imgt.org/IMGT_vquest/vquest) (82).

Chimeric mAb Construct Generation.

To generate chimeric mAbs, the VH and VL sequences were cloned into the dual-vector system such as pFUSE CHIg/pFUSE CLIg (InvivoGen), which express the constant region of the heavy and light chains of human immunoglobulins, respectively (Genewiz). The constructs were transiently transfected into HEK-293 6E cells. The supernatants were collected at 72 h post-transfection and IgG was purified using protein A/G affinity chromatography.

Humanization of 72A1.

To generate humanized mAbs, the BioLuminate interface (Schrödinger) was used to identify the human VH and VL framework using 72A1. The resulting model was visually inspected to ensure appropriate packing at the base of the CDR. The sequence was meditope-enabled to add functionality for generating bispecific antibodies in the future (83). The resulting sequences were codon-optimized, synthesized, and cloned into the PD2610 vector (Atum). The constructs were transiently transfected into ExpiCHO cells following the manufacturer's protocol. Supernatant was collected at 10 days post-transfection and IgG was purified using protein G affinity chromatography, followed by size-exclusion chromatography.

Immunoblot Analysis.

CHO cells were cultured and stably co-transfected with full-length pCAGGS-gp350/220 and pCI-puro vector containing a puromycin resistance gene. Forty-eight hours post-transfection, DMEM media containing 10 µg/ml of puromycin was added to enrich for cells expressing gp350 protein. Puromycin-resistant clones were expanded, followed by flow cytometry sorting using m72A1 to a purity >90%. EBV gp350-positive CHO cells were harvested and lysed in radioimmunoprecipitation assay buffer (RIPA) followed by centrifugation at 15,000 g for 15 min on a benchtop centrifuge. The lysate was collected and heated at 95° C. for 10 min in SDS sample buffer containing β-mercaptoethanol, then separated using SDS-PAGE. Proteins were transferred onto a nitrocellulose membrane using an iBlot™ Transfer System (Thermo Fisher Scientific) followed by incubation in blocking buffer (1% BSA; 20 mM Tris-HCl, pH 7.5; 137 mM NaCl; and 0.1% Tween-20 [TBST]) for 1 hour. The blots were incubated in TBST containing purified anti-gp350 antibodies (1:50) overnight at 4° C. After three washes with TBST, the blots were incubated with HRP-conjugated goat anti-mouse (1:2000) in TBST for 1 hour. After three washes, the antibody-protein complexes were detected using the Amersham ECL Prime Western Blotting Detection Reagent (GE Healthcare). All experiments were independently repeated three times.

Flow Cytometry.

To assess the ability of purified anti-gp350 mAb to detect surface expression of EBV gp350 protein by flow cytometry, CHO cells that stably express EBV gp350 were harvested and stained with purified anti-gp350 (10 µg/ml), followed by AF488 goat anti-mouse IgG secondary antibody. Flow cytometric analysis was performed on a C-6 FC (BD Biosciences) and data was analyzed using FlowJo Cytometry Analysis software (FlowJo, LLC) as described (47). All the experiments were independently repeated three times.

EBV Neutralization Assay.

EBV neutralization assay was performed in Raji cells as previously described (47). Briefly, purified individual anti-gp350 mAbs were incubated with purified AGS-EBV-eGFP (titer calculated to infect at least 8% of HEK293 cells seeded in 100 µl of serum-free DMEM) for 2 hours at 37° C. To represent EBV infection of B cells, the pre-incubated anti-gp350 mAbs/AGS-EBV-eGFP were used to infect $5\times10^5$ Raji cells seeded in a 96-well plate for 2 hours at 37° C. Neutralizing 72A1 and non-neutralizing 2L10 anti-gp350 mAbs served as positive and negative controls, respectively. Infected cells were washed three times with PBS to remove any unbound viruses and antibodies. Washed, infected cells were incubated in 96-well plates at 37° C. for 48 hours post-infection and the number of eGFP+ (infected) cells was determined using flow cytometry. All dilutions were performed in quintuplicate and the assays were repeated three times. Antibody EBV neutralization activity was calculated as: % neutralization=(EBValone−EBVmAb)/(EBValone)×100.

Epitope Mapping by Competitive Cell Binding Assay.

To evaluate conformation epitope mapping of the selected mAbs, competitive binding assays were conducted using biotinylated mAbs. A one-step antibody biotinylation kit (MACS Miltenyi Biotec) was used to biotinylate the mAbs. Approximately $1\times10^5$ CHO cells that stably expressed EBV gp350 were incubated for 2 hours with serially diluted (500, 250, 125, and 67.5 µg/ml) unlabeled competitor mAbs and non-specific anti-KSHV gH/gL 54A1 mAb. After being washed with PBS, the cells were incubated for 2 hours in the presence of 1 μg/ml biotinylated mAbs. To determine maximum binding, cells in which the biotinylated mAb was added in the absence of unlabeled mAbs were included in the assay. Cells were washed with PBS, followed by incubation for 1 hour with anti-biotin AF488 at a dilution of 1:500. After the final wash in PBS, cells were resuspended in 1% paraformaldehyde and analyzed by flow cytometry as described above. Percentage of inhibition was calculated as: 100−[(% fluorescent cells with competitor mAb/% fluorescent cells without competitor mAb)×100]. The complete prevention of binding of a biotinylated mAb by its unlabeled counterpart was used as a validation of the assay, as previously described (84).

Synthesis of 20-Mer Linear Peptides of Gp350 Proteins.

Forty-five sequential 20-mer linear peptides, covering the whole sequence of gp350 (GenBank: NC_007605.1), with an exception of aa 862-881, were synthesized using a solid phase method and cleaved using a low-high hydrogen fluoride method by the GenicBio, as previously described (58). Synthesis of aa 862-881 (pep-44) was not possible due to multiple hydrophobic aa.

Linear Epitope Mapping by Peptide-mAb Binding Assay.

The binding of anti-gp350 mAbs to 45 synthesized 20-mer sequential peptides covering the total length of gp350 was analyzed using indirect ELISA as described (58). Briefly, immunoplates were coated with 50 μl of 10 μg/ml EBV gp350 peptides (forty-five 20-mers) diluted in PBS and incubated overnight at 4° C.; 0.5 μg/ml recombinant EBV gp350 ectodomain protein was used as a positive control. After washing three times with washing buffer (PBS containing 0.05% (v/v) Tween 20), plates were blocked with 100 μl washing buffer containing 3% BSA (blocking buffer), incubated for 1 hour at room temperature, and washed as above. Ten μg/ml purified mAbs were added to each well in triplicate and incubated for 2 hours at room temperature. Anti-gp350 antibodies m72A1 and h72A1 were added as positive controls and anti-KSHV-gH/gL 54A1 mAb was used as negative control. The plates were washed as described above, followed by incubation with goat anti-mouse IgG or goat anti-human IgG HRP-conjugated secondary antibody (1:2,000 diluted in PBS) at room temperature for 1 hour. The plates were washed again and the chromogenic substrate ABTS was added. The reaction was stopped using ABTS peroxidase stop solution. The absorbance was read at an optical density of 405 nm using an ELISA plate reader.

Statistical Analysis.

Unpaired Mann-Whitney U test was used to assess statistical differences between two independent groups. Statistical calculations were performed in Graphpad Prism. Data was considered statistically significant at $p<0.05$.

Example 2: Novel Anti-Gp350 mAbs Target Linear and Conformational Epitopes

New EBV gp350-specific mAbs were generated and biochemically characterized, and their ability to neutralize EBV infection was evaluated. In addition, the antibodies were used to map immunodominant epitopes on the EBV gp350 protein. 23 novel monoclonal antibodies specific against EBV gp350 were developed. To generate hybridomas, BALB/c mice were immunized three times with purified UV-inactivated EBV and boosted three times with virus-like particles (VLPs) that incorporate EBV gp350 ectodomain (1-841) on the surface to improve antibody affinity maturation and avidity. Then the splenocytes were isolated from the immunized mice and fused with myeloma cells to generate hybridomas. Specifically, five eight-week-old BALB/c mice were immunized with virus-like particles incorporating gp350/220 on the surface, four times (day 0, 14, 28, and 56) via intraperitoneal injection without adjuvants. At day 64, immunized mice were boosted once intravenously. Animals were sacrificed at Day 70 to harvest splenocytes for fusion with the mouse myeloma P3X63Ag8 cell line.

Indirect ELISA was used to screen supernatants from the hybridomas for specificity against purified EBV gp350 ectodomain protein (AA 4-863) and 23 hybridomas producing gp350 specific antibodies were identified. To further characterize the biochemical properties of the 23 antibodies generated, the antibodies were purified from the hybridoma supernatants using protein A spin columns, followed by SDS-PAGE to confirm the purity of all antibodies (FIG. 1A).

These novel antibodies were analyzed by flow cytometric analysis for surface expression of gp350 protein on $10^6$ CHO cells transfected with 1 μg of pCAGGS-gp350. gp350 expressing cells were resuspended in PBS, stained with anti-gp350 mAb, which detects the gp350 ED, followed by secondary Ab goat anti-mouse conjugated to AF488. Additionally, western blot analysis was conducted on untransfected and pCAGGS-gp350 transfected CHO lysate. Anti-gp350 mAb 72A1 was used as a positive control (1:100) and anti-gp350 hybridoma clone supernatants were used at 1:50, and anti-mouse secondary antibody was used at 1:2000.

Figure 1B:
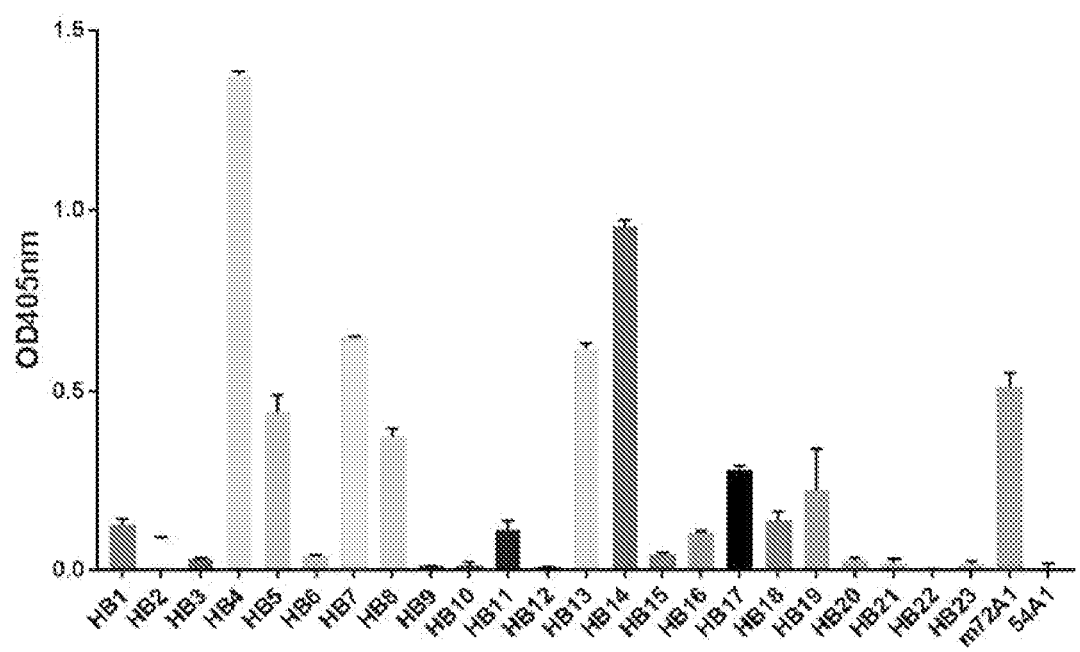

It was found that all 23 hybridoma producing antibodies, designated HB1-23, recognized the gp350 antigen in an initial ELISA screening using unfractionated and unpurified hybridoma supernatants (data not shown). When the quantified amount of the purified antibodies (10 μg/ml) was reevaluated using indirect ELISA, all of the 23 antibodies and m72A1 (anti-gp350 positive control) had ELISA signals greater than two times those of anti-KSHV gH/gL mAb 54A1 (negative control), and were considered positive/specific to gp350 (FIG. 1B). Of the 23 gp350-positive hybridoma producing antibodies identified, HB4, HB5, HB7, HB13, and HB14 demonstrated binding strength equal to or greater than that of the positive control, m72A1. This difference in binding of the antibodies could be due to differential exposure of cognate epitopes on gp350 in the assay performed.

Figure 1C:
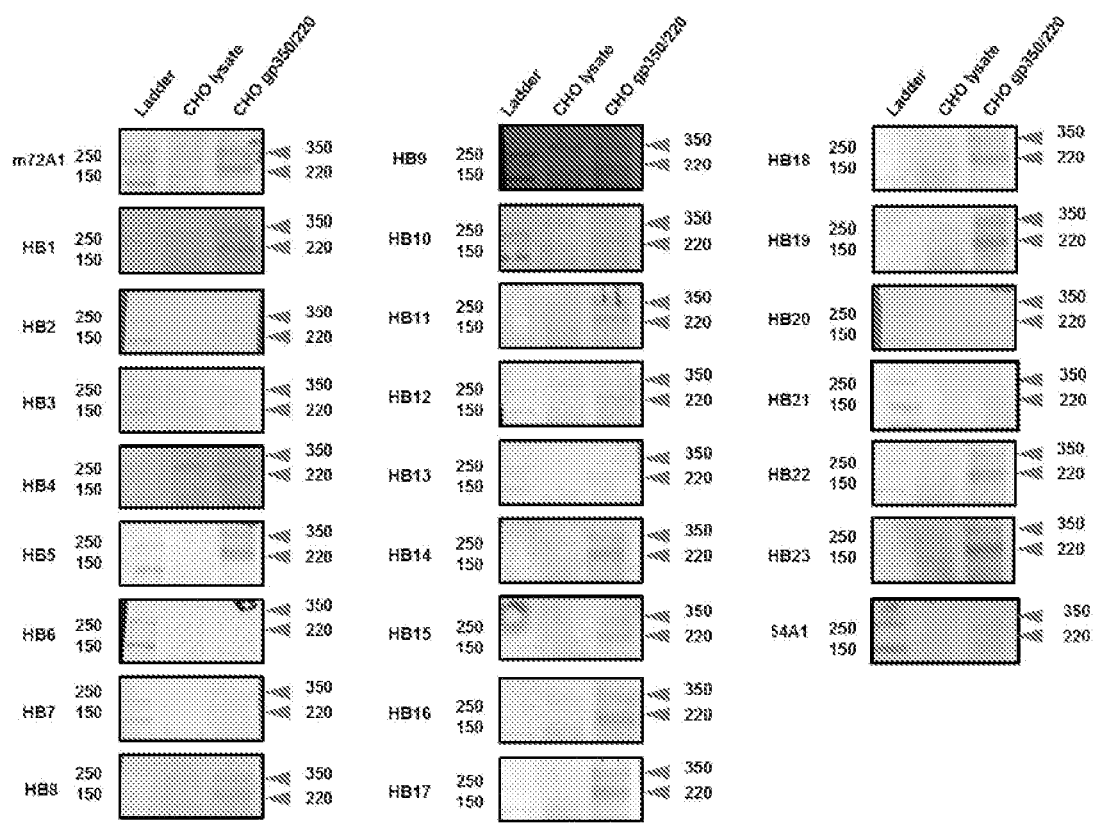
Figure 1D:
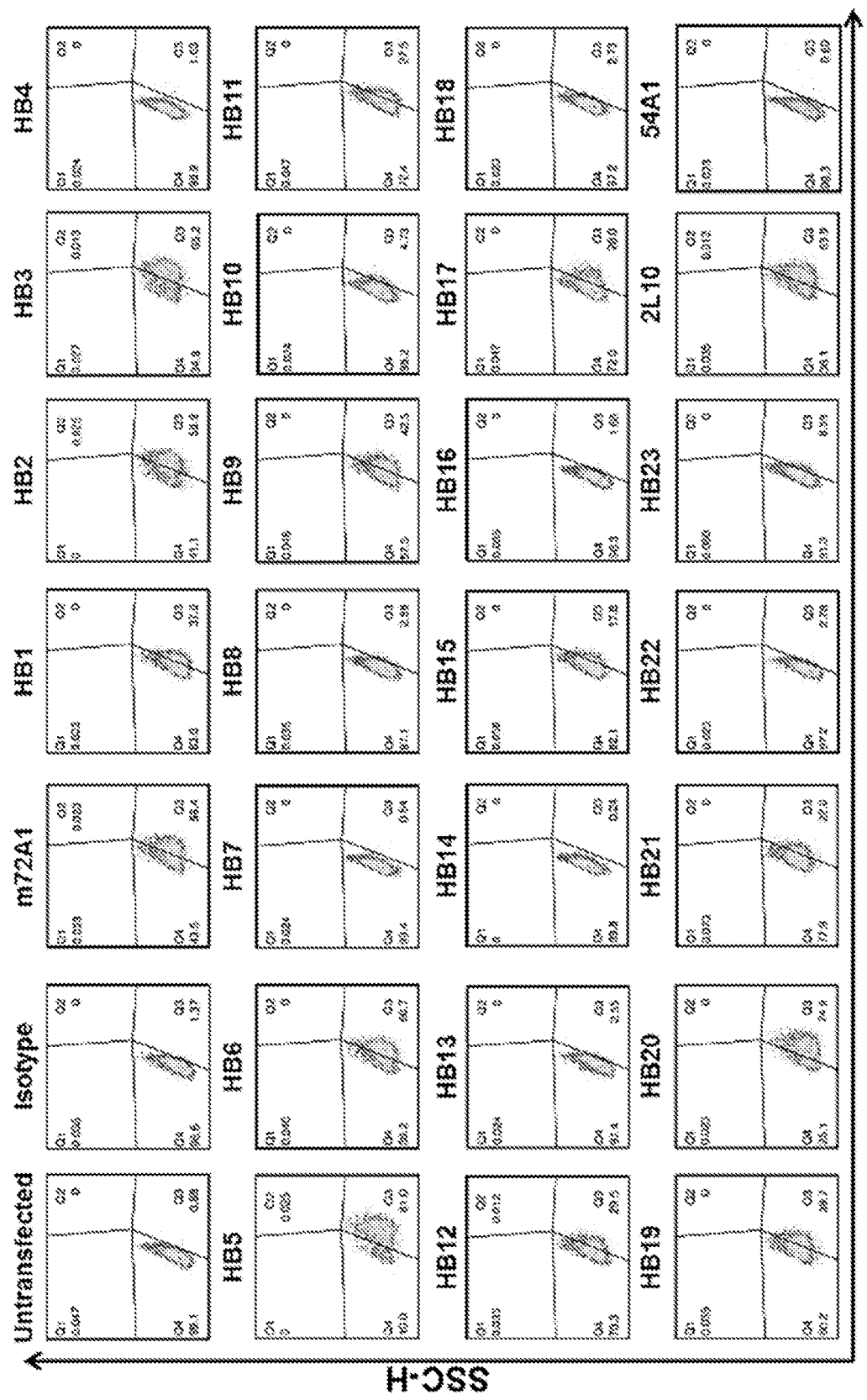
Figure 1E:
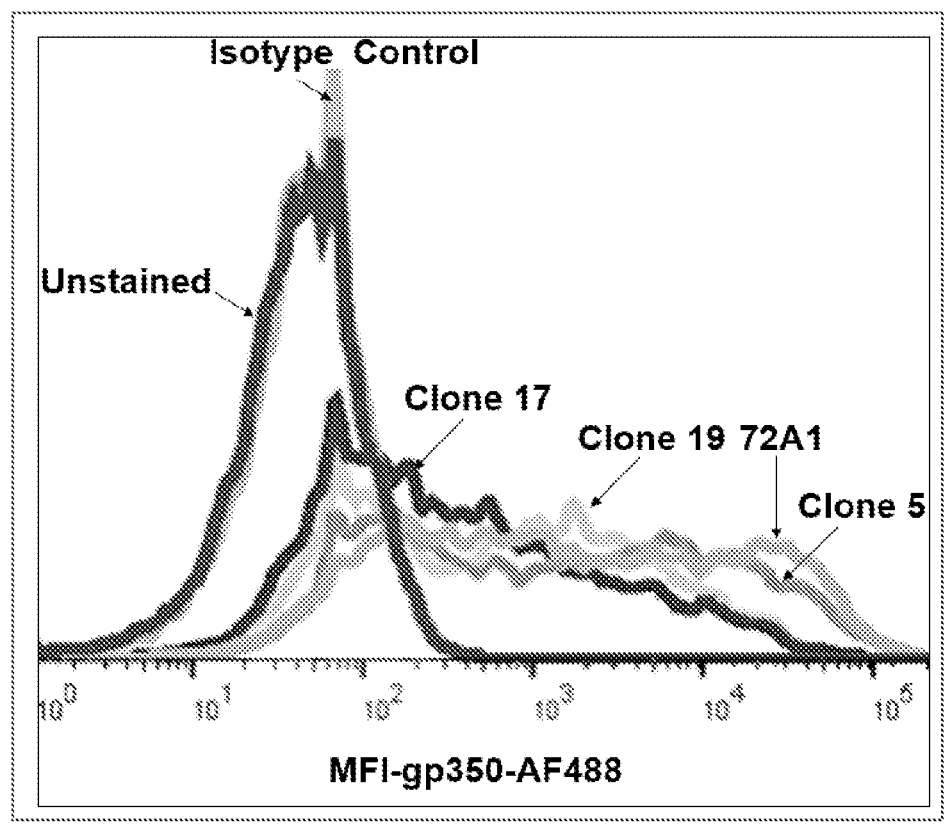

Determining the nature of the binding between an antibody and its target antigen is an important consideration for the performance and specificity of an antibody, as it can involve the recognition of a linear or conformational epitope (49). The ability of the purified antibodies to bind linear epitopes was evaluated by performing immunoblot analysis of denatured gp350 antigen expressed on Chinese hamster ovary (CHO) cells, and 16 of the 23 antibodies detected both the 350 kDa and the 220 kDa splice variant. In contrast, HB2, HB3, HB6, HB7, HB13, HB20, and HB21, as well as the negative control 54A1, failed to recognize either of the denatured isoforms of gp350 (FIG. 1C). The antibodies' ability to bind conformational epitopes was further characterized by flow cytometric analysis of CHO cells stably expressing gp350 on the cell surface. HB1, HB2, HB3, HB5, HB6, HB9, HB11, HB12, HB15, HB17, HB19, HB20, HB21, and m72A1 antibodies readily recognized gp350 (FIGS. 1D and 1E). The fact that HB2, HB3, HB20, and HB21 detected gp350 by flow cytometry, but not by immunoblot, suggests that these four antibodies only recognized conformational epitopes (i.e., native) on gp350, whereas HB5, HB9, HB11, HB15, HB17, and HB19 recognized both linear and conformational epitopes (FIGS. 1C-1E). The observation that all 23 anti-gp350 antibodies recognized the gp350 antigen either by indirect ELISA, flow cytometry, or immunoblot assay suggests that antibodies that are specific to EBV gp350 protein were successfully produced. In addition, the isotypes of the newly generated antibodies were determined to be IgG1 (n=14), IgG2a (n=5), IgG2b (n=1), a mixture of IgG1 and IgG2b (n=1), and a mixture of IgG1 and IgM (n=2) (Table 4).

TABLE 4

Summarized biochemical and functional characterization of anti-gp350 antibodies

| Antibody | IgG sub-class | Light chain | ELISA binding to purified EBV gp350/220 | Flow cytometry (CHO Cells) | Western blot |
|---|---|---|---|---|---|
| HB1 | IgG1 | κ | + | + | + |
| HB2 | IgG2a | κ | + | + | − |
| HB3 | IgG2a | κ | + | + | − |
| HB4 | IgG1 | κ | + | − | + |
| HB5 | IgG2a | κ | + | + | + |
| HB6 | IgG1 | κ | + | + | − |
| HB7 | IgG1 | κ | + | − | − |
| HB8 | IgG1 | κ | + | − | + |
| HB9 | IgG2a | κ | + | + | + |
| HB10 | IgG1 | κ | + | − | + |
| HB11 | IgG1 | κ | + | + | + |
| HB12 | IgG1 | κ | + | + | + |
| HB13 | IgG1 | κ | + | − | − |
| HB14 | IgG1 | κ | + | − | + |
| HB15 | IgG1 | κ | + | + | + |
| HB16 | IgG1/IgM | κ | + | − | + |
| HB17 | IgG2b | κ | + | + | + |
| HB19 | IgG1/IgM | κ | + | + | + |
| HB20 | IgG2a | κ | + | + | − |
| HB21 | IgG1/IgG2b | κ | + | + | − |
| HB22 | IgG1 | κ | + | − | + |
| HB23 | IgG1 | κ | + | + | + |
| m72A1 | IgG1 | κ/λ | + | + | + |

Figure 2:
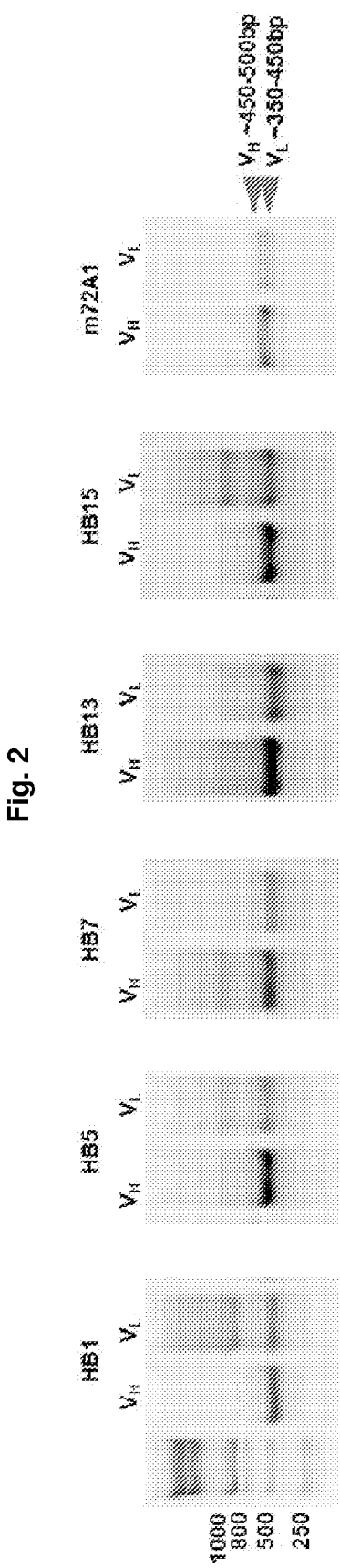
FIG. 2 shows agarose gel analysis of PCR products of heavy chain of select novel anti-gp350 antibodies (HB1, HB4, HB7, HB13, and HB15) and m72A1 was used as a positive control.

Example 3: Identification and Characterization of 15 Novel Anti-350 Monoclonal Antibodies To determine whether the generated hybridomas were monoclonal or a mixture of antibodies, the VH and VL variable region genes of the 23 new anti-gp350 antibodies, as well as m72A1 (positive control), were sequenced using Illumina MiSeq. The sequence of the CDR of m72A1 antibody was recently determined and published (50, 51). PCR was used to amplify the genes encoding the VH and VL chain regions in cDNAs generated from the 23 hybridoma cells, as well as from m72A1. The PCR products presented distinct bands for VH (~350-450 bp) and VL (~450-500 bp). FIG. 2 is a representation of identified bands for only a few selected hybridomas which did not yield additional multiple non-specific bands from PCR amplifications that required extra-purification steps. The purified fragments were sequenced, followed by in silico analysis, and CDRs for both VH and VL were identified (Table 1). As previously reported, two unique IgG1 VH and two unique VL chains, one kappa and one lambda sequence of m72A1, were identified using the light chain kappa degenerative primers and specific primers for the lambda light chain (50). These sequences were >94% identical to the previously published sequences, suggesting that m72A1 exists as a mixture of antibodies, instead of the reported mAb (51). Similar to m72A1, HB4, HB13, HB15, and HB23 hybridomas each produced a mixture of two antibodies, with two unique sequences of the VH chain showing at >5% frequencies, suggesting that they are not mAbs (Table 5). Coding sequences for VL chains for HB7, HB9, and HB17 were unable to be identified, unless the frequencies were lowered to >1% (Table 5); in this case, the identified coding VL chain sequences were identical.

TABLE 5

Summary of Illumina Dual Demultiplex of $V_H$ and $V_L$ Regions

| Sample | Chain | Starting Pairs | PEAR Merged Reads | Length Filtered Reads | Primer Matched Reads | 3× Reads | >5% Unique Coding | >5% Unique Non-Coding | |
|---|---|---|---|---|---|---|---|---|---|
| HB1 | HEAVY | 51,641 | 51,210 | 46,655 | 32,482 | 22,725 | 1 | 0 | |
|  | LIGHT | 280,048 | 279,012 | 100,725 | 68,041 | 58,570 | 1 | 1 | |
| HB2 | HEAVY | 22,793 | 22,621 | 16,475 | 11,415 | 7,429 | 1 | 0 | |
|  | LIGHT | 167,230 | 166,496 | 161,764 | 132,752 | 115,886 | 1 | 1 | |
| HB3 | HEAVY | 26,382 | 26,162 | 25,542 | 16,910 | 11,709 | 1 | 0 | |
|  | LIGHT | 12,681 | 12,609 | 11,753 | 9,809 | 8,023 | 1 | 1 | |
| HB4 | HEAVY | 38,811 | 38,238 | 17,151 | 11,957 | 7,217 | 2 | 0 | § |
|  | LIGHT | 179,249 | 129,752 | 111,996 | 78,392 | 66,419 | 1 | 1 | |
| HB.5 | HEAVY | 42,951 | 42,173 | 35,793 | 25,842 | 17,173 | 1 | 0 | |
|  | LIGHT | 176,073 | 175,267 | 168,806 | 141,712 | 127,045 | 1 | 1 | |
| HB6 | HEAVY | 26,142 | 25,981 | 22,245 | 15,658 | 10,453 | 1 | 0 | |
|  | LIGHT | 171,996 | 171,370 | 167,730 | 138,348 | 122,397 | 1 | 1 | |
| HB7 | HEAVY | 32,443 | 32,094 | 25,449 | 17,615 | 11,836 | 1 | 0 | |
|  | LIGHT | 67,031 | 63,924 | 37,344 | 26,271 | 22,378 | 1 | 1 | * |
| HB8 | HEAVY | 140,091 | 103,349 | 92,744 | 58,292 | 31,583 | 1 | 0 | |
|  | LIGHT | 151,244 | 115,527 | 102,439 | 82,154 | 70,803 | 1 | 1 | |
| HB9 | HEAVY | 37,057 | 36,473 | 19,544 | 11,585 | 7,358 | 1 | 0 | |
|  | LIGHT | 409,432 | 310,529 | 136,074 | 106,820 | 90,063 | 1 | 2 | * |
| HB10 | HEAVY | 38,181 | 37,981 | 26,043 | 17,104 | 11,391 | 1 | 0 | |
|  | LIGHT | 114,255 | 112,498 | 106,914 | 84,368 | 75,370 | 1 | 1 | |
| HB11 | HEAVY | 22,225 | 21,841 | 6,956 | 4,408 | 2,465 | 1 | 0 | |
|  | LIGHT | 106,465 | 102,278 | 65,332 | 50,232 | 44,527 | 1 | 0 | |
| HB12 | HEAVY | 83,044 | 82,355 | 46,350 | 30,276 | 20,886 | 1 | 0 | |
|  | LIGHT | 53,098 | 47,336 | 15,823 | 7,560 | 5,845 | 1 | 1 | |

TABLE 5-continued

Summary of Illumina Dual Demultiplex of $V_H$ and $V_L$ Regions

| Sample | Chain | Starting Pairs | PEAR Merged Reads | Length Filtered Reads | Primer Matched Reads | 3× Reads | >5% Unique Coding | >5% Unique Non-Coding | |
|---|---|---|---|---|---|---|---|---|---|
| HB13 | HEAVY | 81,451 | 80,372 | 47,995 | 32,216 | 20,139 | 2 | 0 | § |
|  | LIGHT | 27,314 | 24,774 | 8,987 | 5,457 | 4,104 | 2 | 1 |  |
| HB14 | HEAVY | 76,299 | 75,357 | 28,309 | 19,104 | 12,939 | 1 | 0 |  |
|  | LIGHT | 153,011 | 149,264 | 48,474 | 29,710 | 25,133 | 1 | 1 |  |
| HB.15 | HEAVY | 26,551 | 26,410 | 16,387 | 11,434 | 7,002 | 2 | 0 | § |
|  | LIGHT | 78,525 | 77,778 | 43,509 | 29,504 | 24,731 | 1 | 1 |  |
| HB16 | HEAVY | 54,249 | 53,943 | 9,517 | 7,128 | 4,179 | 1 | 0 |  |
|  | LIGHT | 42,048 | 40,351 | 30,602 | 22,758 | 18,251 | 2 | 1 | § |
| HB17 | HEAVY | 111,614 | 110,882 | 81,428 | 50,844 | 35,949 | 1 | 0 |  |
|  | LIGHT | 102,490 | 100,488 | 83,925 | 65,925 | 57,727 | 1 | 1 | * |
| HB18 | HEAVY | 211,215 | 155,410 | 146,256 | 91,009 | 50,308 | 1 | 0 |  |
|  | LIGHT | 212,261 | 161,879 | 155,235 | 123,096 | 105,959 | 1 | 1 |  |
| HB19 | HEAVY | 109,692 | 82,221 | 20,546 | 12,587 | 7,274 | 1 | 1 |  |
|  | LIGHT | 70,828 | 69,744 | 62,572 | 48,354 | 42,051 | 1 | 1 |  |
| HB20 | HEAVY | 15,781 | 15,632 | 12,789 | 7,757 | 4,852 | 1 | 0 |  |
|  | LIGHT | 135,527 | 133,208 | 118,513 | 90,717 | 78,701 | 1 | 1 |  |
| HB21 | HEAVY | 15,312 | 15,202 | 8,577 | 5,645 | 3,420 | 1 | 0 |  |
|  | LIGHT | 102,450 | 100,171 | 89,059 | 68,552 | 60,500 | 1 | 1 |  |
| HB22 | HEAVY | 217,959 | 156,488 | 154,008 | 95,755 | 50,245 | 1 | 0 |  |
|  | LIGHT | 205,334 | 156,986 | 143,386 | 108,728 | 85,136 | 1 | 0 |  |
| HB23 | HEAVY | 196,390 | 143,929 | 123,028 | 71,076 | 39,358 | 2 | 0 | § |
|  | LIGHT | 158,594 | 120,140 | 115,476 | 90,004 | 78,787 | 2 | 0 |  |
| 72A1 | HEAVY | 213,480 | 158,199 | 156,215 | 107,395 | 68,486 | 2 | 0 | § |
|  | LIGHT | 187,216 | 140,964 | 132,945 | 105,783 | 91,208 | 1 | 1 |  |

* Hybridoma with $V_L$ chain sequences identified with >1% frequency, § Hybridoma with more than one unique, plausible-coding $V_H$ chain sequence with >5% frequency. The term "unique" refers to unique sequence counts (so, identical sequences found in a substantial frequency of merged reads, not necessarily unique compared to other samples).

The analysis and comparison of the VH and VL chain gene sequences of the 23 hybridomas compared to m72A1 showed unique sequences within the CDR 1-3 region (Table 1). Only HB8 and HB18 had identical VH and VL chain gene sequences, suggesting that the two are the same clone isolated separately; therefore, HB18 was excluded from subsequent experiments. One of the two paired sequences from HB15 hybridoma mixture was confirmed to have identical VH and VL gene sequences to that of mAb HB10; however, based on the previous characterization, the presence of the additional paired sequenced in the HB15 hybridoma was sufficient to confer subtle differences in biochemical interactions with gp350 between the HB10 and HB15 purified antibodies. In addition, the germline genes for the VH and VL chains of the new 15 anti-gp350 mAbs and m72A1 were determined (Table 6).

TABLE 6

Identification of the germline genes for VH and VL of 15 new mAbs and m72A1

| Antibodies | V-GENE and allele | J-GENE and allele | V-GENE and allele | J-GENE and allele |
|---|---|---|---|---|
| HB1 | IGHV2-9*02 | IGHJ4*01 | IGKV6-15*01 | IGKJ2*01 |
| HB2 | IGHV9-2-1*01 | IGHJ4*01 | IGKV4-72*01 | IGKJ5*01 |
| HB3 | IGHV1S81*02 | IGHJ4*01 | IGKV10-96*01 | IGKJ1*01 or IGKJ1*02 |
| HB5 | IGHV1S45*01 | IGHJ3*01 | IGKV5-48*01 | IGKJ5*01 |
| HB6 | IGHV9-2-1*01 | IGHJ4*01 | IGKV4-72*01 | IGKJ5*01 |
| HB7 | IGHV1-15*01 or IGHV1-23*01 | IGHJ1*01 | IGKV6-13*01 | IGKJ5*01 |
| HB8 | IGHV9-3-1*01 | IGHJ3*01 | IGKV1-117*01 | IGKJ2*01 |
| HB9 | IGHV5-6-4*01 | IGHJ1*01 | IGKV1-117*01 | IGKJ2*01 |
| HB10 | IGHV1S81*02 | IGHJ4*01 | IGKV10-96*01 | IGKJ1*01 or IGKJ1*02 |
| HB11 | IGHV3-8*02 | IGHJ1*01 | IGKV4-50*01 | IGKJ1*01 |
| HB12 | IGHV1S81*02 | IGHJ4*01 | IGKV1-110*01 F | IGKJ4*01 |
| HB14 | IGHV1-15*01 | IGHJ1*01 | GKV1-110*01 F | IGKJ4*01 |
| HB17 | IGHV1S81*02 | IGHJ4*01 | IGKV10-96*01 | IGKJ1*01 or IGKJ1*02 |
| HB20 | IGHV1S81*02 | IGHJ4*01 | IGKV10-96*01 | IGKJ1*01 or IGKJ1*02 |
| HB22 | IGHV2-6*02 | IGHJ3*01 | IGKV1-117*01 | IGKJ1*01 |
| m72A1 | IGHV1-18*01 or IGHV1-26*01 | IGHJ3*01 | IGLV1*01 | IGLJ1*01 |

These results show that although only two mice were used in the generation of the antibodies, germline diversity was still present to some extent, and few mAbs shared the same germline gene rearrangement and evolution. Thus, based on the sequence analysis (FIG. 3), 15 unique anti-gp350 mAbs were generated, with distinct sequence identities from commercially available m72A1. The sequence of the widely used non-neutralizing antibody 2L10 (originally from G. Pearson's laboratory) was not available and therefore, 2L10 was not used in the sequence comparative studies.

Example 4: Humanization of m72A1 and HAMA Testing

Figure 4B:
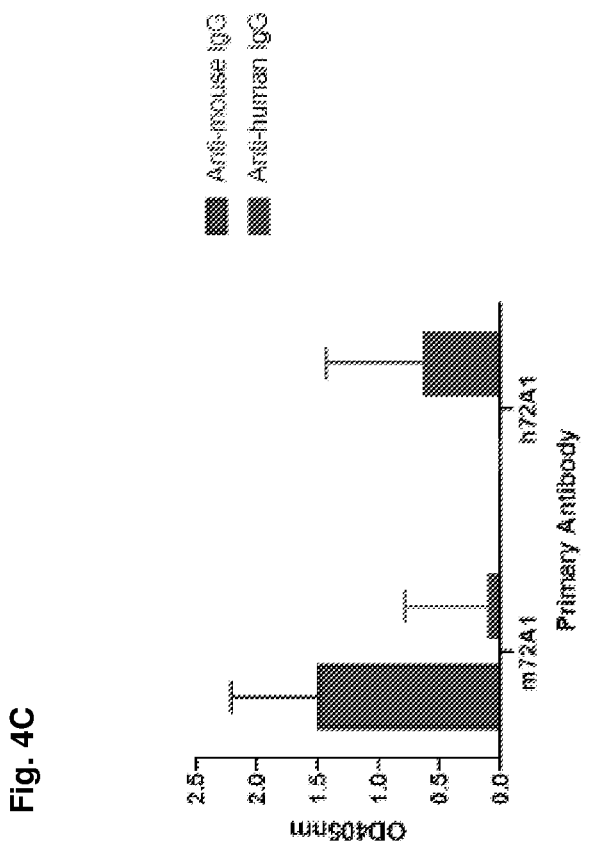
Figure 4C:
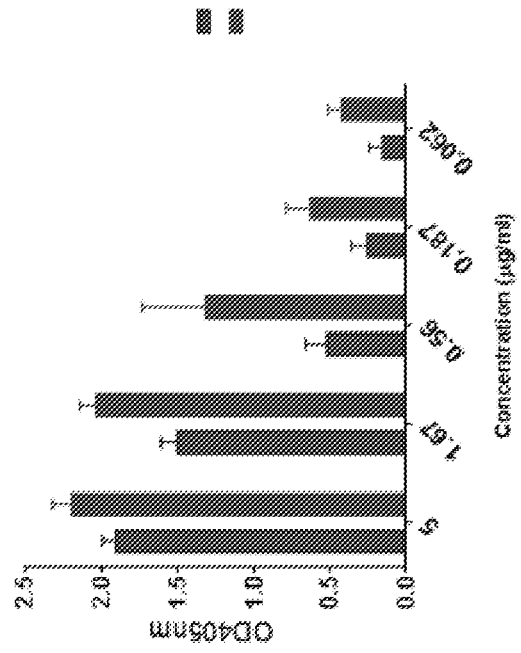
Figure 4D:
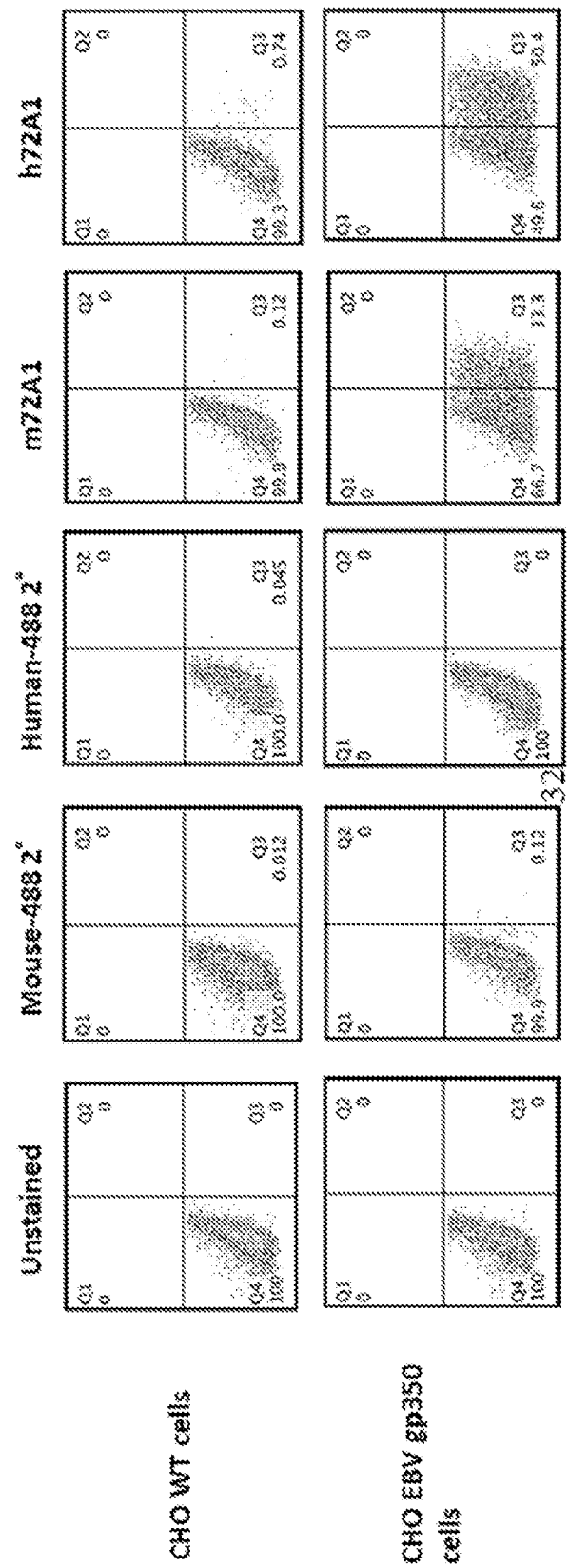

The m72A1 VH and VL chain sequences identified in this study were identical to the ones published by Herrman et al., and they were used to generate a humanized 72A1 352 (h72A1) as a strategy to reduce and/or eliminate HAMA (FIG. 4A). The disclosed h72A1 bound gp350 with similar strength to m72A1 in both ELISA (FIG. 4B). The levels of anti-mouse and anti-human activity retained in the h72A1 nAb were determined using ELISA. As shown in FIG. 4C, mouse 72A1 mAb reacted strongly to goat-anti-mouse IgG as compared to goat anti-human IgG (9-fold, p<0.0001) and 28-fold above the background (1×PBS) (p<0.0001). In contrast, h72A1 mAb did not react at all to goat anti-mouse, but specifically reacted strongly to goat anti-human IgG (2100-fold, p<0.0001) over the background. To determine whether h72A1 still recognized gp350 in its native conformation, flow cytometric analysis was performed. h72A1 recognized native epitopes of gp350 expressed on CHO cells surface, comparable to m72A1 360 (FIG. 4D). These results indicate that humanization of m72A1 did not affect its ability to recognize native gp350, but it abrogated anti-mouse reactivity and increased anti-human reactivity.

Example 5: Neutralization Assay

Currently, m72A1 is the only commercially available anti-gp350 nAb (68). However, this antibody was recently reported to be a mixture of both functional and non-functional antibodies (50). The ability of the 15 new mAbs (10 µg/ml or 50 µg/ml) to neutralize purified eGFP-tagged-EBV infection of a B cell line (Raji) in vitro was evaluated and compared to that of m72A1 (mixture) and the newly cloned and biochemically characterized h72A1, following standardized procedures (47, 52). The percentage of eGFP+ cells (percent infection) was determined using flow cytometry as described (47). The nAbs 72A1 and E1D1 were used as positive controls, whereas the anti-gp350 non-neutralizing mAb 2L10 and KSHV gH/gL mAb 54A1 were used as negative controls. Because HB4, HB13, HB15, HB16, HB19, HB21, and HB23 were confirmed to be polyclonal based on isotyping and/or sequence data, they were eliminated from further consideration in the neutralization assay. HB18 was not used in neutralization experiments because it was identical to HB8.

Figure 5A:
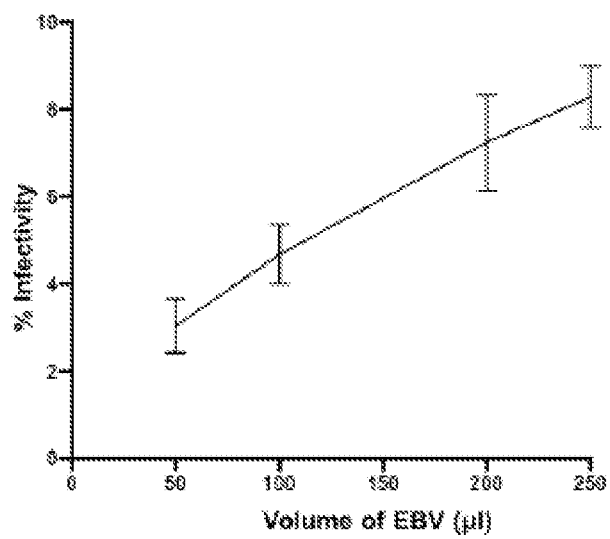
Figure 5B:
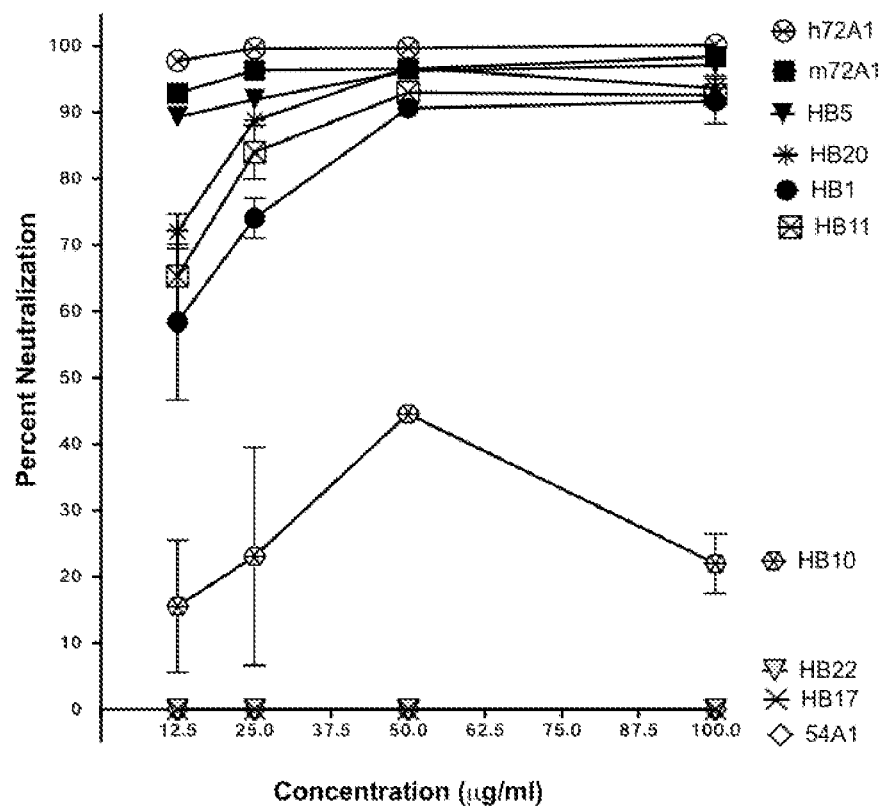
Figure 6A:
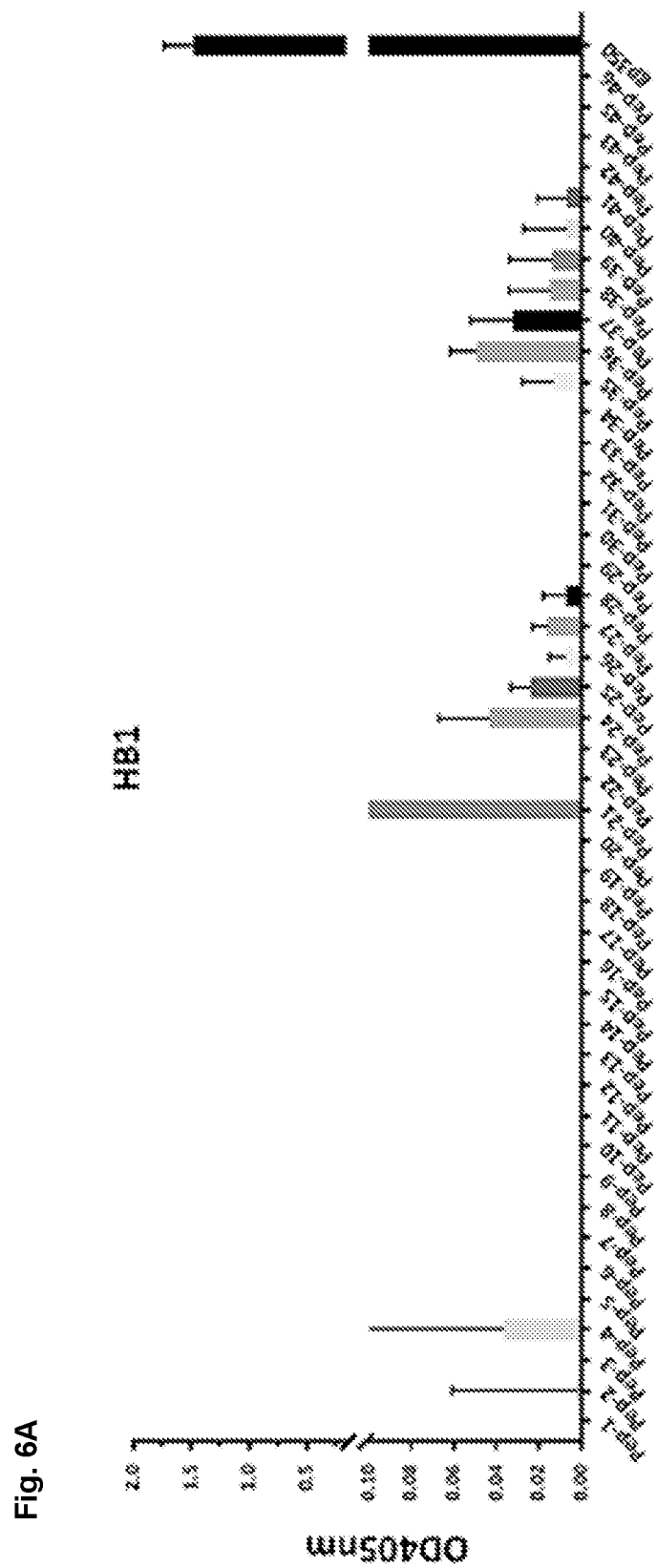
Figure 6B:
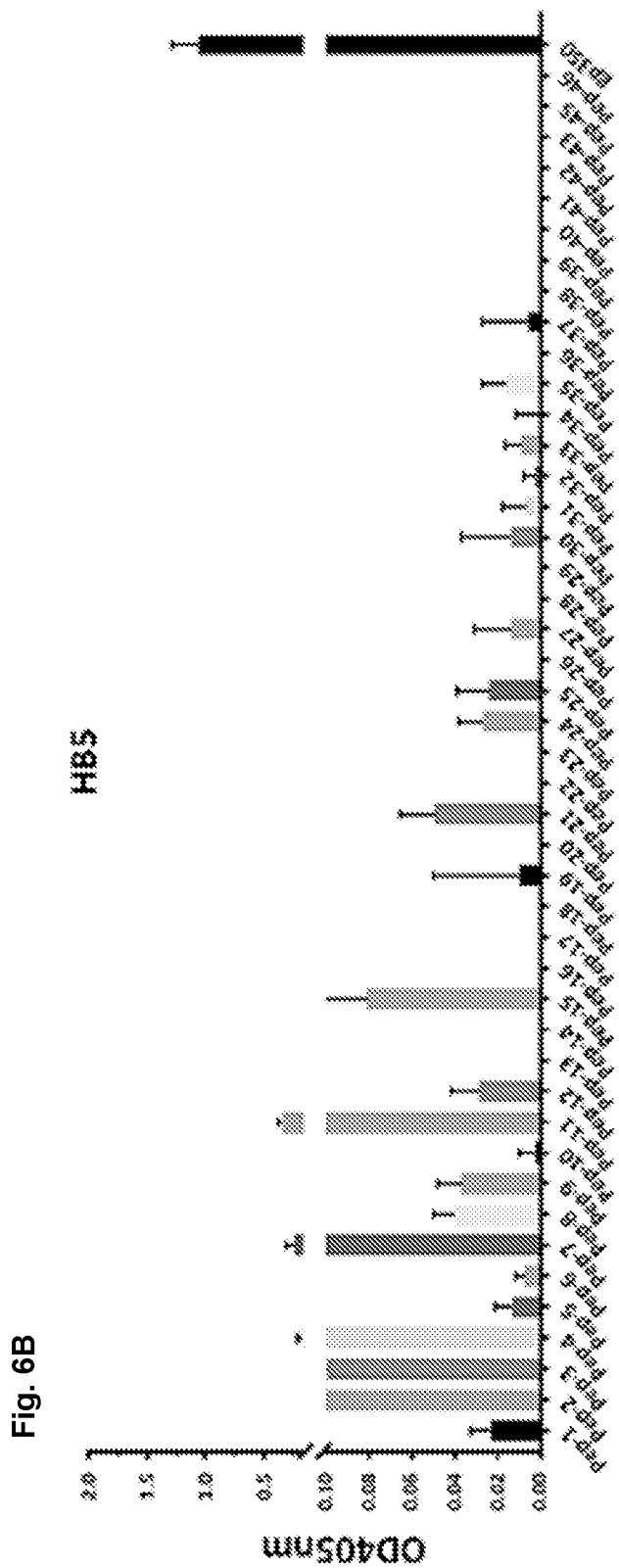
Figure 6C:
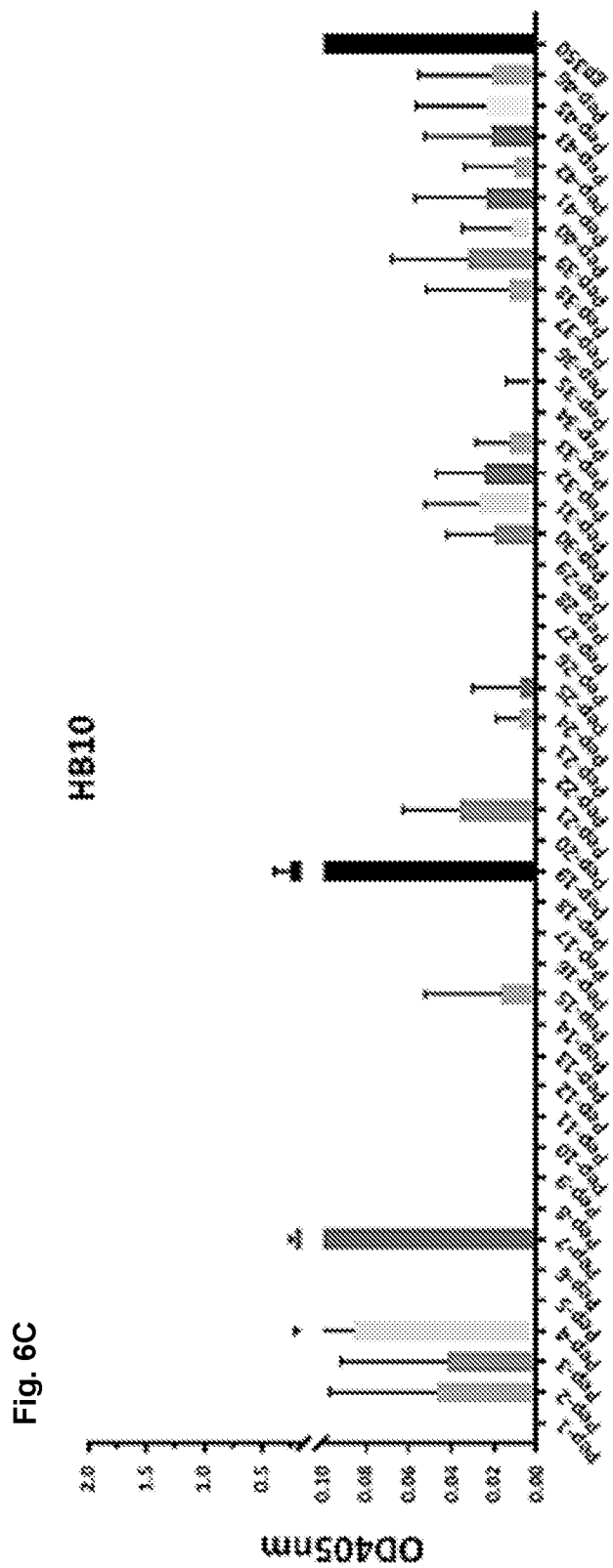
Figure 6D:
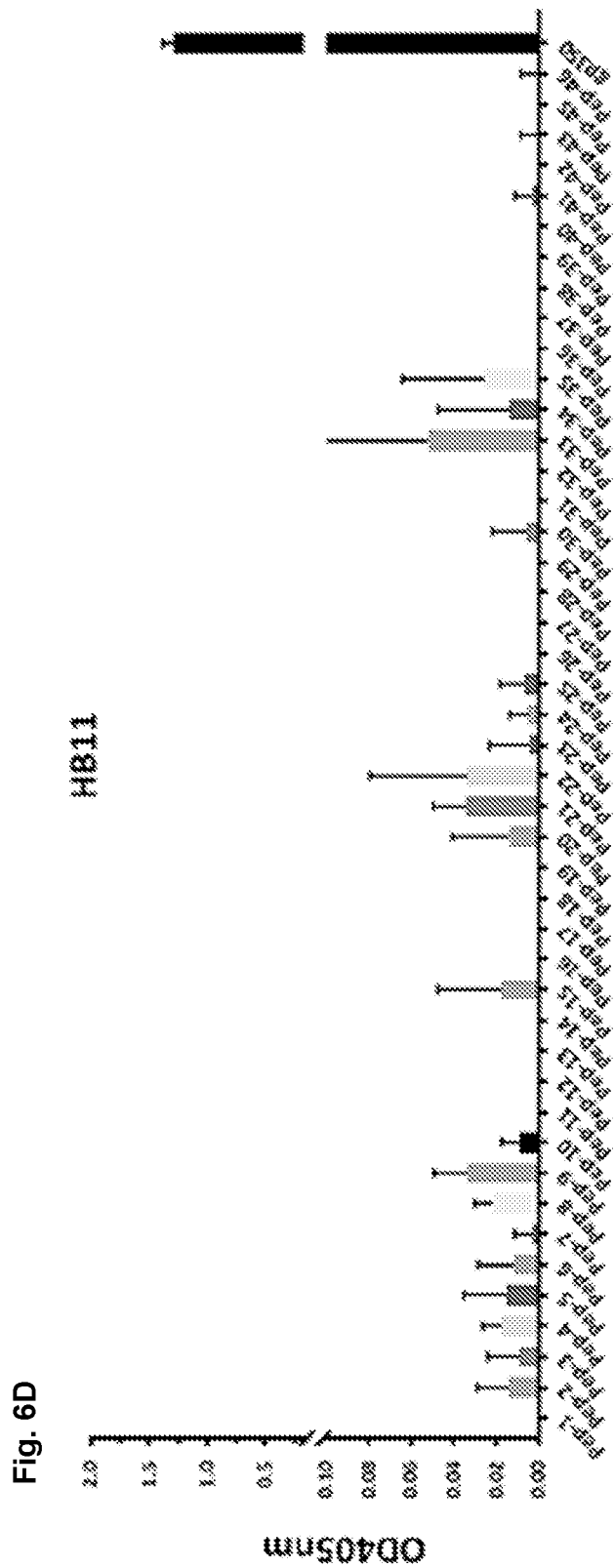
Figure 6F:
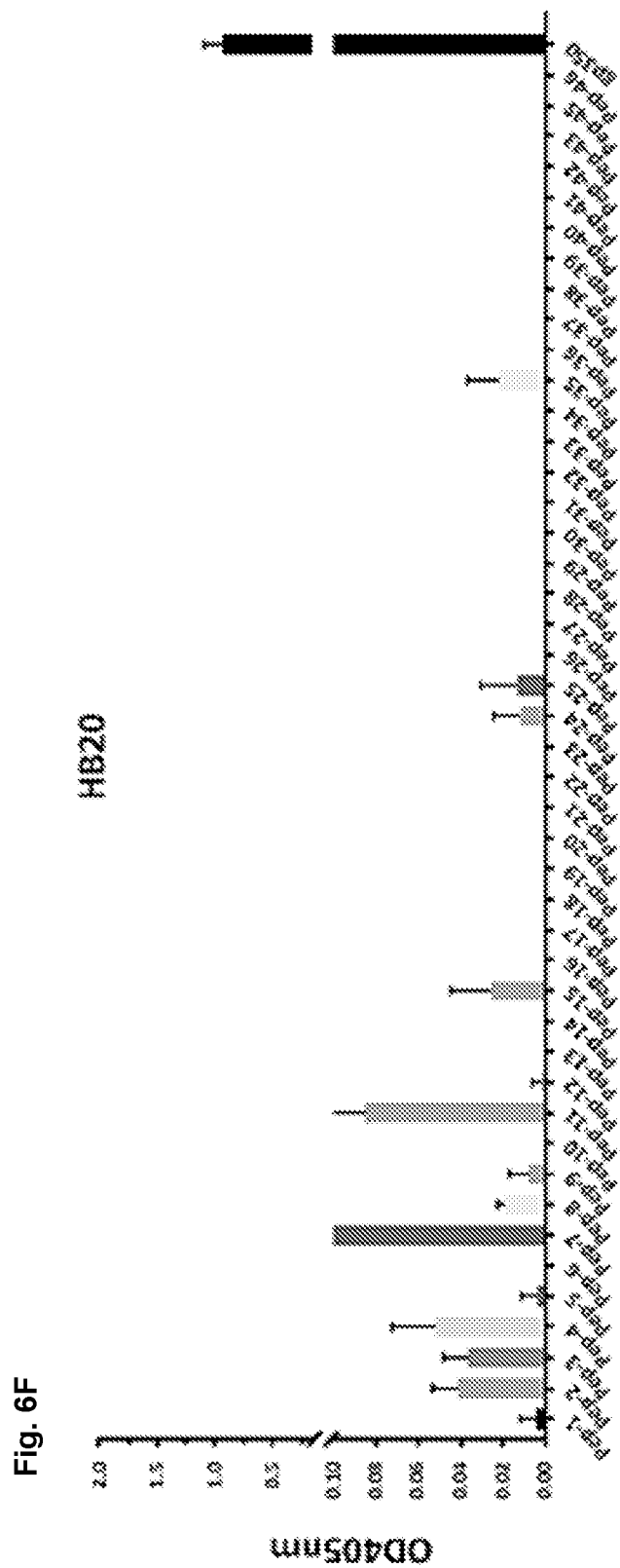
Figure 6G:
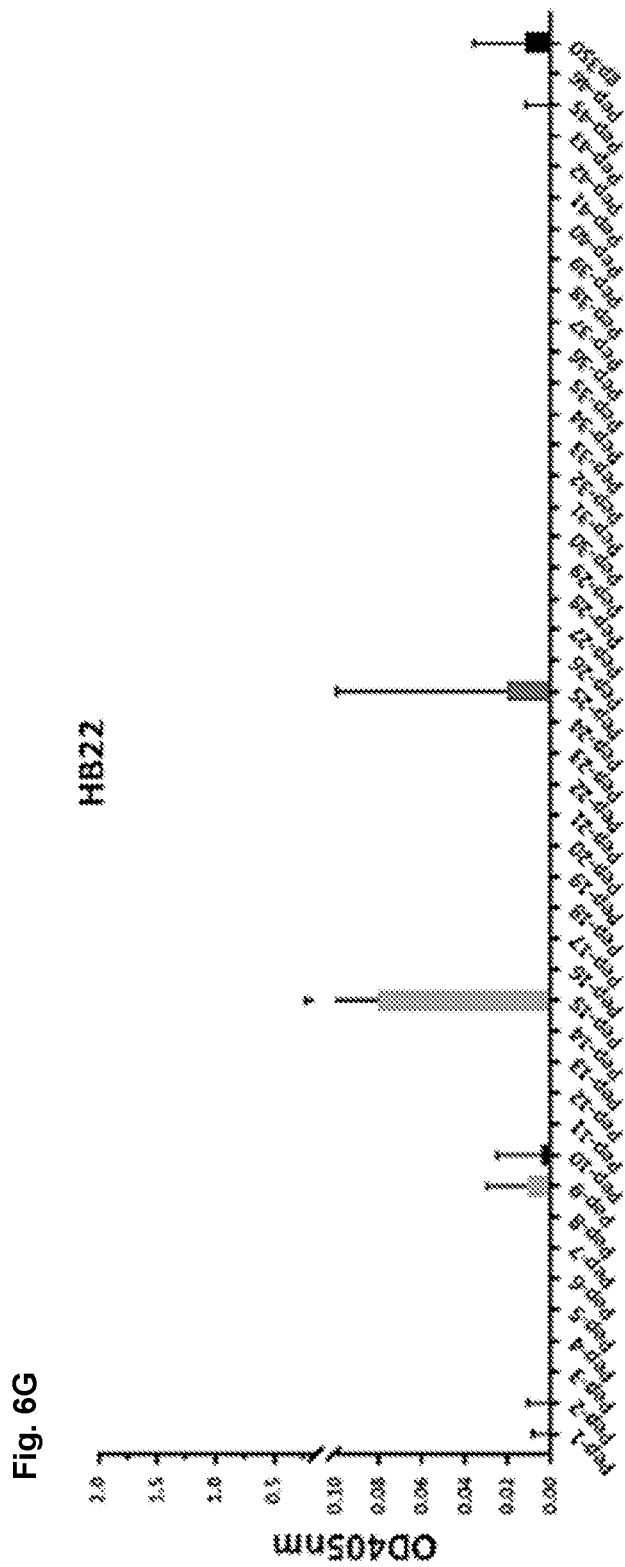
Figure 6H:
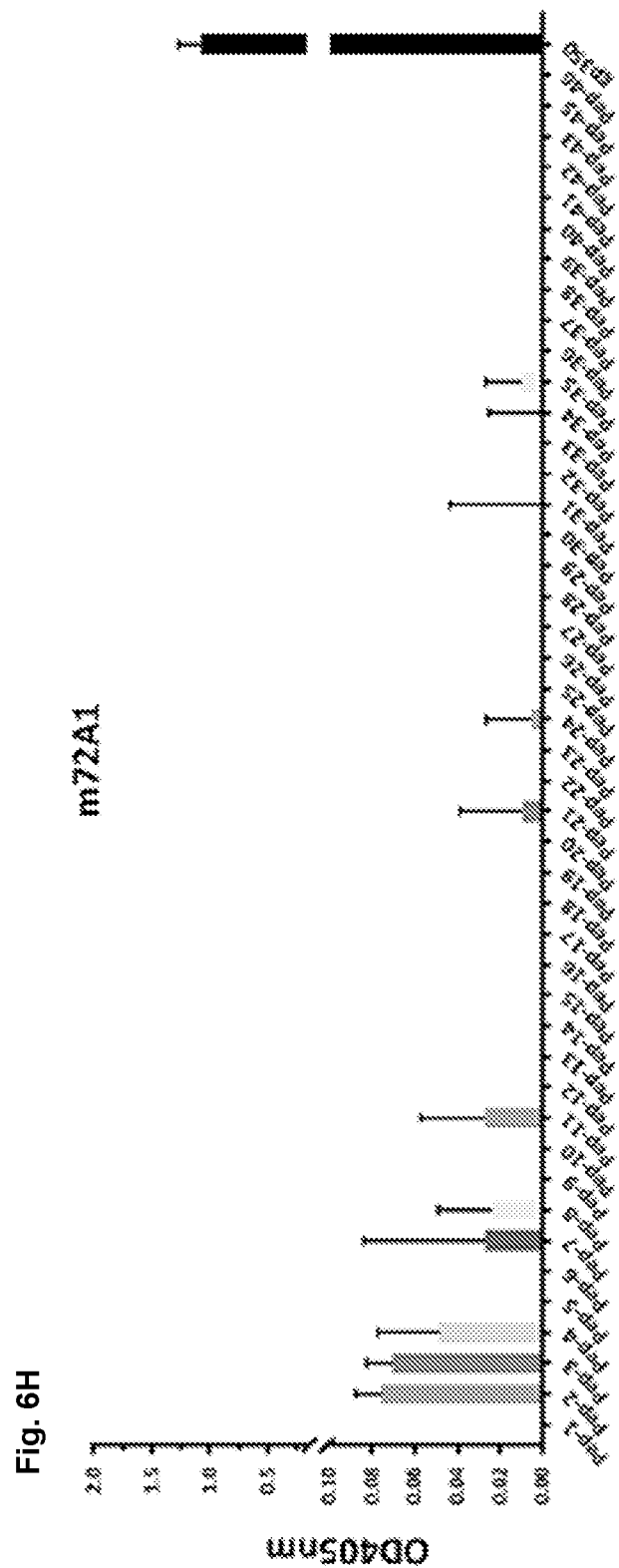
Figure 6I:
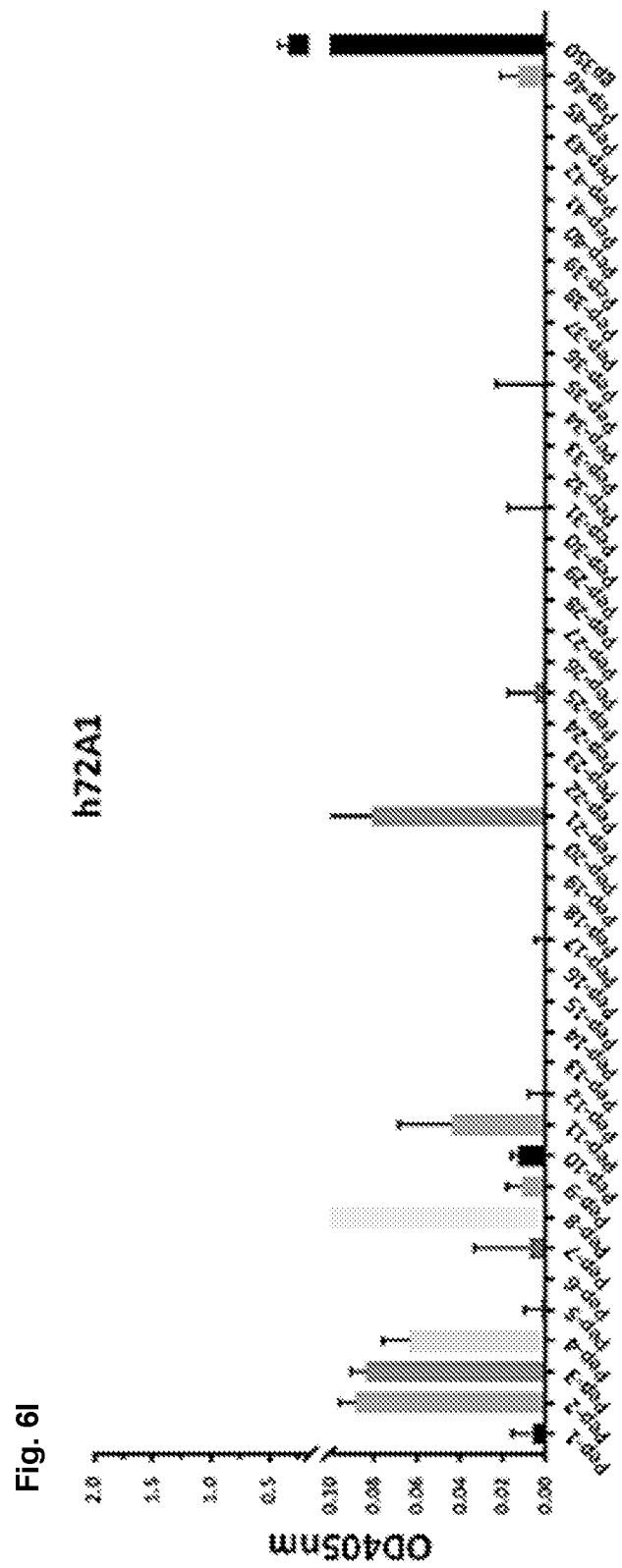

The purified eGFP-tagged-EBV was titered in Raji cells to determine percent EBV infection using a range of volumes (50-250 µl) (FIG. 5A). Then initial neutralization of EBV was conducted in Raji cells using purified mAbs at various concentrations (12.5, 25, 50, and 100 µg/ml). Only HB1, HB5, HB11, 375 HB22 and m72A1 showed a dose-dependent neutralization of EBV in Raji cells; the neutralization capability of HB5 (60-80%) was comparable to that of m72A1 (35-80%) (FIG. 5B). In contrast, HB2, HB3, HB6, HB7, HB8, HB9, HB10, HB12, HB14, HB17, and HB20 mAbs failed to neutralize EBV infection, even at the highest concentration. As expected, neither 2L10 nor 54A1 neutralized EBV infection, even at the highest mAb concentration of 100 µg/ml (FIG. 5B).

Subsequently, seven representative novel nAb and non-nAb anti-gp350 mAbs (HB1, HB5, HB10, HB11, HB17, HB20 and HB22) were purified as well as controls (m72A1, h72A1 and 54A1) using protein G affinity chromatography and size-exclusion chromatography in order to eliminate any potential impurities, then their potency in blocking EBV infection of Raji cells was reevaluated. Chromatography-purified HB1, HB5, HB11, and HB20, blocked EBV infection in a dose-dependent manner (FIG. 5C). HB5 was the most effective nAb, efficiently blocking EBV infection (90%) at percentages comparable to both m72A1 (93%) and h72A1 (98%), even at the lowest concentration of 12.5 µg/ml, with 97% nAb activity at 100 µg/ml (FIG. 5C). HB1, HB11, and HB20 neutralized EBV infection between 57-73% at the lowest concentration (12.5 µg/ml) and 90% at 100 µg/ml. Neither HB17, HB22, nor 54A1 blocked EBV infection; although HB10 blocked some EBV infection, nAb activity did not reach 50% even at the highest concentration of antibody used, thus it was classified as a non-nAb.

Example 6: Four Novel Gp350 nAbs Bind Antigenic Epitopes that Overlap with Those of 72A1

At least seven unique CD21 binding epitopes on EBV gp350 have been predicted (Table 3). One of these epitopes (AA 142-161) has been identified as the primary epitope recognized by m72A1 (59) and mice immunized with the 142-161 peptide elicit nAbs against EBV infection (51). To evaluate whether the selected novel nAbs (HB1, HB5, HB11, and HB20) and non-nAbs (HB10, HB17, and HB22) bind overlapping or non-overlapping target epitopes to those of 72A1, their ability to compete for binding to gp350 expressed stably on transfected CHO cells were determined. Antigen binding competition was observed between biotinylated m72A1 (1 µg/ml) and serially diluted (500, 250, 125, and 67.5 µg/ml) unlabeled gp350 nAbs (HB1, HB5, HB11, HB20, and h72A1), but not the gp350 non-nAbs (HB10, HB17, or HB22) or anti-KSHV gH/gL antibody 54A1 (negative control) (Table 7).

TABLE 7

Cell binding mAbs competition assay with EBV gp350 using biotinylated m72A1

| | % inhibition of biotinylated nAbs | | | |
|---|---|---|---|---|
| Unlabeled mAbs | 500 µg/ml | 250 µg/ml | 125 µg/ml | 67.5 µg/ml |
| HB1 | 91 | 89 | 81 | 81 |
| HB5 | 95 | 93 | 92 | 94 |
| HB10 | 12 | 14 | 16 | 13 |
| HB11 | 95 | 95 | 89 | 87 |
| HB17 | 32 | 32 | 6 | 0 |
| HB20 | 96 | 91 | 87 | 89 |
| HB22 | 10 | 3 | 16 | 9 |
| m72A1 | 91 | 93 | 94 | 97 |
| h72A1 | 98 | 95 | 93 | 89 |
| 54A1 | 18 | 7 | 10 | 4 |

However, previously non-nAbs HB10 and HB22, were shown not to bind native gp350 expressed on CHO cells using FACS (FIG. 1D), suggesting that the observed lack of competitive binding could be attributed to these two Abs not binding the native gp350 expressed on the CHO cells. These results indicate that nAbs HB1, HB5, HB11, and HB20, as well as h72A1, bind overlapping target epitopes with that of m72A1, while non-nAbs HB17, the only non-nAbs able to recognize gp350 in conformational form, binds different target epitopes. Similar results were obtained when cross-competition binding assays between 1 µg/ml biotinylated and 500 µg/ml unlabeled gp350 nAbs HB1, HB5, HB11, HB20, m72A1, and h72A1 and non-nAb HB17 were performed (Table 8), confirming that the newly developed gp350 nAbs bind overlapping epitopes to 72A1.

TABLE 8

Cross-competitive binding of EBV gp350
% inhibition of biotinylated nAbs

| Unlabeled mAbs | HB1 | HB5 | HB10 | HB11 | HB17 | HB20 | HB22 | m72A1 | h72A1 | 54A1 |
|---|---|---|---|---|---|---|---|---|---|---|
| HB1 | 92 | 97 | ND | 96 | 16 | 61 | ND | 98 | 95 | 4 |
| HB5 | 92 | 98 | ND | 93 | 9 | 73 | ND | 97 | 97 | 13 |
| HB10 | ND | ND | ND | ND | ND | ND | ND | ND | ND | ND |
| HB11 | 93 | 96 | ND | 96 | 17 | 3 | ND | 97 | 97 | 9 |
| HB17 | 23 | 32 | ND | 11 | 86 | 17 | ND | 24 | 16 | 0 |
| HB20 | 88 | 97 | ND | 89 | 13 | 59 | ND | 98 | 96 | 0 |
| HB22 | ND | ND | ND | ND | ND | ND | ND | ND | ND | ND |
| m72A1 | 82 | 97 | ND | 90 | 37 | 31 | ND | 98 | 98 | 1 |
| h72A1 | 87 | 97 | ND | 79 | 31 | 26 | ND | 98 | 98 | 0 |
| 54A1 | 0 | 0 | ND | 0 | 0 | 0 | ND | 0 | 3 | 0 |

ND—Not determined

Because of inability of non-nAbs, HB10 and HB22 to recognize conformational gp350, they were excluded from the cross competitive cell binding assays. Importantly, even though HB1, HB5, HB11, and HB20 competed with 72A1 for the same antigenic epitope, each of these nAbs had unique VH and VL sequences from 72A1 (Table 1, Table 2).

Example 7: Novel Anti-Gp350 nAbs and Non-nAbs Bind Three Major Immunodominant Regions on Gp350

To identify linear epitopes on gp350, anti-gp350 nAbs (HB1, HB5, HB11 and HB20) and non-nAbs (HB10, HB17, and HB22) were scanned in an ELISA-based assay using a peptide library consisting of sequential peptides (FIGS. 6A-6I). The peptide library, consisting of 20-mer peptides, covered the entire gp350 protein, with the exception of AA 862-881 (Table 9).

TABLE 9

Sequence, length and position of EBV gp350 peptides

| Peptide name | Peptide position | gp350 region | Peptide sequence | Peptide length |
|---|---|---|---|---|
| Pep-1 | 1-20 | 1 | MEAALLVCQYTIQSLIHLTG (SEQ ID NO: 132) | 20 |
| Pep-2 | 21-40 | 1 | EDPGFFNVEIPEFPFYPTON (SEQ ID NO: 133) | 20 |
| Pep-3 | 41-61 | 1 | VCTADVNVTINFDVGGKKHQL (SEQ ID NO: 134) | 21 |
| Pep-4 | 62-81 | 1 | DLDFGQLTPHTKAVYQPRGA (SEQ ID NO: 135) | 20 |
| Pep-5 | 82-101 | 1 | FGGSENATNLFLLELLGAGE (SEQ ID NO: 136) | 20 |
| Pep-6 | 102-121 | 2 | LALTMRSKKLPINVTTGEEQ (SEQ ID NO: 137) | 20 |
| Pep-7 | 122-141 | 2 | QVSLESVDVYFQDVFGTMWC (SEQ ID NO: 138) | 20 |
| Pep-8 | 142-161 | 2 | HHAEMQNPVYLIPETVPYIK (SEQ ID NO: 139) | 20 |
| Pep-9 | 162-181 | 2 | WDNCNSTNITAVVRAQGLDV (SEQ ID NO: 140) | 20 |
| Pep-10 | 182-201 | 2 | TLPLSLPTSAQDSNFSVKTE (SEQ ID NO: 141) | 20 |
| Pep-11 | 202-221 | 3 | MLGNEIDIECIMEDGEISQV (SEQ ID NO: 142) | 20 |
| Pep-12 | 222-241 | 3 | LPGDNKFNITCSGYESHVPS (SEQ ID NO: 143) | 20 |
| Pep-13 | 242-261 | 3 | GGILTSTSPVATPIPGTGYA (SEQ ID NO: 144) | 20 |
| Pep-14 | 262-281 | 3 | YSLRLTPRPVSRFLGNNSIL (SEQ ID NO: 145) | 20 |
| Pep-15 | 282-301 | 3 | YVFYSGNGPKASGGDYCIQS (SEQ ID NO: 146) | 20 |
| Pep-16 | 302-321 | 4 | NIVFSDEIPASQDMPTNTTD (SEQ ID NO: 147) | 20 |
| Pep-17 | 322-341 | 4 | ITYVGDNATYSVPMVTSEDA (SEQ ID NO: 148) | 20 |
| Pep-18 | 342-361 | 4 | NSPNVTVTAFWAWPNNTETD (SEQ ID NO: 149) | 20 |
| Pep-19 | 362-381 | 4 | FKCKWTLTSGTPSGCENISG (SEQ ID NO: 150) | 20 |
| Pep-20 | 382-401 | 4 | AFASNRTFDITVSGLGTAPK (SEQ ID NO: 151) | 20 |
| Pep-21 | 402-421 | 5 | TLIITRTATNATTTTHKVIF (SEQ ID NO: 152) | 20 |
| Pep-22 | 422-441 | 5 | SKAPESTTTSPTLNTTGFAD (SEQ ID NO: 153) | 20 |
| Pep-23 | 442-461 | 5 | PNTTTGLPSSTHVPTNLTAP (SEQ ID NO: 154) | 20 |
| Pep-24 | 462-481 | 5 | ASTGPTVSTADVTSPTPAGT (SEQ ID NO: 155) | 20 |
| Pep-25 | 482-501 | 5 | TSGASPVTPSPSPWDNGTES (SEQ ID NO: 156) | 20 |
| Pep-26 | 502-521 | 6 | KAPDMTSSTSPVTTPTPNAT (SEQ ID NO: 157) | 20 |

TABLE 9-continued

Sequence, length and position of EBV gp350 peptides

| Peptide name | Peptide position | gp350 region | Peptide sequence | Peptide length |
|---|---|---|---|---|
| Pep-27 | 522-541 | 6 | SPTPAVTTPTPNATSPTPAV (SEQ ID NO: 158) | 20 |
| Pep-28 | 542-561 | 6 | TTPTPNATSPTLGKTSPTSA (SEQ ID NO: 159) | 20 |
| Pep-29 | 562-581 | 6 | VTTPTPNATSPTLGKTSPTS (SEQ ID NO: 160) | 20 |
| Pep-30 | 582-601 | 6 | AVTTPTPNATSPTLGKTSPT (SEQ ID NO: 161) | 20 |
| Pep-31 | 602-621 | 7 | SAVTTPTPNATGPTVGETSP (SEQ ID NO: 162) | 20 |
| Pep-32 | 622-641 | 7 | QANATNHTLGGTSPTPVVIS (SEQ ID NO: 163) | 20 |
| Pep-33 | 642-661 | 7 | QPKNATSAVTTGQHNITSSS (SEQ ID NO: 164) | 20 |
| Pep-34 | 662-681 | 7 | TSSMSLRPSSNPETLSPSTS (SEQ ID NO: 165) | 20 |
| Pep-35 | 682-701 | 7 | DNSTSHMPLLTSAHPTGGEN (SEQ ID NO: 166) | 20 |
| Pep-36 | 702-721 | 8 | ITQVTPASISTHHVSTSSPA (SEQ ID NO: 167) | 20 |
| Pep-37 | 722-741 | 8 | PRPGTTSQASGPGNSSTSTK (SEQ ID NO: 168) | 20 |
| Pep-38 | 742-761 | 8 | PGEVNVTKGTPPQNATSPQA (SEQ ID NO: 169) | 20 |
| Pep-39 | 762-781 | 8 | PSGQKTAVPTVTSTGGKANS (SEQ ID NO: 170) | 20 |
| Pep-40 | 782-801 | 8 | TTGGKHTTGHGARTSTEPTT (SEQ ID NO: 171) | 20 |
| Pep-41 | 802-821 | 9 | DYGGDSTTPRPRYNATTYLP (SEQ ID NO: 172) | 20 |
| Pep-42 | 822-841 | 9 | PSTSSKLRPRWTFTSPPVTT (SEQ ID NO: 173) | 20 |
| Pep-43 | 842-861 | 9 | AQATVPVPPTSQPRFSNLSM (SEQ ID NO: 174) | 20 |
| Pep-44 | 862-881 | 9 | LVLQWASLAVLTLLLLLVMA (SEQ ID NO: 175) | 20 |
| Pep-45 | 882-901 | 9 | DCAFRRNLSTSHTYTTPPYD (SEQ ID NO: 176) | 20 |
| Pep-46 | 888-907 | 9 | NLSTSHTYTTPPYDDAETYV (SEQ ID NO: 177) | 20 |

This peptide could not be synthesized due to high hydrophobicity of AA residues in the sequence. Purified m72A1 and h72A1 nAbs were used as positive controls and anti-KSHV gH/gL 54A1 antibody as a negative control. Purified recombinant gp350 ectodomain was used as a control to validate the binding activity for all of the antibodies used. The overall gp350 sequence was divided into nine different regions consisting of ~100 AA (FIG. 7). The three major regions that exhibited the greatest affinity to anti-gp350 mAbs were: 1-101, 102-201, and 402-501 (Table 10).

TABLE 10

Summarized analysis of anti-gp350 mAb linear epitope binding to various regions of gp350

| mAbs | gp350 Regions | | | | | | | | |
|---|---|---|---|---|---|---|---|---|---|
|  | 1 | 2 | 3 | 4 | 5 | 6 | 7 | 8 | 9 |
| HB1 | x | — | — | — | x | x | — | x | — |
| HB5 | x | x | x | x | x | x | x | — | — |
| HB10 | x | — | — | — | x | — | x | x | x |
| HB11 | x | x | — | — | x | — | x | — | — |
| HB17 | x | — | — | — | — | x | — | — | x |
| HB20 | x | x | x | — | x | — | — | — | — |
| HB22 | x | — | — | — | — | — | — | — | — |
| m72A1 | x | x | — | — | x | — | — | — | — |
| h72A1 | x | x | — | — | x | — | — | — | — |

(X) represents positive binding of antibody to the region, (—) represents no binding of antibody to the region The AA 102-201 region was bound by only nAbs (HB5, HB11, HB20, m72A1 and h72A1), with the exception of HB1. Notably, this region (102-201) contains the epitope (AA 142-161) previously identified as a binding epitope for 72A1 and as a binding receptor for CR2 (Table 3), confirming that this is the main region that interacts with most gp350 nAbs. Because both nAbs and non-nAbs bound to AA 1-101 and 402-501, these two regions were considered to be immunodominant.

Example 8: Construction of Chimeric Gp350 nAbs

Figure 8A:
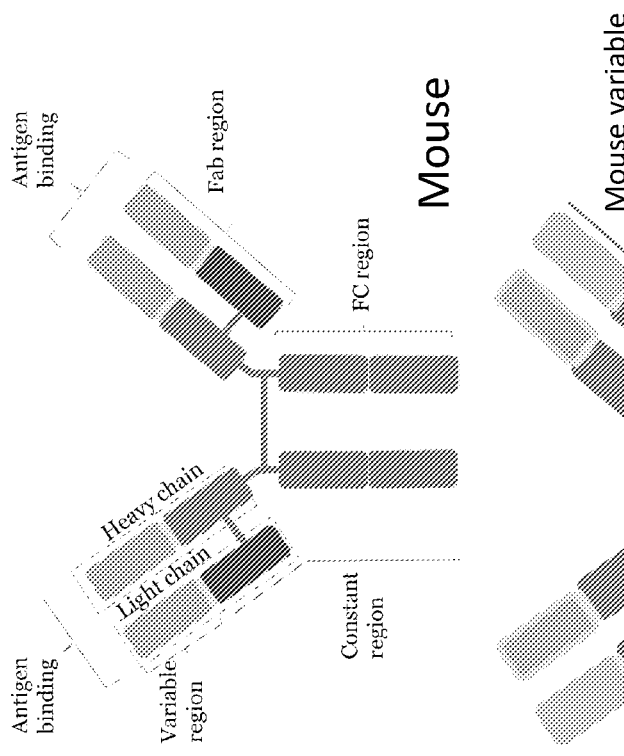
FIGS. 8A-8C show construction of chimeric gp350 nAbs.
Figure 8B:
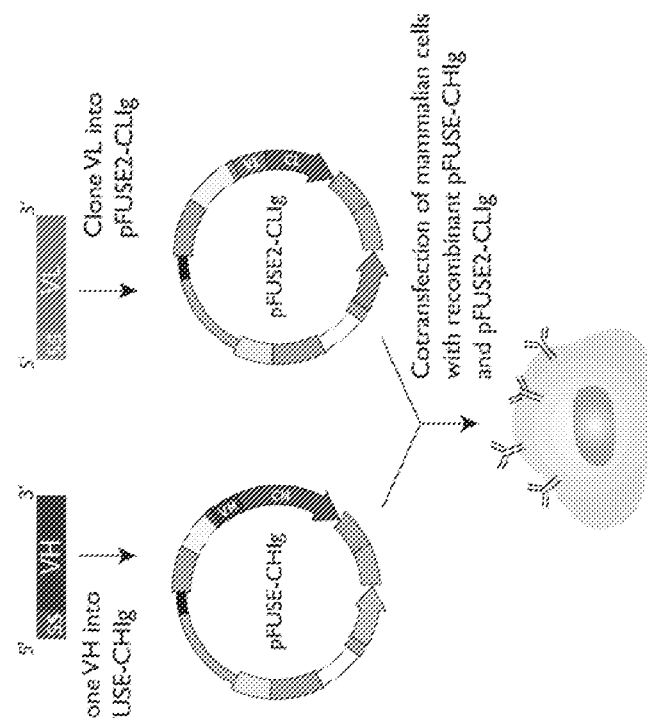
Figure 8C:
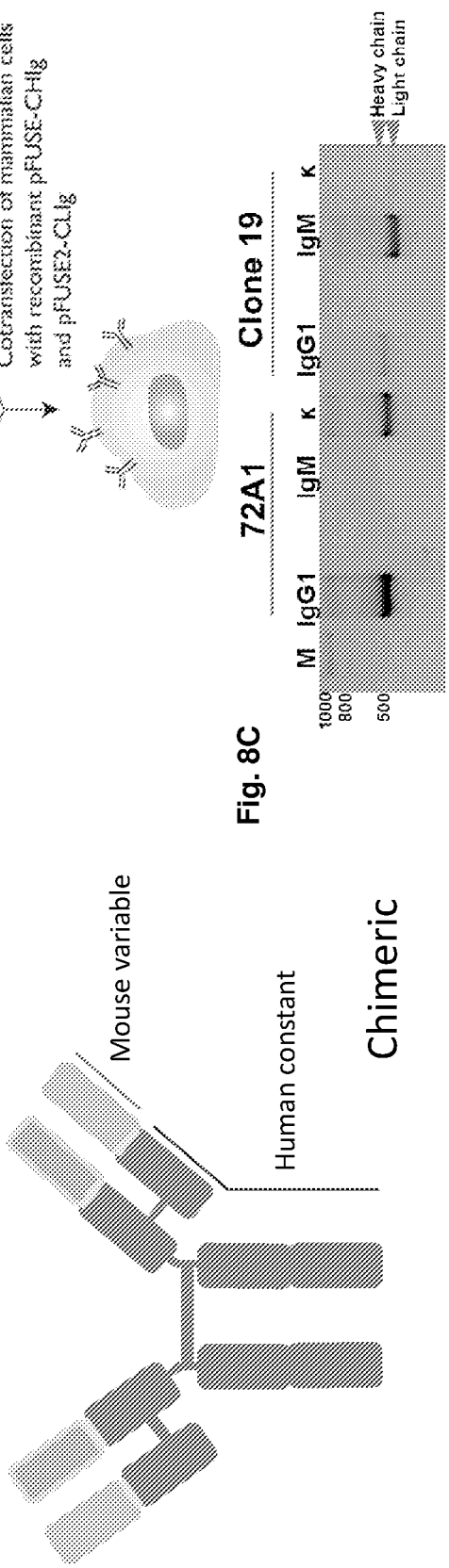

Chimeric gp350 nAbs were constructed according to the diagrams of FIG. 8. First, mouse antibodies against human gp350 were developed, and then the mouse antibody variable region is fused to human constant region, for example, to human IgG. The heavy chain and light chain variable regions of the mouse antibody were cloned into expression vectors such as pFUSE-CHIg and pFUSE2-CLIg vectors, respectively, followed by co-transfection of mammalian cells with recombinant pFUSE-CHIg and pFUSE2-CLIg vectors. The expression vectors were obtained from Invivo-Gen, and the expression was conducted in CHO cells or HEK293 cells, available from ATCC. The construction schemes and expression of heavy and light chains of clone 19 are shown in FIG. 8.

Analysis of VH-VL sequence from the HB168 (nAb-72A1) hybridoma revealed that the hybridoma produced two antibodies: one that is gp350-specific and another that recognizes mineral oil-induced plasmacytoma (MOPC) (57). To further investigate gp350 for additional neutralizing epitopes, the gp350-specific nAb-72A1 VH-VL sequence was used to generate chimeric (mouse/human) recombinant antibodies. Similarly, the VH-VL sequence for the HB20 antibody, which the neutralization analysis above showed to be one of the best nAb, was used to generate chimeric antibody. A negative control chimeric recombinant antibody was generated using VH-VL sequences from the gp350-specific but non-neutralizing HB5 antibody.

Example 9: Development of Antibody-Small Molecule Conjugates (ADCs)

Figure 9:
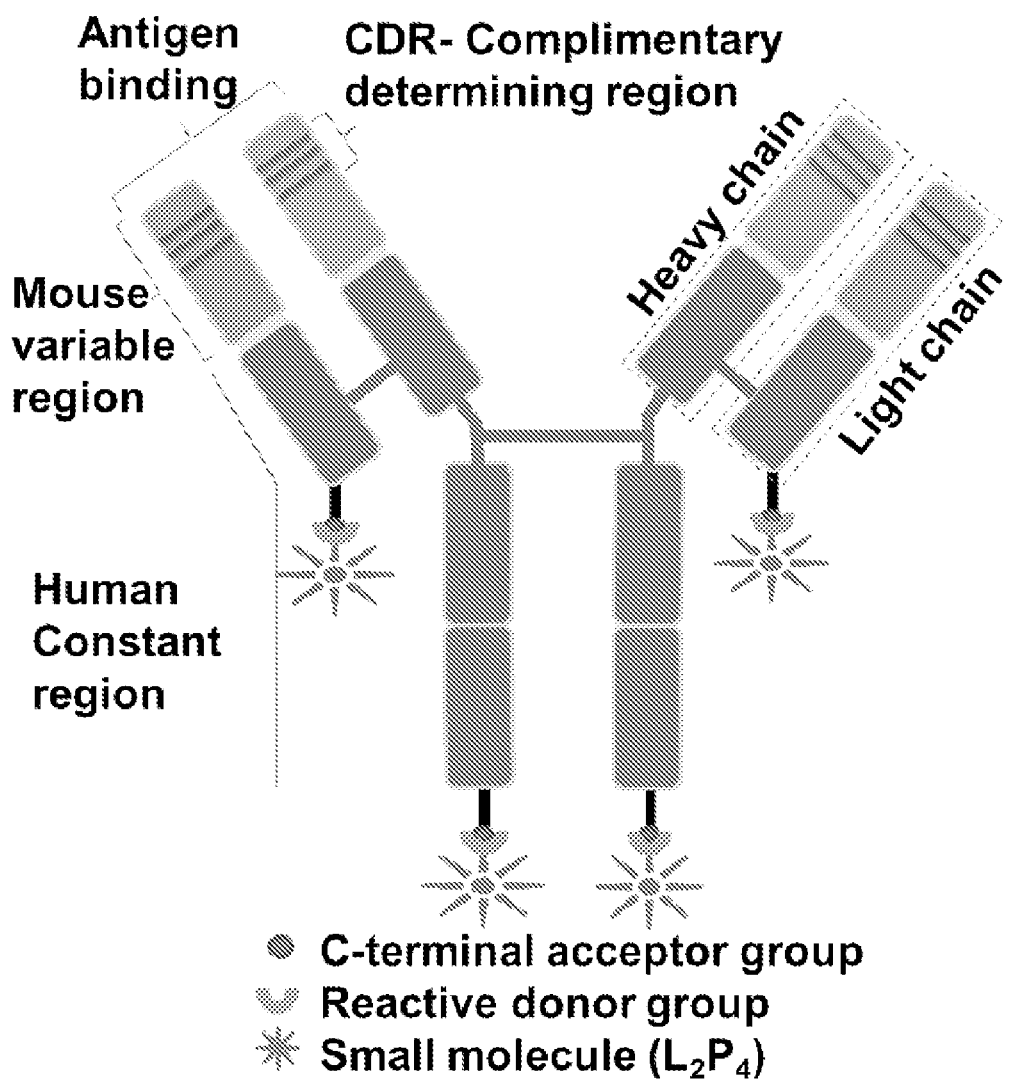
FIG. 9 illustrates an antibody-$L_2P_4$ conjugate.
Figure 10B:
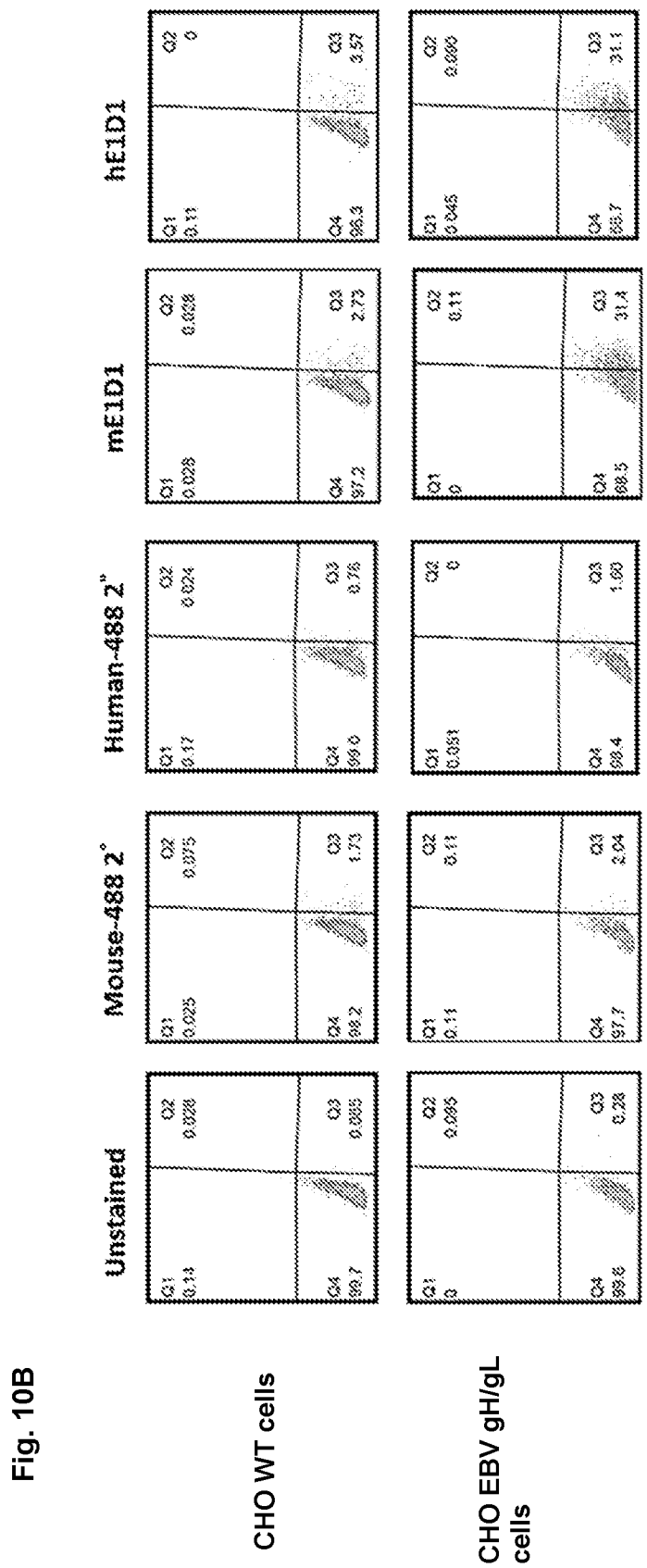
Figure 11B:
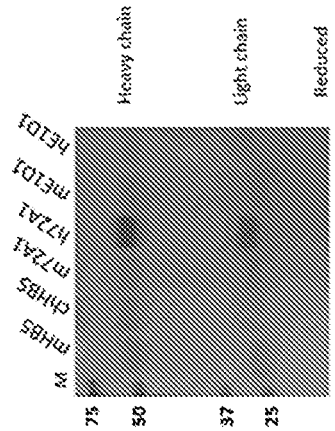
Figure 11A:
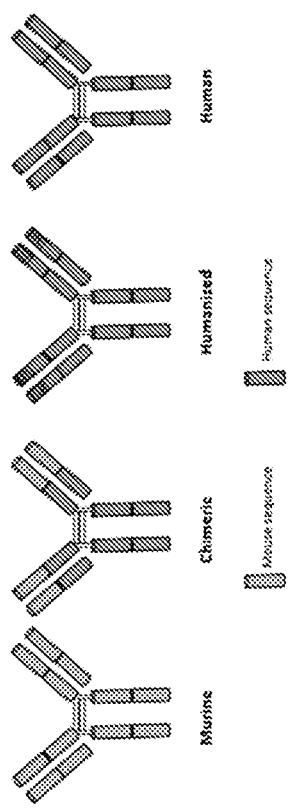
Figure 11E:
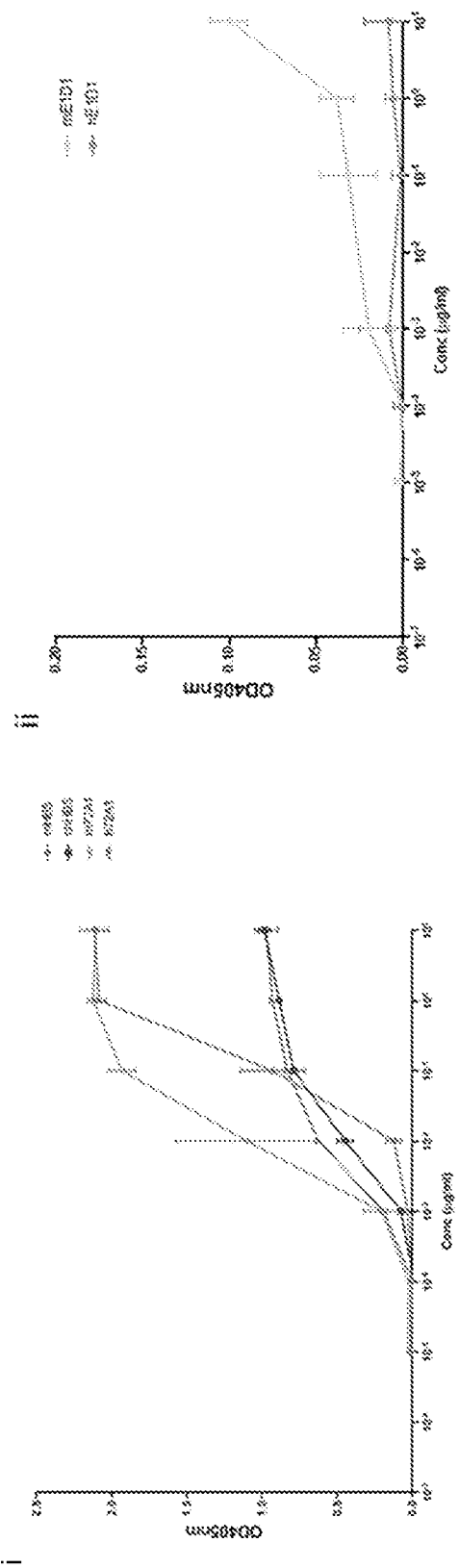
Figure 12B:
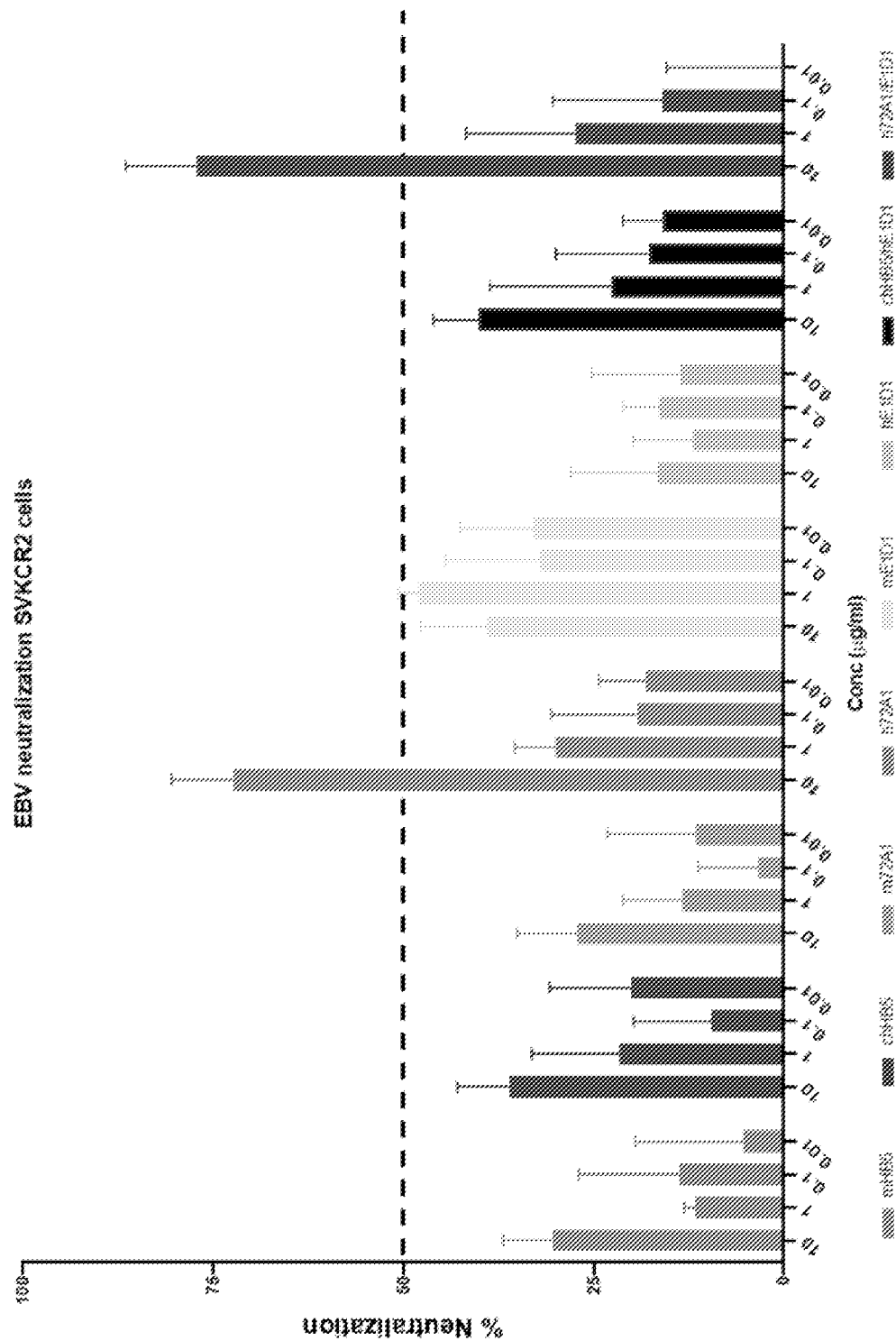
Figure 12C:
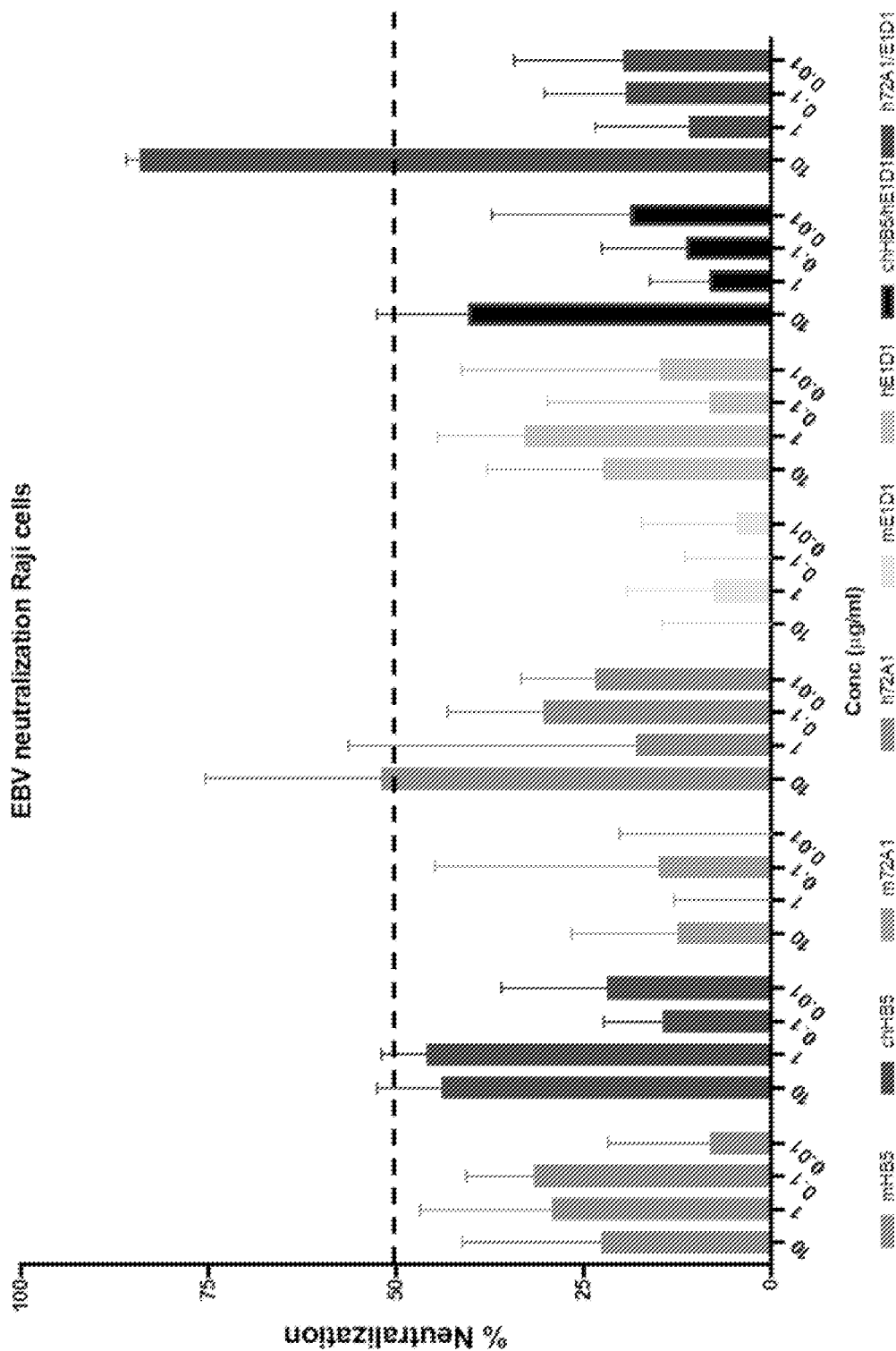

Using small molecule $L_2P_4$ as an example, antibody-small molecule conjugates can be developed as illustrated in FIG. 9. One or more small molecules can be conjugated to the antibody heavy chain or light chain via a reactive donor group and a C-terminal acceptor group. Small molecule $L_2P_4$ was disclosed in the publication by Jiang et al.[40] After validating the function of the purified chimeric gp350 nAbs using ELISA, flow cytometry (FC), and surface plasmon resonance, the nAbs can be conjugated to $L_2P_4$ in a site-specific manner via a Val-Cit dipeptide linker, which releases the active agent upon internalization of the ADC.[41, 42]

Example 10: Efficacy Test of ADCs

To screen for optimal dose and identify the best nAb clone for pre-clinical studies, the ability of the ADC to neutralize EBV in vitro and to protect against PTLD in vivo is tested using a humanized mouse, as described[43,44]. In brief, purified chimeric ADC (or controls: PBS, or isotype-matched non-nAbs) is injected by I.V. into humanized mice, followed by EBV-B95-8-eGFP challenge. Mice are monitored regularly and euthanized upon signs of illness or after a preset limit of 100 days. Routine histology and necropsy are conducted to assess the efficacy of the ADC to protect against EBV infection and PTLD development.

Example 11: Humanization of E1D1

Similar to Example 4, humanized E1D1 antibody was produced and its specificity was compared to mouse E1D1 by flow cytometric analysis (FIG. 10). Humanization of E1D1 did not affect its binding specificity to EBV gH/gL.

Example 12: Biochemical Characterization of Chimeric and Humanized Antibodies

As demonstrated by FIG. 11, murine, chimeric and humanized antibodies purified by affinity and size-exclusion chromatography were analyzed by SDS-PAGE under reducing conditions. Protein band sizes of 50 kDa and 25 kDa corresponding to the heavy and light chain, respectively were observed. ELISA was performed to determine the reactivity of chimeric and humanized antibodies to murine IgG. Soluble EBV gp350 or gH/gL protein was used as the target antigen at 0.5 μg/ml. Plates were incubated with 0.5 μg/ml of primary antibody, followed by three washes. Bound antibodies were detected using HRP-conjugated anti-mouse IgG or anti-human IgG (1:2,000). The chimeric and humanized antibodies did not react to murine IgG. To determine whether chimeric and humanized anti-gp350 retained the ability to recognize linear epitopes on gp350, lysate from CHO WT cells and CHO cell stably expressing gp350 were analyzed by western blot analysis. The chimeric and humanization process of anti-gp350 did not affect the binding affinity of the antibodies to gp350 linear epitopes, as indicated by the protein band observed at ~350 kDa.

ELISA binding of anti-gp350 and anti-gH/gL to soluble gp350 and gH/gL proteins was performed. Soluble EBV gp350 and gH/gL proteins were used as the target antigen at 0.5 μg/ml. 1× phosphate buffered saline (PBS) was used as negative (not shown) control. Bound antibodies were detected using HRP-conjugated anti-mouse or anti-human IgG (1:2,000). The chimeric and humanization process did not affect the ability of anti-gp350 and anti-gH/gL to bind to purified recombinant gp350 and gH/gL proteins, respectively.

Flow cytometric analysis of gp350 and gH/gL specificity was performed. CHO wild type cells and gp350 or gH/gL-expressing CHO cells were stained with primary antibodies, followed by secondary goat anti-mouse or anti-human conjugated to AF488. Unstained cells and cells stained with secondary goat anti-mouse or anti-human conjugated to AF488 alone, were used as negative controls. Binding of chimeric and humanized anti-gp350 or gH/gL to conformational epitopes was comparable to that of the parental murine antibodies.

Example 13: EBV Inhibitory Effects of Anti-Gp350 and Anti-gH/gL nAbs

As shown in FIG. 12, EBV-eGFP was pre-incubated with serial diluted (10-0.01 μg/ml) purified murine, chimeric and humanized anti-gp350 (HB5 and 72A1) and anti-gH/gL (E1D1) followed by incubation for 24 hours with $2.5\times10^5$ HEK 293 (12A) or SVKCR2 cell (12B) or $5\times10^5$ Raji cells (12C). EBV-eGFP+ cells were enumerated using flow cytometry. Murine nAb (mHB5, m72A1 and mE1D1) served as positive controls. h72A1 and chHB5 were able to neutralize EBV infection in both B cells (Raji cells) and CR2+ epithelial cells (HEK 293 and SVKCR2 cells) similar to or better than the murine versions, m72A1 and mHB5.

REFERENCES

The references listed below, and all references cited in the specification are hereby incorporated by reference in their entireties, as if fully set forth herein.

1. Rickinson Aft Kieff E. Epstein-Barr Virus. In: Knipe D M, Howley P M, eds. Fields Virology. Philadelphia: Lippincott, Williams & Wilkins; 2007:2680-2700.
2. Goedert J J, Cote T R, Virgo P, et al. Spectrum of AIDS-associated malignant disorders. Lancet 1998; 351: 1833-9.
3. Cote T R, Biggar R J, Rosenberg P S, et al. Non-Hodgkin's lymphoma among people with AIDS: Incidence, presentation and public health burden. International Journal of Cancer 1998; 73:645-50.
4. Benkerrou M, Jais J P, Leblond V, et al. Anti-B-cell monoclonal antibody treatment of severe posttransplant B-lymphoproliferative disorder: prognostic factors and long-term outcome. Blood 1998; 92:3137-47.
5. Cruz R J, Jr., Ramachandra S, Sasatomi E, et al. Surgical management of gastrointestinal posttransplant lymphoproliferative disorders in liver transplant recipients. Transplantation 2012; 94:417-23.
6. Faro A, Kurland G, Michaels M G, et al. Interferon-alpha affects the immune response in post-transplant lymphoproliferative disorder. Am J Respir Crit Care Med 1996; 153:1442-7.
7. Milpied N, Vasseur B, Parquet N, et al. Humanized anti-CD20 monoclonal antibody (Rituximab) in post transplant B-lymphoproliferative disorder: a retrospective analysis on 32 patients. Ann Oncol 2000; 11 Suppl 1:113-6.
8. Papadopoulos E B, Ladanyi M, Emanuel D, et al. Infusions of donor leukocytes to treat Epstein-Barr virus-associated lymphoproliferative disorders after allogeneic bone marrow transplantation. N Engl J Med 1994; 330: 1185-91.
9. Starzl T E, Holmes J H. Experience in renal transplantation. 1964.
10. Stamatatos L, Morris L, Burton D R, Mascola J R. Neutralizing antibodies generated during natural HIV-1 infection: good news for an HIV-1 vaccine? Nature medicine 2009; 15:866-70.
11. Walker L M, Phogat S K, Chan-Hui P-Y, et al. Broad and potent neutralizing antibodies from an African donor reveal a new HIV-1 vaccine target. Science 2009; 326: 285-9.

12. Sui J, Hwang W C, Perez S, et al. Structural and functional bases for broad-spectrum neutralization of avian and human influenza A viruses. Nature structural & molecular biology 2009; 16:265-73.
13. Han T, Marasco W A. Structural basis of influenza virus neutralization. Annals of the New York Academy of Sciences 2011; 1217:178-90.
14. Wrammert J, Smith K, Miller J, et al. Rapid cloning of high-affinity human monoclonal antibodies against influenza virus. Nature 2008; 453:667-71.
15. Piedimonte G, King K A, Holmgren N L, Bertrand P J, Rodriguez M M, Hirsch R L. A humanized monoclonal antibody against respiratory syncytial virus (palivizumab) inhibits RSV-induced neurogenic-mediated inflammation in rat airways. Pediatr Res 2000; 47:351-6.
16. Glotz D, Chapman J R, Dharnidharka V R, et al. The seville expert workshop for progress in posttransplant lymphoproliferative disorders. Transplantation 2012; 94:784-93.
17. Connolly S A, Jackson J O, Jardetzky T S, Longnecker R. Fusing structure and function: a structural view of the herpesvirus entry machinery: A structural view of herpesvirus entry machinery. Nat Rev Microbiol 2011; 9:369-81.
18. Eisenberg R J, Atanasiu D, Cairns T M, Gallagher J R, Krummenacher C, Cohen G H. Herpes virus fusion and entry: a story with many characters. Viruses 2012; 4:800-32.
19. Henle G, Henle W, Diehl V. Relation of Burkitt's tumor-associated herpes-type virus to infectious mononucleosis. Proceedings of the National Academy of Sciences of the United States of America 1968; 59:94.
20. Cohen J I, Fauci A S, Varmus H, Nabel G J. Epstein-Barr Virus: An Important Vaccine Target for Cancer Prevention. Science Translational Medicine 2011; 3:107fs7-fs7.
21. Khanna R, Sherritt M, Burrows S R. EBV structural antigens, gp350 and gp85, as targets for ex vivo virus-specific CTL during acute infectious mononucleosis: potential use of gp350/gp85 CTL epitopes for vaccine design. The Journal of Immunology 1999; 162:3063-9.
22. Thorley-Lawson D A, Geilinger K. Monoclonal antibodies against the major glycoprotein (gp350/220) of Epstein-Barr virus neutralize infectivity. Proceedings of the National Academy of Sciences of the United States of America 1980; 77:5307-11.
23. Perez E M, Foley J, Tison T, Silva R, Ogembo J G. Novel Epstein-Barr virus-like particles incorporating gH/gL-EBNA1 or gB-LMP2 induce high neutralizing antibody titers and EBV-specific T-cell responses in immunized mice. Oncotarget 2016.
24. Cohen J I. Epstein-barr virus vaccines. Clin Transl Immunology 2015; 4:e32.
25. Biggar R J, Henle W, Fleisher G, Böcker J, Lennette E T, Henle G. Primary Epstein-Barr virus infections in african infants. I. Decline of maternal antibodies and time of infection. International Journal of Cancer 1978; 22:239-43.
26. Biggar R J, Henle G, Böcker J, Lennette E T, Fleisher G, Henle W. Primary Epstein-Barr virus infections in African infants. II. Clinical and serological observations during seroconversion. International Journal of Cancer 1978; 22:244-50.
27. Mold C, Bradt B, Nemerow G, Cooper N. Activation of the alternative complement pathway by EBV and the viral envelope glycoprotein, gp350. The Journal of Immunology 1988; 140:3867-74.
28. Khyatti M, Patel P C, Stefanescu I, Menezes J. Epstein-Barr virus (EBV) glycoprotein gp350 expressed on transfected cells resistant to natural killer cell activity serves as a target antigen for EBV-specific antibody-dependent cellular cytotoxicity. Journal of virology 1991; 65:996-1001.
29. Finerty S, Mackett M, Arrand J R, Watkins P E, Tarlton J, Morgan A J. Immunization of cottontop tamarins and rabbits with a candidate vaccine against the Epstein-Barr virus based on the major viral envelope glycoprotein gp340 and alum. Vaccine 1994; 12:1180-4.
30. Gu S Y, Huang T M, Ruan L, et al. First EBV vaccine trial in humans using recombinant vaccinia virus expressing the major membrane antigen. Dev Biol Stand 1995; 84:171-7.
31. Mok H, Cheng X, Xu Q, et al. Evaluation of Measles Vaccine Virus as a Vector to Deliver Respiratory Syncytial Virus Fusion Protein or Epstein-Barr Virus Glycoprotein gp350. Open Virol J 2012; 6:12-22.
32. Moutschen M, Leonard P, Sokal E M, et al. Phase I/II studies to evaluate safety and immunogenicity of a recombinant gp350 Epstein-Barr virus vaccine in healthy adults. Vaccine 2007; 25:4697-705.
33. Sokal E M, Hoppenbrouwers K, Vandermeulen C, et al. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. Journal of Infectious Diseases 2007; 196:1749-53.
34. Rees L, Tizard E J, Morgan A J, et al. A phase I trial of epstein-barr virus gp350 vaccine for children with chronic kidney disease awaiting transplantation. Transplantation 2009; 88:1025-9.
35. Hague T, Johannessen I, Dombagoda D, et al. A mouse monoclonal antibody against Epstein-Barr virus envelope glycoprotein 350 prevents infection both in vitro and in vivo. J Infect Dis 2006; 194:584-7.
36. Ferrara N, Hillan K J, Gerber H-P, Novotny W. Discovery and development of bevacizumab, an anti-VEGF antibody for treating cancer. Nat Rev Drug Discov 2004; 3:391-400.
37. Hudis C A. Trastuzumab—Mechanism of Action and Use in Clinical Practice. New England Journal of Medicine 2007; 357:39-51.
38. Jonker D J, O'Callaghan C J, Karapetis C S, et al. Cetuximab for the Treatment of Colorectal Cancer. New England Journal of Medicine 2007; 357:2040-8.
39. Dzeng R K, Jha H C, Lu J, Saha A, Banerjee S, Robertson E S. Small molecule growth inhibitors of human oncogenic gammaherpesvirus infected B-cells. Mol Oncol 2015; 9:365-76.
40. Jiang L, Lan R, Huang T, et al. EBNA1-targeted probe for the imaging and growth inhibition of tumours associated with the Epstein-Barr virus. Nature Biomedical Engineering 2017; 1:0042.
41. Dubowchik G M, Firestone R A. Cathepsin B-sensitive dipeptide prodrugs. A model study of structural requirements for efficient release of doxorubicin. Bioorganic & medicinal chemistry letters 1998; 8:3341-6.
42. Senter P D, Sievers E L. The discovery and development of brentuximab vedotin for use in relapsed Hodgkin lymphoma and systemic anaplastic large cell lymphoma. Nature biotechnology 2012; 30:631-7.
43. Hague T, Johannessen I, Dombagoda D, et al. A mouse monoclonal antibody against Epstein-Barr virus envelope glycoprotein 350 prevents infection both in vitro and in vivo. J Infect Dis 2006; 194:584-7.

44. Jangalwe S, Shultz L D, Mathew A, Brehm M A. Improved B cell development in humanized NOD-scid IL2Rgammanull mice transgenically expressing human stem cell factor, granulocyte-macrophage colony-stimulating factor and interleukin-3. Immun Inflamm Dis 2016; 4:427-40.
45. Ogembo J G, Kannan L, Ghiran I, Nicholson-Weller A, Finberg R W, Tsokos G C, Fingeroth J D. 2013. Human complement receptor type 1/CD35 is an Epstein-Barr Virus receptor. Cell Rep 3:371-385.
46. Speck P, Longnecker R. 1999. Epstein-Barr virus (EBV) infection visualized by EGFP expression demonstrates dependence on known mediators of EBV entry. Arch Virol 144:1123-1137.
47. Ogembo J G, Muraswki M R, McGinnes L W, Parcharidou A, Sutiwisesak R, Tison T, Avendano J, Agnani D, Finberg R W, Morrison T G. 2015. A chimeric EBV gp350/220-based VLP replicates the virion B-cell attachment mechanism and elicits long-lasting neutralizing antibodies in mice. Journal of Translational Medicine 13:50.
48. Jones S T, Bendig M M. 1991. Rapid PCR-cloning of full-length mouse immunoglobulin variable regions. Biotechnology (N Y) 9:579.
49. Sela M, Schechter B, Schechter I, Borek F. 1967. Antibodies to Sequential and Conformational Determinants. Cold Spring Harbor Symposia on Quantitative Biology 32:537-545.
50. Herrman M, Muhe J, Quink C, Wang F. 2015. Epstein-Barr Virus gp350 Can Functionally Replace the Rhesus Lymphocryptovirus Major Membrane Glycoprotein and Does Not Restrict Infection of Rhesus Macaques. J Virol 90:1222-1230.
51. Tanner J E, Coincon M, Leblond V, Hu J, Fang J M, Sygusch J, Alfieri C. 2015. Peptides designed to spatially depict the Epstein-Barr virus major virion glycoprotein gp350 neutralization epitope elicit antibodies that block virus-neutralizing antibody 72A1 interaction with the native gp350 molecule. J Virol 89:4932-4941.
52. Sashihara J, Burbelo P D, Savoldo B, Pierson T C, Cohen J I. 2009. Human antibody titers to Epstein-Barr Virus (EBV) gp350 correlate with neutralization of infectivity better than antibody titers to EBV gp42 using a rapid flow cytometry-based EBV neutralization assay. Virology 391: 249-256.
53. Qualtiere L F, Decoteau J F, Hassan Nasr-el-Din M. 1987. Epitope mapping of the major Epstein-Barr virus outer envelope glycoprotein gp350/220. J Gen Virol 68 (Pt 2):535-543.
54. Nemerow G R, et al. 1987. Identification of Gp350 as the Viral Glycoprotein Mediating Attachment of Epstein-Barr-Virus (Ebv) to the Ebv/C3d Receptor of B-Cells—Sequence Homology of Gp350 and C3-Complement Fragment C3d. Journal of Virology 61:1416-1420.
55. Nemerow G R, Houghten R A, Moore M D, Cooper N R. 1989. Identification of an epitope in the major envelope protein of Epstein-Barr virus that mediates viral binding to the B lymphocyte EBV receptor (CR2). Cell 56:369-377.
56. Zhang P F, Klutch M, Armstrong G, Qualtiere L, Pearson G, Marcus-Sekura C J. 1991. Mapping of the epitopes of Epstein-Barr virus gp350 using monoclonal antibodies and recombinant proteins expressed in *Escherichia coli* defines three antigenic determinants. J Gen Virol 72 (Pt 11):2747-2755.
57. Tanner J, Whang Y, Sample J, Sears A, Kieff E. 1988. Soluble gp350/220 and deletion mutant glycoproteins block Epstein-Barr virus adsorption to lymphocytes. J Virol 62:4452-4464.
58. Urquiza M, Lopez R, Patino H, Rosas J E, Patarroyo M E. 2005. Identification of three gp350/220 regions involved in Epstein-Barr virus invasion of host cells. J Biol Chem 280:35598-35605.
59. Szakonyi G, Klein M G, Hannan J P, Young K A, Ma R Z, Asokan R, Holers V M, Chen X S. 2006. Structure of the Epstein-Barr virus major envelope glycoprotein. Nat Struct Mol Biol 13:996-1001.
60. Sitompul L S, Widodo N, Djati M S, Utomo D H. 2012. Epitope mapping of gp350/220 conserved domain of epstein barr virus to develop nasopharyngeal carcinoma (npc) vaccine. Bioinformation 8:479-482.
61. Balfour H H, Jr. 2014. Progress, prospects, and problems in Epstein-Barr virus vaccine development. Curr Opin Virol 6C:1-5.
62. Henle G, Henle W. 1979. The virus as the etiologic agent of infectious mononucleosis, p 297-320, The Epstein-Barr Virus. Springer.
63. Luzuriaga K, Sullivan J L. 2010. Infectious mononucleosis. N Engl J Med 362:1993-2000.
64. Cui X, Cao Z, Chen Q, Arjunaraja S, Snow A L, Snapper C M. 2016. Rabbits immunized with Epstein-Barr virus gH/gL or gB recombinant proteins elicit higher serum virus neutralizing activity than gp350. Vaccine.
65. Fingeroth J D, Weis J J, Tedder T F, Strominger J L, Biro P A, Fearon D T. 1984. Epstein-Barr virus receptor of human B lymphocytes is the C3d receptor CR2. Proc Natl Acad Sci USA 81:4510-4514.
66. Tanner J, Weis J, Fearon D, Whang Y, Kieff E. 1987. Epstein-Barr virus gp350/220 binding to the B lymphocyte C3d receptor mediates adsorption, capping, and endocytosis. Cell 50:203-213.
67. Weiss E R, Alter G, Ogembo J G, Henderson J L, Tabak B, Bakis Y, Somasundaran M, Garber M, Selin L, Luzuriaga K. 2017. High Epstein-Barr Virus Load and Genomic Diversity Are Associated with Generation of gp350-Specific Neutralizing Antibodies following Acute Infectious Mononucleosis. J Virol 91.
68. Hoffman G J, Lazarowitz S G, Hayward S D. 1980. Monoclonal antibody against a 250,000-dalton glycoprotein of Epstein-Barr virus identifies a membrane antigen and a neutralizing antigen. Proc Natl Acad Sci USA 77:2979-2983.
69. Thorley-Lawson D A, Geilinger K. 1980. Monoclonal antibodies against the major glycoprotein (gp350/220) of Epstein-Barr virus neutralize infectivity. Proc Natl Acad Sci USA 77:5307-5311.
70. Alfarano C, et al. 2005. The Biomolecular Interaction Network Database and related tools 2005 update. Nucleic Acids Res 33:D418-424.
71. Thorley-Lawson D A, Poodry C A. 1982. Identification and isolation of the main component (gp350-gp220) of Epstein-Barr virus responsible for generating neutralizing antibodies in vivo. J Virol 43:730-6.
72. Cohen J I. 2000. Epstein-Barr virus infection. New England Journal of Medicine 343:481-492.
73. Chen J, Sathiyamoorthy K, Zhang X, Schaller S, Perez White B E, Jardetzky T S, Longnecker R. 2018. Ephrin receptor A2 is a functional entry receptor for Epstein-Barr virus. Nat Microbiol 3:172-180.
74. Zhang H, et al. 2018. Ephrin receptor A2 is an epithelial cell receptor for Epstein-Barr virus entry. Nat Microbiol 3:1-8.

75. Chesnokova L S, et al. 2009. Fusion of epithelial cells by Epstein-Barr virus proteins is triggered by binding of viral glycoproteins gHgL to integrins αvβ6 or αvβ8. Proceedings of the National Academy of Sciences 106:20464-20469.
76. Tugizov S M, et al. 2003. Epstein-Barr virus infection of polarized tongue and nasopharyngeal epithelial cells. Nat Med 9:307-14.
77. Babcock G J, Decker L L, Volk M, Thorley-Lawson D A. 1998. EBV persistence in memory B cells in vivo. Immunity 9:395-404.
78. Bu W, et al. 2019. Immunization with Components of the Viral Fusion Apparatus Elicits 686 Antibodies That Neutralize Epstein-Barr Virus in B Cells and Epithelial Cells. Immunity 687 doi:10.1016/j.immuni.2019.03.010.
79. Mulama D H, et al. 2019. A multivalent Kaposi sarcoma-associated herpesvirus-like particle vaccine capable of eliciting high titers of neutralizing antibodies in immunized rabbits. Vaccine.
80. Broering T J, Garrity K A, Boatright N K, Sloan S E, Sandor F, Thomas W D, Jr., Szabo G, Finberg R W, Ambrosino D M, Babcock G J. 2009. Identification and characterization of broadly neutralizing human monoclonal antibodies directed against the E2 envelope glycoprotein of hepatitis C virus. J Virol 83:12473-82.
81. Pei J, Kim B-H, Grishin N V. 2008. PROMALS3D: a tool for multiple protein sequence and structure alignments. Nucleic Acids Research 36:2295-2300.
82. Brochet X, Lefranc M P, Giudicelli V. 2008. IMGT/V-QUEST: the highly customized and integrated system for I G and T R standardized V-J and V-D-J sequence analysis. Nucleic Acids Res 36:W503-8.
83. Donaldson J M, Zer C, Avery K N, Bzymek K P, Horne D A, Williams J C. 2013. Identification and grafting of a unique peptide-binding site in the Fab framework of monoclonal antibodies. Proc Natl Acad Sci USA 110: 17456-61.
84. Chiuppesi F, Wussow F, Johnson E, Bian C, Zhuo M, Rajakumar A, Barry P A, Britt W J, Chakraborty R, Diamond D J. 2015. Vaccine-Derived Neutralizing Antibodies to the Human Cytomegalovirus gH/gL Pentamer Potently Block Primary Cytotrophoblast Infection. J Virol 89:11884-98.
85. Tanner J E, Hu J, Alfieri C. 2018. Construction and Characterization of a Humanized Anti-Epstein-Barr Virus gp350 Antibody with Neutralizing Activity in Cell Culture. Cancers (Basel) 10.

The invention claimed is:

1. An antibody or an antigen-binding fragment thereof that binds to Epstein-Barr virus (EBV) glycoprotein (gp) 350 or glycoprotein 220; and comprises a heavy chain comprising a sequence at least 95% identical to SEQ ID NOs: 179 or 184 and a light chain comprising a sequence at least 95% identical to SEQ ID NOs: 181 or 186.

2. The antibody or the antigen-binding fragment thereof of claim 1, wherein the antibody or the immunogenic fragment thereof binds to a fragment of gp350 comprising residues 1-101, 102-201, or 402-501 of SEQ ID NO: 182.

3. The antibody of claim 1, wherein the antibody is a monoclonal antibody.

4. The antibody of claim 1, wherein the antibody is a chimeric antibody, a humanized antibody or a human antibody.

5. The antibody of claim 4, wherein the antibody is humanized 72A1 or humanized E1D1.

6. An engineered immunogenic peptide comprising one or more fragments of gp350, wherein each fragment has an amino acid sequence identical to or sharing at least 60% similarity to residues 1-101, 102-201, or 402-501 of SEQ ID NO: 182.

7. The engineered immunogenic peptide of claim 6, further comprising a known immunogenic peptide.

8. An antibody-small molecule conjugate comprising:
an antibody or an antigen-binding fragment thereof that binds to a fragment of EBV gp350 or EBV gp220 comprising residues 1-101, 102-201, or 402-501 of SEQ ID NO: 182; and
a small molecule having an anti-proliferative activity against EBV-transformed cells,
wherein the small molecule is conjugated to the antibody or the antigen-binding fragment thereof,
wherein the antibody or antigen-binding fragment thereof comprises a heavy chain comprising a sequence at least 95% identical to SEQ ID NOs: 179 or 184 and a light chain comprising a sequence at least 95% identical to SEQ ID NOs: 181 or 186.

9. The conjugate of claim 8, wherein the antibody is a monoclonal antibody.

10. The conjugate of claim 9, wherein the antibody is a chimeric antibody, a humanized antibody or a human antibody.

11. A pharmaceutical composition comprising the antibody or the antigen-binding fragment thereof of claim 2.

12. A method of neutralizing EBV infection comprising administering to a subject infected with EBV a therapeutically effective amount of the antibody or the antigen-binding fragment thereof of claim 2.

13. A method of preventing EBV infection comprising administering to a subject at an elevated risk of EBV infection a therapeutically effective amount of the antibody or the antigen-binding fragment thereof of claim 2.

14. A method of immunizing or vaccinating a subject against EBV infection comprising administering to the subject a therapeutically effective amount of the antibody or the antigen-binding fragment thereof of claim 2.

15. A pharmaceutical composition comprising the immunogenic peptide of claim 6.

16. A method of neutralizing EBV infection comprising administering to a subject infected with EBV a therapeutically effective amount of the immunogenic peptide of claim 6.

17. A method of preventing EBV infection comprising administering to a subject at an elevated risk of EBV infection a therapeutically effective amount of the immunogenic peptide of claim 6.

18. A method of immunizing or vaccinating a subject against EBV infection comprising administering to the subject a therapeutically effective amount of the immunogenic peptide of claim 6.

19. The antibody of claim 1, wherein the heavy chain comprises SEQ ID NOs: 179 or 184.

20. The antibody of claim 19, wherein the light chain comprises SEQ ID NOs: 181 or 186.

21. The engineered immunogenic peptide of claim 7, wherein the known immunogenic peptide is a keyhole limpet hemocyanin (KLH) peptide.

* * * * *

SEQUENCE LISTING

<160> NUMBER OF SEQ ID NOS: 186

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 7
<212> TYPE: PRT
<213> ORGANISM: Artificial Sequence
<220> FEATURE:
<223> OTHER INFORMATION: VH CDR-1 72A1

<400> SEQUENCE: 4

Gly Ser Ser Phe Thr Asp Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: VH CDR-1 HB-1

<400> SEQUENCE: 5

Gly Phe Leu Leu Thr Thr Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: VH CDR-1 HB-2

<400> SEQUENCE: 6

Gly Tyr Thr Phe Thr Ala Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: VH CDR-1 HB-3

<400> SEQUENCE: 7

Gly Tyr Thr Phe Ala Ser Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: VH CDR-1 HB-5

<400> SEQUENCE: 8

Gly Tyr Thr Phe Thr Asn His
1               5

<210> SEQ ID NO 9
<211> LENGTH: 7
<212> TYPE: PRT
<213> ORGANISM: Artificial Sequence
<220> FEATURE:
<223> OTHER INFORMATION: VH CDR-1 HB-6

<400> SEQUENCE: 9

Gly Tyr Thr Phe Thr Asp Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: VH CDR-1 HB-7

<400> SEQUENCE: 10

Gly Tyr Thr Phe Thr Asp Tyr
1               5

<210> SEQ ID NO 11
<211> LENGTH: 7
<212> TYPE: PRT
<213> ORGANISM: Artificial Sequence
<220> FEATURE:
<223> OTHER INFORMATION: VH CDR-1 HB-8

<400> SEQUENCE: 11

Gly Tyr Ser Phe Thr Asn Tyr
1               5

```
<210> SEQ ID NO 12
<211> LENGTH: 7
<212> TYPE: PRT
<213> ORGANISM: Artificial Sequence
<220> FEATURE:
<223> OTHER INFORMATION: VH CDR-1 HB-9

<400> SEQUENCE: 12

Gly Phe Thr Phe Ser Ser Tyr
1               5

<210> SEQ ID NO 13
<211> LENGTH: 7
<212> TYPE: PRT
<213> ORGANISM: Artificial Sequence
<220> FEATURE:
<223> OTHER INFORMATION: VH CDR-1 HB-10

<400> SEQUENCE: 13

Gly Tyr Thr Phe Thr Ser Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: VH CDR-1 HB-11

<400> SEQUENCE: 14

Gly Asp Ser Ile Thr Ser Gly
1               5

<210> SEQ ID NO 15
<211> LENGTH: 7
<212> TYPE: PRT
<213> ORGANISM: Artificial Sequence
<220> FEATURE:
<223> OTHER INFORMATION: VH CDR-1 HB-12

<400> SEQUENCE: 15

Gly Tyr Thr Phe Thr Asn Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: VH CDR-1 HB-14

<400> SEQUENCE: 16

Gly Tyr Thr Phe Thr Asp Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: VH CDR-1 HB-17

<400> SEQUENCE: 17

Gly Tyr Thr Phe Thr Ser Tyr
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: VH CDR-1 HB-20

<400> SEQUENCE: 18

Gly Tyr Thr Phe Thr Ser Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: VH CDR-1 HB-22

<400> SEQUENCE: 19

Gly Phe Ser Leu Thr Asn Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: VH CDR-2 72A1

<400> SEQUENCE: 20

Ile Asn Pro Tyr Asn Gly Gly
1               5

<210> SEQ ID NO 21
<211> LENGTH: 6
<212> TYPE: PRT
<213> ORGANISM: Artificial Sequence
<220> FEATURE:
<223> OTHER INFORMATION: VH CDR-2 HB-1

<400> SEQUENCE: 21

Ile Trp Ala Gly Gly Ser
1               5

<210> SEQ ID NO 22
<211> LENGTH: 7
<212> TYPE: PRT
<213> ORGANISM: Artificial Sequence
<220> FEATURE:
<223> OTHER INFORMATION: VH CDR-2 HB-2

<400> SEQUENCE: 22

Ile Asn Tyr Lys Thr Gly Glu
1               5

<210> SEQ ID NO 23
<211> LENGTH: 7
<212> TYPE: PRT
<213> ORGANISM: Artificial Sequence
<220> FEATURE:
<223> OTHER INFORMATION: VH CDR-2 HB-3

<400> SEQUENCE: 23

Ile Asn Pro Asn Asn Gly His
1               5

<210> SEQ ID NO 24
```

```
<211> LENGTH: 7
<212> TYPE: PRT
<213> ORGANISM: Artificial Sequence
<220> FEATURE:
<223> OTHER INFORMATION: VH CDR-2 HB-5

<400> SEQUENCE: 24

Ile Asn Pro Tyr Asn Asp Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: VH CDR-2 HB-6

<400> SEQUENCE: 25

Ile Asn Thr Arg Thr Gly Glu
1               5

<210> SEQ ID NO 26
<211> LENGTH: 7
<212> TYPE: PRT
<213> ORGANISM: Artificial Sequence
<220> FEATURE:
<223> OTHER INFORMATION: VH CDR-2 HB-7

<400> SEQUENCE: 26

Ile Ser Pro Gly Arg Ser Gly
1               5

<210> SEQ ID NO 27
<211> LENGTH: 7
<212> TYPE: PRT
<213> ORGANISM: Artificial Sequence
<220> FEATURE:
<223> OTHER INFORMATION: VH CDR-2 HB-8

<400> SEQUENCE: 27

Ile Asn Thr Tyr Thr Gly Glu
1               5

<210> SEQ ID NO 28
<211> LENGTH: 7
<212> TYPE: PRT
<213> ORGANISM: Artificial Sequence
<220> FEATURE:
<223> OTHER INFORMATION: VH CDR-2 HB-9

<400> SEQUENCE: 28

Ile Ser Ser Gly Gly Ser Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: VH CDR-2 HB-10

<400> SEQUENCE: 29

Ile Asn Pro Ser Asn Gly His
1               5

<210> SEQ ID NO 30
<211> LENGTH: 6
```

<212> TYPE: PRT
<213> ORGANISM: Artificial Sequence
<220> FEATURE:
<223> OTHER INFORMATION: VH CDR-2 HB-11

<400> SEQUENCE: 30

Ile Ser Tyr Ser Gly Ser
1               5

<210> SEQ ID NO 31
<211> LENGTH: 7
<212> TYPE: PRT
<213> ORGANISM: Artificial Sequence
<220> FEATURE:
<223> OTHER INFORMATION: VH CDR-2 HB-12

<400> SEQUENCE: 31

Ile Asn Pro Asn Asn Gly His
1               5

<210> SEQ ID NO 32
<211> LENGTH: 7
<212> TYPE: PRT
<213> ORGANISM: Artificial Sequence
<220> FEATURE:
<223> OTHER INFORMATION: VH CDR-2 HB-14

<400> SEQUENCE: 32

Ile His Pro Arg Arg Gly Gly
1               5

<210> SEQ ID NO 33
<211> LENGTH: 7
<212> TYPE: PRT
<213> ORGANISM: Artificial Sequence
<220> FEATURE:
<223> OTHER INFORMATION: VH CDR-2 HB-17

<400> SEQUENCE: 33

Ile Asn Pro Asn Asn Gly His
1               5

<210> SEQ ID NO 34
<211> LENGTH: 7
<212> TYPE: PRT
<213> ORGANISM: Artificial Sequence
<220> FEATURE:
<223> OTHER INFORMATION: VH CDR-2 HB-20

<400> SEQUENCE: 34

Ile Asn Pro Thr Asn Gly His
1               5

<210> SEQ ID NO 35
<211> LENGTH: 6
<212> TYPE: PRT
<213> ORGANISM: Artificial Sequence
<220> FEATURE:
<223> OTHER INFORMATION: VH CDR-2 HB-22

<400> SEQUENCE: 35

Ile Trp Ser Asp Gly Ser
1               5

<210> SEQ ID NO 36
<211> LENGTH: 12
<212> TYPE: PRT

```
<213> ORGANISM: Artificial Sequence
<220> FEATURE:
<223> OTHER INFORMATION: VH CDR-3 72A1

<400> SEQUENCE: 36

Gly Gly Leu Arg Arg Val Asn Trp Phe Ala Tyr Trp
1               5                   10

<210> SEQ ID NO 37
<211> LENGTH: 14
<212> TYPE: PRT
<213> ORGANISM: Artificial Sequence
<220> FEATURE:
<223> OTHER INFORMATION: VH CDR-3 HB-1

<400> SEQUENCE: 37

Arg Asp Arg Gly Tyr Gly Tyr Leu Tyr Ala Met Asp Tyr Trp
1               5                   10

<210> SEQ ID NO 38
<211> LENGTH: 9
<212> TYPE: PRT
<213> ORGANISM: Artificial Sequence
<220> FEATURE:
<223> OTHER INFORMATION: VH CDR-3 HB-2

<400> SEQUENCE: 38

Pro Tyr Gly Tyr Ala Leu Asp Tyr Trp
1               5

<210> SEQ ID NO 39
<211> LENGTH: 12
<212> TYPE: PRT
<213> ORGANISM: Artificial Sequence
<220> FEATURE:
<223> OTHER INFORMATION: VH CDR-3 HB-3

<400> SEQUENCE: 39

Arg Asn Leu Tyr Tyr Tyr Gly Arg Pro Asp Tyr Trp
1               5                   10

<210> SEQ ID NO 40
<211> LENGTH: 14
<212> TYPE: PRT
<213> ORGANISM: Artificial Sequence
<220> FEATURE:
<223> OTHER INFORMATION: VH CDR-3 HB-5

<400> SEQUENCE: 40

Arg Ser Glu Gly Trp Leu Arg Arg Gly Ala Trp Phe Ala Tyr
1               5                   10

<210> SEQ ID NO 41
<211> LENGTH: 9
<212> TYPE: PRT
<213> ORGANISM: Artificial Sequence
<220> FEATURE:
<223> OTHER INFORMATION: VH CDR-3 HB-6

<400> SEQUENCE: 41

Pro Tyr Gly Tyr Ala Leu Asp Tyr Trp
1               5

<210> SEQ ID NO 42
<211> LENGTH: 11
<212> TYPE: PRT
<213> ORGANISM: Artificial Sequence
```

```
<220> FEATURE:
<223> OTHER INFORMATION: VH CDR-3 HB-7

<400> SEQUENCE: 42

Arg Tyr Gly His Pro Ser Tyr Leu Asp Val Trp
1               5                   10

<210> SEQ ID NO 43
<211> LENGTH: 15
<212> TYPE: PRT
<213> ORGANISM: Artificial Sequence
<220> FEATURE:
<223> OTHER INFORMATION: VH CDR-3 HB-8

<400> SEQUENCE: 43

Arg Tyr Tyr Tyr Gly Ser Val Tyr Ser Ala Trp Phe Ala Tyr Trp
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: VH CDR-3 HB-9

<400> SEQUENCE: 44

Arg Glu Asp Phe Tyr Tyr Gly Ser Ser Tyr Gly Phe Phe Asp Val Trp
1               5                   10                  15

<210> SEQ ID NO 45
<211> LENGTH: 12
<212> TYPE: PRT
<213> ORGANISM: Artificial Sequence
<220> FEATURE:
<223> OTHER INFORMATION: VH CDR-3 HB-10

<400> SEQUENCE: 45

Arg Asn Leu Tyr Tyr Tyr Gly Arg Pro Asp Tyr Trp
1               5                   10

<210> SEQ ID NO 46
<211> LENGTH: 14
<212> TYPE: PRT
<213> ORGANISM: Artificial Sequence
<220> FEATURE:
<223> OTHER INFORMATION: VH CDR-3 HB-11

<400> SEQUENCE: 46

Arg Gly Asn Gly Gly Asn Tyr Asp Trp Tyr Phe Asp Val Trp
1               5                   10

<210> SEQ ID NO 47
<211> LENGTH: 12
<212> TYPE: PRT
<213> ORGANISM: Artificial Sequence
<220> FEATURE:
<223> OTHER INFORMATION: VH CDR-3 HB-12

<400> SEQUENCE: 47

Arg Asn Leu Tyr Tyr Tyr Gly Arg Pro Asp Tyr Trp
1               5                   10

<210> SEQ ID NO 48
<211> LENGTH: 11
<212> TYPE: PRT
<213> ORGANISM: Artificial Sequence
<220> FEATURE:
```

```
<223> OTHER INFORMATION: VH CDR-3 HB-14

<400> SEQUENCE: 48

Arg Tyr Gly Tyr Pro Trp Tyr Phe Asp Val Trp
1               5                   10

<210> SEQ ID NO 49
<211> LENGTH: 12
<212> TYPE: PRT
<213> ORGANISM: Artificial Sequence
<220> FEATURE:
<223> OTHER INFORMATION: VH CDR-3 HB-17

<400> SEQUENCE: 49

Arg Asn Leu Phe Tyr Tyr Ser Arg Pro Asp Tyr Trp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: VH CDR-3 HB-20

<400> SEQUENCE: 50

Arg Asn Leu Tyr Tyr Tyr Gly Arg Pro Asp Tyr Trp
1               5                   10

<210> SEQ ID NO 51
<211> LENGTH: 15
<212> TYPE: PRT
<213> ORGANISM: Artificial Sequence
<220> FEATURE:
<223> OTHER INFORMATION: VH CDR-3 HB-22

<400> SEQUENCE: 51

Arg Asn Tyr Tyr Gly Asn Ser Tyr Pro Ala Trp Phe Ala Tyr Trp
1               5                   10                  15

<210> SEQ ID NO 52
<211> LENGTH: 9
<212> TYPE: PRT
<213> ORGANISM: Artificial Sequence
<220> FEATURE:
<223> OTHER INFORMATION: VL CDR-1 72A1

<400> SEQUENCE: 52

Thr Gly Ala Val Thr Thr Ser Asn Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: VL CDR-1 HB-1

<400> SEQUENCE: 53

Gln Asn Val Gly Thr Asn
1               5

<210> SEQ ID NO 54
<211> LENGTH: 5
<212> TYPE: PRT
<213> ORGANISM: Artificial Sequence
<220> FEATURE:
<223> OTHER INFORMATION: VL CDR-1 HB-2
```

```
<400> SEQUENCE: 54

Ser Ser Val Asn Tyr
1               5

<210> SEQ ID NO 55
<211> LENGTH: 6
<212> TYPE: PRT
<213> ORGANISM: Artificial Sequence
<220> FEATURE:
<223> OTHER INFORMATION: VL CDR-1 HB-3

<400> SEQUENCE: 55

Gln Asp Ile Gly Asn Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: VL CDR-1 HB-5

<400> SEQUENCE: 56

Gln Ser Ile Gly Thr Ser
1               5

<210> SEQ ID NO 57
<211> LENGTH: 5
<212> TYPE: PRT
<213> ORGANISM: Artificial Sequence
<220> FEATURE:
<223> OTHER INFORMATION: VL CDR-1 HB-6

<400> SEQUENCE: 57

Ser Ser Val Asn Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: VL CDR-1 HB-7

<400> SEQUENCE: 58

Gln Ser Val Gly Asn Ala
1               5

<210> SEQ ID NO 59
<211> LENGTH: 11
<212> TYPE: PRT
<213> ORGANISM: Artificial Sequence
<220> FEATURE:
<223> OTHER INFORMATION: VL CDR-1 HB-8

<400> SEQUENCE: 59

Gln Ser Ile Val His Ser Asn Gly Asn Thr Tyr
1               5                   10

<210> SEQ ID NO 60
<211> LENGTH: 11
<212> TYPE: PRT
<213> ORGANISM: Artificial Sequence
<220> FEATURE:
<223> OTHER INFORMATION: VL CDR-1 HB-9
```

<400> SEQUENCE: 60

Gln Ser Ile Val His Ser Asn Gly Asn Thr Tyr
1               5                   10

<210> SEQ ID NO 61
<211> LENGTH: 6
<212> TYPE: PRT
<213> ORGANISM: Artificial Sequence
<220> FEATURE:
<223> OTHER INFORMATION: VL CDR-1 HB-10

<400> SEQUENCE: 61

Gln Asp Ile Gly Asn Tyr
1               5

<210> SEQ ID NO 62
<211> LENGTH: 5
<212> TYPE: PRT
<213> ORGANISM: Artificial Sequence
<220> FEATURE:
<223> OTHER INFORMATION: VL CDR-1 HB-11

<400> SEQUENCE: 62

Ser Ser Val Asn Phe
1               5

<210> SEQ ID NO 63
<211> LENGTH: 11
<212> TYPE: PRT
<213> ORGANISM: Artificial Sequence
<220> FEATURE:
<223> OTHER INFORMATION: VL CDR-1 HB-12

<400> SEQUENCE: 63

Gln Ser Leu Val His Ser Asn Gly Asn Thr Tyr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: VL CDR-1 HB-14

<400> SEQUENCE: 64

Gln Ser Ile Val His Asp Asn Gly Asn Thr Tyr
1               5                   10

<210> SEQ ID NO 65
<211> LENGTH: 6
<212> TYPE: PRT
<213> ORGANISM: Artificial Sequence
<220> FEATURE:
<223> OTHER INFORMATION: VL CDR-1 HB-17

<400> SEQUENCE: 65

Gln Asp Ile Gly Asn Tyr
1               5

<210> SEQ ID NO 66
<211> LENGTH: 6
<212> TYPE: PRT
<213> ORGANISM: Artificial Sequence
<220> FEATURE:
<223> OTHER INFORMATION: VL CDR-1 HB-20

<400> SEQUENCE: 66

```
Gln Asp Ile Gly Asn Tyr
1               5

<210> SEQ ID NO 67
<211> LENGTH: 11
<212> TYPE: PRT
<213> ORGANISM: Artificial Sequence
<220> FEATURE:
<223> OTHER INFORMATION: VL CDR-1 HB-22

<400> SEQUENCE: 67

Gln Ser Ile Val His Ser Asn Gly Asn Thr Tyr
1               5                   10

<210> SEQ ID NO 68
<211> LENGTH: 3
<212> TYPE: PRT
<213> ORGANISM: Artificial Sequence
<220> FEATURE:
<223> OTHER INFORMATION: VL CDR-2 72A1

<400> SEQUENCE: 68

Gly Thr Asn
1

<210> SEQ ID NO 69
<211> LENGTH: 3
<212> TYPE: PRT
<213> ORGANISM: Artificial Sequence
<220> FEATURE:
<223> OTHER INFORMATION: VL CDR-2 HB-1

<400> SEQUENCE: 69

Ser Thr Asp
1

<210> SEQ ID NO 70
<211> LENGTH: 3
<212> TYPE: PRT
<213> ORGANISM: Artificial Sequence
<220> FEATURE:
<223> OTHER INFORMATION: VL CDR-2 HB-2

<400> SEQUENCE: 70

Ala Thr Ser
1

<210> SEQ ID NO 71
<211> LENGTH: 3
<212> TYPE: PRT
<213> ORGANISM: Artificial Sequence
<220> FEATURE:
<223> OTHER INFORMATION: VL CDR-2 HB-3

<400> SEQUENCE: 71

Tyr Thr Ser
1

<210> SEQ ID NO 72
<211> LENGTH: 3
<212> TYPE: PRT
<213> ORGANISM: Artificial Sequence
<220> FEATURE:
<223> OTHER INFORMATION: VL CDR-2 HB-5

<400> SEQUENCE: 72
```

-continued

Tyr Ala Ser
1

<210> SEQ ID NO 73
<211> LENGTH: 3
<212> TYPE: PRT
<213> ORGANISM: Artificial Sequence
<220> FEATURE:
<223> OTHER INFORMATION: VL CDR-2 HB-6

<400> SEQUENCE: 73

Ala Thr Ser
1

<210> SEQ ID NO 74
<211> LENGTH: 3
<212> TYPE: PRT
<213> ORGANISM: Artificial Sequence
<220> FEATURE:
<223> OTHER INFORMATION: VL CDR-2 HB-7

<400> SEQUENCE: 74

Ser Ala Ser
1

<210> SEQ ID NO 75
<211> LENGTH: 3
<212> TYPE: PRT
<213> ORGANISM: Artificial Sequence
<220> FEATURE:
<223> OTHER INFORMATION: VL CDR-2 HB-8

<400> SEQUENCE: 75

Lys Val Ser
1

<210> SEQ ID NO 76
<211> LENGTH: 3
<212> TYPE: PRT
<213> ORGANISM: Artificial Sequence
<220> FEATURE:
<223> OTHER INFORMATION: VL CDR-2 HB-9

<400> SEQUENCE: 76

Lys Val Ser
1

<210> SEQ ID NO 77
<211> LENGTH: 3
<212> TYPE: PRT
<213> ORGANISM: Artificial Sequence
<220> FEATURE:
<223> OTHER INFORMATION: VL CDR-2 HB-10

<400> SEQUENCE: 77

Tyr Thr Ser
1

<210> SEQ ID NO 78
<211> LENGTH: 3
<212> TYPE: PRT
<213> ORGANISM: Artificial Sequence
<220> FEATURE:
<223> OTHER INFORMATION: VL CDR-2 HB-11

<400> SEQUENCE: 78

Tyr Ile Ser

```
<210> SEQ ID NO 79
<211> LENGTH: 3
<212> TYPE: PRT
<213> ORGANISM: Artificial Sequence
<220> FEATURE:
<223> OTHER INFORMATION: VL CDR-2 HB-12

<400> SEQUENCE: 79

Lys Val Ser
1

<210> SEQ ID NO 80
<211> LENGTH: 3
<212> TYPE: PRT
<213> ORGANISM: Artificial Sequence
<220> FEATURE:
<223> OTHER INFORMATION: VL CDR-2 HB-14

<400> SEQUENCE: 80

Lys Val Ser
1

<210> SEQ ID NO 81
<211> LENGTH: 3
<212> TYPE: PRT
<213> ORGANISM: Artificial Sequence
<220> FEATURE:
<223> OTHER INFORMATION: VL CDR-2 HB-17

<400> SEQUENCE: 81

Tyr Thr Ser
1

<210> SEQ ID NO 82
<211> LENGTH: 3
<212> TYPE: PRT
<213> ORGANISM: Artificial Sequence
<220> FEATURE:
<223> OTHER INFORMATION: VL CDR-2 HB-20

<400> SEQUENCE: 82

Tyr Thr Ser
1

<210> SEQ ID NO 83
<211> LENGTH: 3
<212> TYPE: PRT
<213> ORGANISM: Artificial Sequence
<220> FEATURE:
<223> OTHER INFORMATION: VL CDR-2 HB-22

<400> SEQUENCE: 83

Lys Val Ser
1

<210> SEQ ID NO 84
<211> LENGTH: 9
<212> TYPE: PRT
<213> ORGANISM: Artificial Sequence
<220> FEATURE:
<223> OTHER INFORMATION: VL CDR-3 72A1

<400> SEQUENCE: 84

Val Leu Trp His Ser Asn His Trp Val
1               5
```

```
<210> SEQ ID NO 85
<211> LENGTH: 9
<212> TYPE: PRT
<213> ORGANISM: Artificial Sequence
<220> FEATURE:
<223> OTHER INFORMATION: VL CDR-3 HB-1

<400> SEQUENCE: 85

Gln Gln Tyr Asn Thr Tyr Pro Tyr Thr
1               5

<210> SEQ ID NO 86
<211> LENGTH: 9
<212> TYPE: PRT
<213> ORGANISM: Artificial Sequence
<220> FEATURE:
<223> OTHER INFORMATION: VL CDR-3 HB-2

<400> SEQUENCE: 86

Gln Gln Trp Ser Ser Asn Pro Pro Thr
1               5

<210> SEQ ID NO 87
<211> LENGTH: 9
<212> TYPE: PRT
<213> ORGANISM: Artificial Sequence
<220> FEATURE:
<223> OTHER INFORMATION: VL CDR-3 HB-3

<400> SEQUENCE: 87

Gln Gln Gly Asn Thr Leu Pro Pro Thr
1               5

<210> SEQ ID NO 88
<211> LENGTH: 10
<212> TYPE: PRT
<213> ORGANISM: Artificial Sequence
<220> FEATURE:
<223> OTHER INFORMATION: VL CDR-3 HB-5

<400> SEQUENCE: 88

Gln Gln Ser Asn Ser Trp Pro Met Leu Thr
1               5                   10

<210> SEQ ID NO 89
<211> LENGTH: 9
<212> TYPE: PRT
<213> ORGANISM: Artificial Sequence
<220> FEATURE:
<223> OTHER INFORMATION: VL CDR-3 HB-6

<400> SEQUENCE: 89

Gln Gln Trp Ser Ser Asn Pro Pro Thr
1               5

<210> SEQ ID NO 90
<211> LENGTH: 9
<212> TYPE: PRT
<213> ORGANISM: Artificial Sequence
<220> FEATURE:
<223> OTHER INFORMATION: VL CDR-3 HB-7

<400> SEQUENCE: 90

Gln Gln Tyr Ser Ser Tyr Pro Leu Thr
1               5
```

```
<210> SEQ ID NO 91
<211> LENGTH: 9
<212> TYPE: PRT
<213> ORGANISM: Artificial Sequence
<220> FEATURE:
<223> OTHER INFORMATION: VL CDR-3 HB-8

<400> SEQUENCE: 91

Phe Gln Gly Ser His Val Pro Tyr Thr
1               5

<210> SEQ ID NO 92
<211> LENGTH: 9
<212> TYPE: PRT
<213> ORGANISM: Artificial Sequence
<220> FEATURE:
<223> OTHER INFORMATION: VL CDR-3 HB-9

<400> SEQUENCE: 92

Phe Gln Gly Ser His Val Pro Tyr Thr
1               5

<210> SEQ ID NO 93
<211> LENGTH: 8
<212> TYPE: PRT
<213> ORGANISM: Artificial Sequence
<220> FEATURE:
<223> OTHER INFORMATION: VL CDR-3 HB-10

<400> SEQUENCE: 93

Gln Gln Asn Thr Leu Pro Pro Thr
1               5

<210> SEQ ID NO 94
<211> LENGTH: 10
<212> TYPE: PRT
<213> ORGANISM: Artificial Sequence
<220> FEATURE:
<223> OTHER INFORMATION: VL CDR-3 HB-11

<400> SEQUENCE: 94

Gln Gln Phe Thr Ser Ser Pro Ser Trp Thr
1               5                   10

<210> SEQ ID NO 95
<211> LENGTH: 9
<212> TYPE: PRT
<213> ORGANISM: Artificial Sequence
<220> FEATURE:
<223> OTHER INFORMATION: VL CDR-3 HB-12

<400> SEQUENCE: 95

Ser Gln Ser Thr His Val Pro Leu Thr
1               5

<210> SEQ ID NO 96
<211> LENGTH: 9
<212> TYPE: PRT
<213> ORGANISM: Artificial Sequence
<220> FEATURE:
<223> OTHER INFORMATION: VL CDR-3 HB-14

<400> SEQUENCE: 96

Phe Gln Gly Ser His Val Pro Pro Thr
1               5
```

```
<210> SEQ ID NO 97
<211> LENGTH: 9
<212> TYPE: PRT
<213> ORGANISM: Artificial Sequence
<220> FEATURE:
<223> OTHER INFORMATION: VL CDR-3 HB-17

<400> SEQUENCE: 97

Gln Gln Gly Asn Thr Leu Pro Pro Thr
1               5

<210> SEQ ID NO 98
<211> LENGTH: 9
<212> TYPE: PRT
<213> ORGANISM: Artificial Sequence
<220> FEATURE:
<223> OTHER INFORMATION: VL CDR-3 HB-20

<400> SEQUENCE: 98

Gln Gln Gly Asn Ala Leu Pro Pro Thr
1               5

<210> SEQ ID NO 99
<211> LENGTH: 9
<212> TYPE: PRT
<213> ORGANISM: Artificial Sequence
<220> FEATURE:
<223> OTHER INFORMATION: VL CDR-3 HB-22

<400> SEQUENCE: 99

Phe Gln Gly Ser His Val Pro Trp Thr
1               5

<210> SEQ ID NO 100
<211> LENGTH: 137
<212> TYPE: PRT
<213> ORGANISM: Artificial Sequence
<220> FEATURE:
<223> OTHER INFORMATION: heavy chain mAb 72A1

<400> SEQUENCE: 100

Pro Glu Leu Val Lys Pro Gly Thr Ser Met Lys Ile Ser Cys Lys Ala
1               5                   10                  15

Ser Gly Ser Ser Phe Thr Asp Tyr Thr Met Asn Trp Met Lys Gln Ser
            20                  25                  30

His Gly Lys Asn Leu Glu Trp Ile Gly Leu Ile Asn Pro Tyr Asn Gly
        35                  40                  45

Gly Thr Arg Tyr Asn Gln Lys Phe Lys Gly Lys Ala Thr Leu Thr Leu
    50                  55                  60

Asp Lys Ser Ser Ser Thr Ala Tyr Met Glu Val Leu Ser Leu Thr Ser
65                  70                  75                  80

Glu Asp Ser Ala Val Tyr Tyr Cys Ala Gly Gly Leu Arg Arg Val Asn
                85                  90                  95

Trp Phe Ala Tyr Trp Gly Gln Gly Thr Leu Val Ser Val Ser Ala Ala
            100                 105                 110

Lys Thr Thr Pro Pro Ser Val Tyr Pro Leu Ala Pro Gly Ser Ala Ala
        115                 120                 125

Gln Thr Asn Ser Met Val Thr Leu Gly
    130                 135

<210> SEQ ID NO 101
<211> LENGTH: 109
<212> TYPE: PRT
```

<213> ORGANISM: Artificial Sequence
<220> FEATURE:
<223> OTHER INFORMATION: light chain mAb 72A1

<400> SEQUENCE: 101

Gln Ala Val Leu Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Val Pro Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp His Ser Asn
                85                  90                  95

His Trp Val Phe Gly Gly Gly Thr Lys Leu Thr Val Leu
            100                 105

<210> SEQ ID NO 102
<211> LENGTH: 138
<212> TYPE: PRT
<213> ORGANISM: Artificial Sequence
<220> FEATURE:
<223> OTHER INFORMATION: heavy chain mAb HB1

<400> SEQUENCE: 102

Pro Gly Leu Val Ala Pro Ser Gln Ser Leu Ser Ile Thr Cys Thr Val
1               5                   10                  15

Ser Gly Phe Leu Leu Thr Thr Tyr Gly Val His Trp Val Arg Gln Pro
            20                  25                  30

Pro Gly Lys Gly Leu Glu Trp Leu Gly Val Ile Trp Ala Gly Gly Ser
        35                  40                  45

Thr Asn Tyr Asn Ser Ala Leu Met Ser Arg Leu Ser Ile Asn Lys Asp
    50                  55                  60

Ile Ser Lys Ser Gln Val Phe Leu Lys Met Asn Ser Leu Gln Thr Asp
65                  70                  75                  80

Asp Thr Ala Met Tyr Tyr Cys Thr Arg Asp Arg Gly Tyr Gly Tyr Leu
                85                  90                  95

Tyr Ala Met Asp Tyr Trp Gly Gln Gly Thr Ser Val Thr Val Ser Ser
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly
    130                 135

<210> SEQ ID NO 103
<211> LENGTH: 107
<212> TYPE: PRT
<213> ORGANISM: Artificial Sequence
<220> FEATURE:
<223> OTHER INFORMATION: light chain mAb HB1

<400> SEQUENCE: 103

Lys Phe Met Ser Thr Ser Val Gly Asp Arg Val Ser Val Thr Cys Lys
1               5                   10                  15

Ala Ser Gln Asn Val Gly Thr Asn Val Ala Trp Tyr Gln Gln Lys Pro
            20                  25                  30

Gly Gln Ser Pro Lys Ala Leu Ile Tyr Ser Thr Ser Ser Arg Tyr Thr
            35                  40                  45

Gly Val Pro Asp Arg Phe Ala Gly Ser Gly Ser Gly Thr Asp Tyr Thr
        50                  55                  60

Leu Thr Ile Ser Asn Val Gln Ser Glu Asp Leu Ala Glu Tyr Phe Cys
65                  70                  75                  80

Gln Gln Tyr Asn Thr Tyr Pro Tyr Thr Phe Gly Gly Gly Thr Arg Leu
                85                  90                  95

Asp Ile Lys Arg Ala Asp Ala Ala Pro Thr Val
            100                 105

<210> SEQ ID NO 104
<211> LENGTH: 134
<212> TYPE: PRT
<213> ORGANISM: Artificial Sequence
<220> FEATURE:
<223> OTHER INFORMATION: heavy chain mAb HB2

<400> SEQUENCE: 104

Pro Glu Leu Lys Lys Pro Gly Glu Thr Val Lys Ile Ser Cys Lys Ala
1               5                   10                  15

Ser Gly Tyr Thr Phe Thr Ala Tyr Ser Met His Trp Val Lys Leu Thr
            20                  25                  30

Pro Gly Lys Gly Leu Lys Trp Met Gly Trp Ile Asn Thr Lys Thr Gly
        35                  40                  45

Glu Pro Thr Tyr Ala Asp Asp Phe Lys Gly Arg Phe Ala Phe Ser Leu
    50                  55                  60

Glu Thr Ser Ala Ser Thr Ala Tyr Leu Gln Ile Asn Asn Leu Lys Asn
65                  70                  75                  80

Glu Asp Thr Ala Thr Tyr Phe Cys Ala Pro Tyr Gly Tyr Ala Leu Asp
                85                  90                  95

Tyr Trp Gly Gln Gly Thr Ser Val Thr Val Ser Ser Ala Lys Thr Thr
            100                 105                 110

Pro Pro Ser Val Tyr Pro Leu Ala Pro Gly Ser Ala Ala Gln Thr Asn
        115                 120                 125

Ser Met Val Thr Leu Gly
            130

<210> SEQ ID NO 105
<211> LENGTH: 106
<212> TYPE: PRT
<213> ORGANISM: Artificial Sequence
<220> FEATURE:
<223> OTHER INFORMATION: light chain mAb HB2

<400> SEQUENCE: 105

Ala Ile Leu Ser Ala Ser Pro Gly Glu Lys Val Thr Met Thr Cys Arg
1               5                   10                  15

Ala Thr Ser Ser Val Asn Tyr Met His Trp Tyr Gln Gln Lys Pro Gly
            20                  25                  30

Ser Ser Pro Lys Pro Trp Ile Tyr Ala Thr Ser Asn Leu Ala Ser Gly
        35                  40                  45

Val Pro Ala Arg Phe Ser Gly Ser Gly Ser Gly Thr Ser Tyr Ser Leu
    50                  55                  60

Thr Ile Ser Arg Val Glu Ala Glu Asp Ala Ala Thr Tyr Tyr Cys Gln
65                  70                  75                  80

Gln Trp Ser Ser Asn Pro Pro Thr Phe Gly Ala Gly Thr Lys Leu Glu 85                  90                  95

Leu Lys Arg Ala Asp Ala Ala Pro Thr Val
                100                 105

<210> SEQ ID NO 106
<211> LENGTH: 137
<212> TYPE: PRT
<213> ORGANISM: Artificial Sequence
<220> FEATURE:
<223> OTHER INFORMATION: heavy chain mAb HB3

<400> SEQUENCE: 106

Ala Glu Leu Val Arg Pro Gly Ala Ser Val Lys Leu Ser Cys Lys Ala
1               5                   10                  15

Ser Gly Tyr Thr Phe Ala Ser Tyr Trp Met Gln Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Arg Phe Lys Asn Lys Ala Ser Leu Thr Val
    50                  55                  60

Asp Lys Ser Ser Ser Thr Ala Tyr Met Gln Leu Ser Ser Leu Thr Ser
65                  70                  75                  80

Glu Asp Ser Ala Val Tyr Tyr Cys Ala Arg Asn Leu Tyr Tyr Tyr Gly
                85                  90                  95

Arg Pro Asp Tyr Trp Gly Gln Gly Thr Ser Val Thr Val Ser Ser Ala
            100                 105                 110

Lys Thr Thr Ala Pro Ser Val Tyr Pro Leu Ala Pro Val Cys Gly Asp
        115                 120                 125

Thr Thr Gly Ser Ser Val Thr Leu Gly
    130                 135

<210> SEQ ID NO 107
<211> LENGTH: 107
<212> TYPE: PRT
<213> ORGANISM: Artificial Sequence
<220> FEATURE:
<223> OTHER INFORMATION: light chain mAb HB3

<400> SEQUENCE: 107

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Ile Lys Leu Leu Ile Tyr Tyr Thr Ser Arg Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Glu Glu Asp Ile Ala Thr Tyr Phe Cys
65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 108
<211> LENGTH: 140
<212> TYPE: PRT
<213> ORGANISM: Artificial Sequence
<220> FEATURE:

<223> OTHER INFORMATION: heavy chain mAb HB5

<400> SEQUENCE: 108

Ala Glu Leu Val Arg Pro Gly Ala Ser Val Lys Ile Ser Cys Lys Ala
1               5                   10                  15

Phe Gly Tyr Thr Phe Thr Asn His Asn Ile Asn Trp Val Lys Gln Arg
            20                  25                  30

Pro Gly Gln Gly Leu Asp Trp Ile Gly Tyr Ile Asn Pro Tyr Asn Asp
        35                  40                  45

Tyr Thr Ser Tyr Asn Gln Lys Phe Lys Gly Lys Ala Thr Leu Thr Val
    50                  55                  60

Asp Lys Ser Ser Asn Thr Ala Tyr Met Glu Leu Ser Ser Leu Thr Ser
65                  70                  75                  80

Glu Asp Ser Ala Val Tyr Tyr Cys Ala Arg Ser Glu Gly Trp Leu Arg
                85                  90                  95

Arg Gly Ala Trp Phe Ala Tyr Trp Gly Gln Gly Thr Leu Val Thr Val
            100                 105                 110

Ser Ala Ala Lys Thr Thr Ala Pro Ser Val Tyr Pro Leu Ala Pro Val
        115                 120                 125

Cys Gly Asp Thr Thr Gly Ser Ser Val Thr Leu Gly
        130                 135                 140

<210> SEQ ID NO 109
<211> LENGTH: 108
<212> TYPE: PRT
<213> ORGANISM: Artificial Sequence
<220> FEATURE:
<223> OTHER INFORMATION: light chain mAb HB5

<400> SEQUENCE: 109

Ala Ile Leu Ser Val Ser Pro Gly Glu Arg Val Ser Phe Ser Cys Arg
1               5                   10                  15

Ala Ser Gln Ser Ile Gly Thr Ser Ile His Trp Tyr Gln Gln Arg Thr
            20                  25                  30

Asn Asp Ser Pro Arg Leu Leu Ile Lys Tyr Ala Ser Glu Ser Ile Ser
        35                  40                  45

Gly Ile Pro Pro Arg Phe Ser Gly Ser Gly Ser Gly Thr Asp Phe Thr
    50                  55                  60

Leu Ser Ile Asn Ser Val Glu Ser Glu Asp Ile Ala Asp Tyr His Cys
65                  70                  75                  80

Gln Gln Ser Asn Ser Trp Pro Met Leu Thr Phe Gly Ala Gly Thr Lys
                85                  90                  95

Leu Glu Leu Lys Arg Ala Asp Ala Ala Pro Thr Val
            100                 105

<210> SEQ ID NO 110
<211> LENGTH: 134
<212> TYPE: PRT
<213> ORGANISM: Artificial Sequence
<220> FEATURE:
<223> OTHER INFORMATION: heavy chain mAb HB6

<400> SEQUENCE: 110

Pro Glu Leu Arg Lys Pro Gly Glu Thr Val Lys Ile Ser Cys Lys Ala
1               5                   10                  15

Ser Gly Tyr Thr Phe Thr Asp Tyr Ser Met His Trp Val Lys Gln Thr
            20                  25                  30

Pro Gly Lys Gly Leu Lys Trp Met Gly Trp Ile Asn Thr Arg Thr Gly

```
                    35                  40                  45

Glu Pro Arg Tyr Ala Asp Asp Phe Lys Gly Arg Phe Ala Phe Ser Leu
 50                  55                  60

Glu Thr Ser Ala Ser Thr Ala Tyr Leu Gln Ile Asn Asn Leu Lys Asn
 65                  70                  75                  80

Glu Asp Thr Ala Thr Tyr Phe Cys Ala Pro Tyr Gly Tyr Ala Leu Asp
                     85                  90                  95

Tyr Trp Gly Gln Gly Thr Ser Val Thr Val Ser Ser Ala Lys Thr Thr
                    100                 105                 110

Pro Pro Ser Val Tyr Pro Leu Ala Pro Gly Ser Ala Ala Gln Thr Asn
                    115                 120                 125

Ser Met Val Thr Leu Gly
                    130

<210> SEQ ID NO 111
<211> LENGTH: 106
<212> TYPE: PRT
<213> ORGANISM: Artificial Sequence
<220> FEATURE:
<223> OTHER INFORMATION: light chain mAb HB6

<400> SEQUENCE: 111

Ala Ile Leu Ser Ala Ser Pro Gly Glu Lys Val Thr Met Thr Cys Arg
 1               5                  10                  15

Ala Thr Ser Ser Val Asn Tyr Met His Trp Tyr Gln Gln Lys Pro Gly
                 20                  25                  30

Ser Ser Pro Lys Pro Trp Ile Tyr Ala Thr Ser Asn Leu Ala Ser Gly
                 35                  40                  45

Val Pro Ala Arg Phe Ser Gly Ser Gly Ser Gly Thr Ser Tyr Ser Leu
 50                  55                  60

Thr Ile Ser Arg Val Glu Ala Glu Asp Ala Ala Thr Tyr Tyr Cys Gln
 65                  70                  75                  80

Gln Trp Ser Ser Asn Pro Pro Thr Phe Gly Ala Gly Thr Lys Leu Glu
                 85                  90                  95

Leu Lys Arg Ala Asp Ala Ala Pro Thr Val
                100                 105

<210> SEQ ID NO 112
<211> LENGTH: 136
<212> TYPE: PRT
<213> ORGANISM: Artificial Sequence
<220> FEATURE:
<223> OTHER INFORMATION: heavy chain mAb HB7

<400> SEQUENCE: 112

Ala Glu Leu Val Arg Pro Gly Ala Ser Val Lys Leu Ser Cys Lys Ala
 1               5                  10                  15

Leu Gly Tyr Thr Phe Thr Asp Tyr Glu Met His Trp Val Lys Gln Thr
                 20                  25                  30

Pro Val His Gly Leu Glu Trp Ile Gly Thr Ile Ser Pro Gly Arg Ser
                 35                  40                  45

Gly Thr Ala Tyr Asn Gln Lys Phe Lys Gly Lys Ala Thr Leu Thr Ala
 50                  55                  60

Asp Lys Ser Ser Arg Thr Ala Tyr Met Glu Leu Asn Ser Leu Thr Ser
 65                  70                  75                  80

Glu Asp Ser Ala Val Tyr Tyr Cys Ser Arg Tyr Gly His Pro Ser Tyr
                 85                  90                  95
```

Leu Asp Val Trp Gly Ala Gly Thr Thr Val Thr Val Ser Ser Ala Lys
                100                 105                 110

Thr Thr Pro Pro Ser Val Tyr Pro Leu Ala Pro Gly Ser Ala Ala Gln
            115                 120                 125

Thr Asn Ser Met Val Thr Leu Gly
        130                 135

<210> SEQ ID NO 113
<211> LENGTH: 107
<212> TYPE: PRT
<213> ORGANISM: Artificial Sequence
<220> FEATURE:
<223> OTHER INFORMATION: light chain mAb HB7

<400> SEQUENCE: 113

Lys Phe Met Ser Thr Ser Val Gly Asp Arg Val Asn Ile Thr Cys Lys
1               5                   10                  15

Ala Ser Gln Ser Val Gly Asn Ala Val Ala Trp Phe Gln Gln Lys Pro
            20                  25                  30

Gly Gln Ser Pro Lys Leu Leu Ile Tyr Ser Ala Ser Asn Arg Tyr Thr
        35                  40                  45

Gly Ile Pro Asp Arg Phe Thr Gly Ser Gly Ser Gly Thr Asp Phe Thr
    50                  55                  60

Leu Thr Cys Asn Asn Met Gln Ser Glu Asp Leu Ala Asp Tyr Phe Cys
65                  70                  75                  80

Gln Gln Tyr Ser Ser Tyr Pro Leu Thr Phe Gly Ala Gly Thr Lys Leu
                85                  90                  95

Glu Leu Lys Arg Ala Asp Ala Ala Pro Thr Val
            100                 105

<210> SEQ ID NO 114
<211> LENGTH: 140
<212> TYPE: PRT
<213> ORGANISM: Artificial Sequence
<220> FEATURE:
<223> OTHER INFORMATION: heavy chain mAb HB8

<400> SEQUENCE: 114

Pro Glu Leu Lys Lys Pro Gly Glu Thr Val Lys Ile Ser Cys Lys Ala
1               5                   10                  15

Ser Gly Tyr Ser Phe Thr Asn Tyr Gly Met Asn Trp Val Lys Gln Ala
            20                  25                  30

Pro Gly Lys Gly Leu Lys Trp Met Gly Trp Ile Asn Thr Tyr Thr Gly
        35                  40                  45

Glu Pro Thr Tyr Ala Asp Asp Phe Lys Gly Arg Phe Ala Phe Ser Leu
    50                  55                  60

Glu Thr Ser Ala Ser Thr Ala Phe Leu Gln Ile Asn Asn Leu Lys Asn
65                  70                  75                  80

Glu Asp Thr Ala Thr Tyr Leu Cys Ala Arg Tyr Tyr Tyr Gly Ser Val
                85                  90                  95

Tyr Ser Ala Trp Phe Ala Tyr Trp Gly Gln Gly Thr Leu Val Thr Val
            100                 105                 110

Ser Ala Ala Lys Thr Thr Pro Pro Ser Val Tyr Pro Leu Ala Pro Gly
        115                 120                 125

Ser Ala Ala Gln Thr Asn Ser Met Val Thr Leu Gly
        130                 135                 140

<210> SEQ ID NO 115

<211> LENGTH: 112
<212> TYPE: PRT
<213> ORGANISM: Artificial Sequence
<220> FEATURE:
<223> OTHER INFORMATION: light chain mAb HB8

<400> SEQUENCE: 115

Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
        35                  40                  45

Ser Asn Arg Phe Ser Gly Val Pro Asp Arg Phe Gly Gly Ser Gly Ser
    50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Tyr Thr Phe Gly
                85                  90                  95

Gly Gly Thr Lys Leu Glu Ile Lys Arg Ala Asp Ala Ala Pro Thr Val
            100                 105                 110

<210> SEQ ID NO 116
<211> LENGTH: 141
<212> TYPE: PRT
<213> ORGANISM: Artificial Sequence
<220> FEATURE:
<223> OTHER INFORMATION: heavy chain mAb HB9

<400> SEQUENCE: 116

Gly Gly Leu Val Lys Pro Gly Gly Ser Leu Lys Leu Ser Cys Ala Ala
1               5                   10                  15

Ser Gly Phe Thr Phe Ser Ser Tyr Thr Met Ser Trp Val Arg Gln Thr
            20                  25                  30

Pro Glu Lys Arg Leu Glu Trp Val Ala Thr Ile Ser Ser Gly Gly Ser
        35                  40                  45

Tyr Ile Tyr Tyr Pro Asp Ser Val Lys Gly Arg Phe Thr Ile Ser Arg
    50                  55                  60

Asp Asn Ala Lys Asn Thr Leu Tyr Leu Gln Met Ser Ser Leu Lys Ser
65                  70                  75                  80

Glu Asp Thr Ala Ile Tyr Tyr Cys Thr Arg Glu Asp Phe Tyr Tyr Gly
                85                  90                  95

Ser Ser Tyr Gly Phe Phe Asp Val Trp Gly Ala Gly Thr Thr Val Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly
    130                 135                 140

<210> SEQ ID NO 117
<211> LENGTH: 112
<212> TYPE: PRT
<213> ORGANISM: Artificial Sequence
<220> FEATURE:
<223> OTHER INFORMATION: light chain mAb HB9

<400> SEQUENCE: 117

Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
            35                  40                  45

Ser Asn Arg Phe Ser Gly Val Pro Asp Arg Phe Gly Gly Ser Gly Ser
        50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Tyr Thr Phe Gly
                85                  90                  95

Gly Gly Thr Lys Leu Glu Ile Lys Arg Ala Asp Ala Ala Pro Thr Val
            100                 105                 110

<210> SEQ ID NO 118
<211> LENGTH: 112
<212> TYPE: PRT
<213> ORGANISM: Artificial Sequence
<220> FEATURE:
<223> OTHER INFORMATION: heavy chain mAb HB10

<400> SEQUENCE: 118

Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Ala Gly Gln Ser Pro Lys Leu Leu Ile Tyr Lys Val
            35                  40                  45

Ser Asn Arg Phe Ser Gly Val Pro Asp Arg Phe Gly Gly Ser Gly Ser
        50                  55                  60

Gly Thr Asp Phe Thr Leu Lys Ile Ser Arg Val Glu Ala Glu Asp Leu
65                  70                  75                  80

Gly Val Tyr Tyr Cys Phe Gln Gly Ser His Val Pro Tyr Thr Phe Gly
                85                  90                  95

Gly Gly Thr Lys Leu Glu Ile Lys Arg Ala Asp Ala Ala Pro Thr Val
            100                 105                 110

<210> SEQ ID NO 119
<211> LENGTH: 107
<212> TYPE: PRT
<213> ORGANISM: Artificial Sequence
<220> FEATURE:
<223> OTHER INFORMATION: light chain mAb HB10

<400> SEQUENCE: 119

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Val Lys Leu Leu Ile Tyr Tyr Thr Ser Arg Leu His Ser
            35                  40                  45

Gly Val Pro Ser Arg Phe Ser Gly Ser Gly Ser Gly Thr Asp Tyr Ser
        50                  55                  60

Leu Thr Ile Ser Asn Leu Glu Glu Glu Asp Ile Ala Thr Tyr Phe Cys
65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 120
<211> LENGTH: 138
<212> TYPE: PRT
<213> ORGANISM: Artificial Sequence
<220> FEATURE:
<223> OTHER INFORMATION: heavy chain mAb HB11

<400> SEQUENCE: 120

```
Pro Ser Leu Val Lys Pro Ser Gln Thr Leu Ser Leu Thr Cys Ser Val
1               5                   10                  15

Thr Gly Asp Ser Ile Thr Ser Gly Phe Trp Asn Trp Ile Arg Lys Phe
            20                  25                  30

Pro Gly Asn Lys Leu Glu Tyr Met Gly Tyr Ile Ser Tyr Ser Gly Ser
        35                  40                  45

Thr Tyr Tyr Asn Pro Ser Leu Lys Ser Arg Ile Ser Ile Thr Arg Asp
    50                  55                  60

Thr Ser Lys Asn Gln Tyr Tyr Leu Gln Leu Asn Ser Val Thr Thr Glu
65                  70                  75                  80

Asp Thr Ala Thr Tyr Tyr Cys Ala Arg Gly Asn Gly Gly Asn Tyr Asp
                85                  90                  95

Trp Tyr Phe Asp Val Trp Gly Ala Gly Thr Thr Val Thr Val Ser Ser
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly
    130                 135
```

<210> SEQ ID NO 121
<211> LENGTH: 107
<212> TYPE: PRT
<213> ORGANISM: Artificial Sequence
<220> FEATURE:
<223> OTHER INFORMATION: light chain mAb HB11

<400> SEQUENCE: 121

```
Ala Ile Met Ser Ala Ser Leu Gly Glu Lys Val Thr Met Ser Cys Arg
1               5                   10                  15

Ala Ser Ser Ser Val Asn Phe Met Asn Trp Tyr Gln Gln Lys Ser Asp
            20                  25                  30

Asp Ser Pro Lys Leu Leu Ile Tyr Tyr Ile Ser Asn Leu Ala Pro Gly
        35                  40                  45

Val Pro Ala Arg Phe Ser Gly Ser Gly Ser Asn Ser Tyr Ser Leu
    50                  55                  60

Thr Ile Ser Gly Met Glu Gly Glu Asp Ala Ala Thr Tyr Tyr Cys Gln
65                  70                  75                  80

Gln Phe Thr Ser Ser Pro Ser Trp Thr Phe Gly Gly Thr Lys Leu
                85                  90                  95

Glu Ile Lys Arg Ala Asp Ala Ala Pro Thr Val
            100                 105
```

<210> SEQ ID NO 122
<211> LENGTH: 111
<212> TYPE: PRT
<213> ORGANISM: Artificial Sequence
<220> FEATURE:
<223> OTHER INFORMATION: heavy chain mAb HB12

<400> SEQUENCE: 122

Ala Glu Leu Val Arg Pro Gly Ala Ser Val Lys Leu Ser Cys Lys Ala
1               5                   10                  15

Ser Gly Tyr Thr Phe Thr Asn Tyr Trp Ile His Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Arg Phe Lys Asn Lys Ala Ser Leu Thr Val
    50                  55                  60

Asp Lys Ser Ser Ser Thr Ala Tyr Met Gln Leu Ser Ser Leu Thr Ser
65              70                  75                  80

Glu Asp Ser Ala Val Tyr Tyr Cys Ala Arg Asn Leu Tyr Tyr Tyr Gly
                85                  90                  95

Arg Pro Asp Tyr Trp Gly Gln Gly Thr Ser Val Thr Val Ser Ser
        100                 105                 110

<210> SEQ ID NO 123
<211> LENGTH: 104
<212> TYPE: PRT
<213> ORGANISM: Artificial Sequence
<220> FEATURE:
<223> OTHER INFORMATION: light chain mAb HB12

<400> SEQUENCE: 123

Leu Ser Leu Pro Val Ser Leu Gly Asp Gln Ala Ser Ile Ser Cys Arg
1               5                   10                  15

Ser Ser Gln Ser Leu Val His Ser Asn Gly Asn Thr Tyr Leu His Trp
            20                  25                  30

Tyr Leu Gln Lys Pro Gly Gln Ser Pro Lys Leu Leu Ile Tyr Lys Val
            35                  40                  45

Ser Asn Arg Phe Ser Gly Val Pro Asp Arg Phe Ser Gly Ser Gly Ser
        50                  55                  60

Gly Thr Asp Phe Thr Leu Lys Ile Ser Arg Val Glu Ala Glu Asp Leu
65              70                  75                  80

Gly Val Tyr Phe Cys Ser Gln Ser Thr His Val Pro Leu Thr Phe Gly
                85                  90                  95

Ser Gly Thr Lys Leu Glu Ile Lys
            100

<210> SEQ ID NO 124
<211> LENGTH: 112
<212> TYPE: PRT
<213> ORGANISM: Artificial Sequence
<220> FEATURE:
<223> OTHER INFORMATION: heavy chain mAb HB14

<400> SEQUENCE: 124

Ser Gly Ala Glu Leu Val Arg Pro Gly Ala Ser Val Asn Leu Ser Cys
1               5                   10                  15

Lys Ala Leu Gly Tyr Thr Phe Thr Asp Tyr Glu Met His Trp Val Lys
            20                  25                  30

Gln Thr Pro Val Tyr Gly Leu Glu Trp Ile Gly Thr Ile His Pro Arg
            35                  40                  45

Arg Gly Gly Thr Ala Tyr Asn Gln Arg Phe Lys Gly Lys Ala Ala Leu
        50                  55                  60

Thr Ala Asp Lys Ser Ser Ser Thr Ala Tyr Met Glu Leu Ser Ser Leu
65              70                  75                  80

Thr Ser Glu Asp Ser Ala Val Tyr Tyr Cys Ala Arg Tyr Gly Tyr Pro
                85                  90                  95

Trp Tyr Phe Asp Val Trp Gly Ala Gly Thr Thr Val Thr Val Ser Ser
            100                 105                 110

<210> SEQ ID NO 125
<211> LENGTH: 104
<212> TYPE: PRT
<213> ORGANISM: Artificial Sequence
<220> FEATURE:
<223> OTHER INFORMATION: light chain mAb HB14

<400> SEQUENCE: 125

Leu Ser Leu Pro Val Ser Leu Gly Asp Gln Ala Ser Ile Ser Cys Arg
1               5                   10                  15

Ser Ser Gln Ser Ile Val His Asp Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Leu Asp Lys Phe Ser Gly Ser Gly Ser
    50                  55                  60

Gly Thr Asp Phe Thr Leu Lys Ile Ser Arg Val Glu Ala Glu Asp Leu
65                  70                  75                  80

Gly Ile Tyr Tyr Cys Phe Gln Gly Ser His Val Pro Pro Thr Phe Gly
                85                  90                  95

Gly Gly Thr Lys Leu Glu Ile Lys
            100

<210> SEQ ID NO 126
<211> LENGTH: 137
<212> TYPE: PRT
<213> ORGANISM: Artificial Sequence
<220> FEATURE:
<223> OTHER INFORMATION: heavy chain mAb HB17

<400> SEQUENCE: 126

Ala Glu Leu Val Ile Pro Gly Ala Ser Val Lys Val Ser Cys Lys Ala
1               5                   10                  15

Ser Gly Tyr Thr Phe Thr Ser Tyr Trp Ile His Trp Val Lys Gln Trp
            20                  25                  30

Pro Gly Gln Gly Leu Glu Trp Ile Gly Glu Ile Asn Pro Asn Asn Gly
        35                  40                  45

His Thr Asn Tyr Asn Glu Lys Phe Lys Ser Lys Ala Thr Leu Thr Val
    50                  55                  60

Asp Lys Ser Ser Ser Thr Ala Tyr Met Gln Leu Ser Ser Leu Thr Ser
65                  70                  75                  80

Glu Asp Ser Ala Val Tyr Tyr Cys Ala Arg Asn Leu Phe Tyr Tyr Ser
                85                  90                  95

Arg Pro Asp Tyr Trp Gly Gln Gly Thr Ser Val Thr Val Ser Ser Ala
            100                 105                 110

Lys Thr Thr Pro Pro Ser Val Tyr Pro Leu Ala Pro Gly Cys Gly Asp
        115                 120                 125

Thr Thr Gly Ser Ser Val Thr Leu Gly
    130                 135

<210> SEQ ID NO 127
<211> LENGTH: 107
<212> TYPE: PRT
<213> ORGANISM: Artificial Sequence
<220> FEATURE:
<223> OTHER INFORMATION: light chain mAb HB17

<400> SEQUENCE: 127

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Ile Lys Leu Leu Ile Tyr Tyr Thr Ser Arg Leu His Ser
        35                  40                  45

Gly Val Pro Ser Arg Phe Ser Gly Ser Gly Ser Gly Thr Asp Tyr Ser
    50                  55                  60

Leu Thr Ile Ser Asn Leu Glu Glu Asp Ile Ala Thr Tyr Phe Cys
65                  70                  75                  80

Gln Gln Gly Asn Thr Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 128
<211> LENGTH: 136
<212> TYPE: PRT
<213> ORGANISM: Artificial Sequence
<220> FEATURE:
<223> OTHER INFORMATION: heavy chain mAb HB20

<400> SEQUENCE: 128

Glu Leu Val Lys Pro Gly Ala Ser Val Lys Leu Ser Cys Lys Ala Ser
1               5                   10                  15

Gly Tyr Thr Phe Thr Ser Tyr Trp Ile Gln Trp Val Lys Gln Arg Pro
            20                  25                  30

Gly Gln Gly Leu Glu Trp Ile Gly Glu Ile Asn Pro Thr Asn Gly His
        35                  40                  45

Thr Asn Tyr Asn Glu Lys Phe Lys Thr Lys Ala Thr Leu Thr Val Asp
    50                  55                  60

Lys Ser Ser Ser Thr Ala Tyr Met Arg Leu Ser Ser Leu Thr Ser Glu
65                  70                  75                  80

Asp Ser Ala Val Tyr Tyr Cys Ala Arg Asn Leu Tyr Tyr Tyr Gly Arg
                85                  90                  95

Pro Asp Tyr Trp Gly Gln Gly Thr Ser Val Thr Val Ser Ser Ala Lys
            100                 105                 110

Thr Thr Ala Pro Ser Val Tyr Pro Leu Ala Pro Val Cys Gly Asp Thr
        115                 120                 125

Thr Gly Ser Ser Val Thr Leu Gly
        130                 135

<210> SEQ ID NO 129
<211> LENGTH: 107
<212> TYPE: PRT
<213> ORGANISM: Artificial Sequence
<220> FEATURE:
<223> OTHER INFORMATION: light chain mAb HB20

<400> SEQUENCE: 129

Ser Ser Leu Ser Ala Ser Leu Gly Asp Arg Val Thr Ile Ser Cys Arg
1               5                   10                  15

Ala Ser Gln Asp Ile Gly Asn Tyr Leu Asn Trp Tyr Gln Gln Lys Pro
            20                  25                  30

Asp Gly Thr Val Lys Leu Leu Ile Tyr Tyr Thr Ser Arg Leu His Ser
        35                  40                  45

```
Gly Val Pro Ser Arg Phe Ser Gly Ser Gly Thr Asp Tyr Ser
    50                  55                  60

Leu Thr Ile Ser Asn Leu Glu Gln Glu Asp Ile Ala Thr Tyr Phe Cys
65                  70                  75                  80

Gln Gln Gly Asn Ala Leu Pro Pro Thr Phe Gly Gly Gly Thr Lys Leu
                85                  90                  95

Glu Ile Lys Arg Ala Asp Ala Ala Pro Thr Val
            100                 105

<210> SEQ ID NO 130
<211> LENGTH: 139
<212> TYPE: PRT
<213> ORGANISM: Artificial Sequence
<220> FEATURE:
<223> OTHER INFORMATION: heavy chain mAb HB22

<400> SEQUENCE: 130

Pro Gly Leu Val Ala Pro Ser Gln Ser Leu Ser Ile Thr Cys Thr Val
1               5                   10                  15

Ser Gly Phe Ser Leu Thr Asn Tyr Gly Ile His Trp Val Arg Gln Pro
            20                  25                  30

Pro Gly Lys Gly Leu Glu Trp Leu Val Val Ile Trp Ser Asp Gly Ser
        35                  40                  45

Thr Ile Tyr Asn Ser Ala Leu Lys Ser Arg Leu Ser Ile Ser Lys Asp
    50                  55                  60

Asn Ser Lys Ser Gln Val Phe Leu Lys Met Asn Ser Leu Gln Thr Asp
65                  70                  75                  80

Asp Thr Ala Met Tyr Tyr Cys Ala Arg Asn Tyr Tyr Gly Asn Ser Tyr
                85                  90                  95

Pro Ala Trp Phe Ala Tyr Trp Gly Gln Gly Thr Leu Val Thr Val Ser
            100                 105                 110

Ala Ala Lys Thr Thr Pro Pro Ser Val Tyr Pro Leu Ala Pro Gly Ser
        115                 120                 125

Ala Ala Gln Thr Asn Ser Met Val Thr Leu Gly
    130                 135

<210> SEQ ID NO 131
<211> LENGTH: 112
<212> TYPE: PRT
<213> ORGANISM: Artificial Sequence
<220> FEATURE:
<223> OTHER INFORMATION: light chain mAb HB22

<400> SEQUENCE: 131

Leu Ser Leu Pro Val Ser Leu Gly Asp Gln Ala Ser Ile Ser Cys Arg
1               5                   10                  15

Ser Ser Gln Ser Ile Val His Ser Asn Gly Asn Thr Tyr Leu Glu Trp
            20                  25                  30

Tyr Leu Gln Lys Pro Gly Gln Ser Pro Lys Leu Leu Ile Tyr Lys Val
        35                  40                  45

Ser Asn Arg Phe Ser Gly Val Pro Asp Arg Phe Ser Gly Ser Gly Ser
    50                  55                  60

Gly Thr Asp Phe Thr Leu Arg Ile Ser Arg Val Glu Ala Glu Asp Leu
65                  70                  75                  80

Gly Val Tyr Tyr Cys Phe Gln Gly Ser His Val Pro Trp Thr Phe Gly
                85                  90                  95

Gly Gly Thr Lys Leu Glu Ile Lys Arg Ala Asp Ala Ala Pro Thr Val
```

-continued

<210> SEQ ID NO 132
<211> LENGTH: 20
<212> TYPE: PRT
<213> ORGANISM: Artificial Sequence
<220> FEATURE:
<223> OTHER INFORMATION: EBV gp350

<400> SEQUENCE: 132

Met Glu Ala Ala Leu Leu Val Cys Gln Tyr Thr Ile Gln Ser Leu Ile
1               5                   10                  15

His Leu Thr Gly
            20

<210> SEQ ID NO 133
<211> LENGTH: 20
<212> TYPE: PRT
<213> ORGANISM: Artificial Sequence
<220> FEATURE:
<223> OTHER INFORMATION: EBV gp350

<400> SEQUENCE: 133

Glu Asp Pro Gly Phe Phe Asn Val Glu Ile Pro Glu Phe Pro Phe Tyr
1               5                   10                  15

Pro Thr Cys Asn
            20

<210> SEQ ID NO 134
<211> LENGTH: 21
<212> TYPE: PRT
<213> ORGANISM: Artificial Sequence
<220> FEATURE:
<223> OTHER INFORMATION: EBV gp350

<400> SEQUENCE: 134

Val Cys Thr Ala Asp Val Asn Val Thr Ile Asn Phe Asp Val Gly Gly
1               5                   10                  15

Lys Lys His Gln Leu
            20

<210> SEQ ID NO 135
<211> LENGTH: 20
<212> TYPE: PRT
<213> ORGANISM: Artificial Sequence
<220> FEATURE:
<223> OTHER INFORMATION: EBV gp350

<400> SEQUENCE: 135

Asp Leu Asp Phe Gly Gln Leu Thr Pro His Thr Lys Ala Val Tyr Gln
1               5                   10                  15

Pro Arg Gly Ala
            20

<210> SEQ ID NO 136
<211> LENGTH: 20
<212> TYPE: PRT
<213> ORGANISM: Artificial Sequence
<220> FEATURE:
<223> OTHER INFORMATION: EBV gp350

<400> SEQUENCE: 136

Phe Gly Gly Ser Glu Asn Ala Thr Asn Leu Phe Leu Leu Glu Leu Leu
1               5                   10                  15

-continued

Gly Ala Gly Glu
          20

<210> SEQ ID NO 137
<211> LENGTH: 20
<212> TYPE: PRT
<213> ORGANISM: Artificial Sequence
<220> FEATURE:
<223> OTHER INFORMATION: EBV gp350

<400> SEQUENCE: 137

Leu Ala Leu Thr Met Arg Ser Lys Lys Leu Pro Ile Asn Val Thr Thr
1               5                   10                  15

Gly Glu Glu Gln
          20

<210> SEQ ID NO 138
<211> LENGTH: 20
<212> TYPE: PRT
<213> ORGANISM: Artificial Sequence
<220> FEATURE:
<223> OTHER INFORMATION: EBV gp350

<400> SEQUENCE: 138

Gln Val Ser Leu Glu Ser Val Asp Val Tyr Phe Gln Asp Val Phe Gly
1               5                   10                  15

Thr Met Trp Cys
          20

<210> SEQ ID NO 139
<211> LENGTH: 20
<212> TYPE: PRT
<213> ORGANISM: Artificial Sequence
<220> FEATURE:
<223> OTHER INFORMATION: EBV gp350

<400> SEQUENCE: 139

His His Ala Glu Met Gln Asn Pro Val Tyr Leu Ile Pro Glu Thr Val
1               5                   10                  15

Pro Tyr Ile Lys
          20

<210> SEQ ID NO 140
<211> LENGTH: 20
<212> TYPE: PRT
<213> ORGANISM: Artificial Sequence
<220> FEATURE:
<223> OTHER INFORMATION: EBV gp350

<400> SEQUENCE: 140

Trp Asp Asn Cys Asn Ser Thr Asn Ile Thr Ala Val Val Arg Ala Gln
1               5                   10                  15

Gly Leu Asp Val
          20

<210> SEQ ID NO 141
<211> LENGTH: 20
<212> TYPE: PRT
<213> ORGANISM: Artificial Sequence
<220> FEATURE:
<223> OTHER INFORMATION: EBV gp350

<400> SEQUENCE: 141

Thr Leu Pro Leu Ser Leu Pro Thr Ser Ala Gln Asp Ser Asn Phe Ser
1               5                   10                  15

Val Lys Thr Glu
            20

<210> SEQ ID NO 142
<211> LENGTH: 20
<212> TYPE: PRT
<213> ORGANISM: Artificial Sequence
<220> FEATURE:
<223> OTHER INFORMATION: EBV gp350

<400> SEQUENCE: 142

Met Leu Gly Asn Glu Ile Asp Ile Glu Cys Ile Met Glu Asp Gly Glu
1               5                   10                  15

Ile Ser Gln Val
            20

<210> SEQ ID NO 143
<211> LENGTH: 20
<212> TYPE: PRT
<213> ORGANISM: Artificial Sequence
<220> FEATURE:
<223> OTHER INFORMATION: EBV gp350

<400> SEQUENCE: 143

Leu Pro Gly Asp Asn Lys Phe Asn Ile Thr Cys Ser Gly Tyr Glu Ser
1               5                   10                  15

His Val Pro Ser
            20

<210> SEQ ID NO 144
<211> LENGTH: 20
<212> TYPE: PRT
<213> ORGANISM: Artificial Sequence
<220> FEATURE:
<223> OTHER INFORMATION: EBV gp350

<400> SEQUENCE: 144

Gly Gly Ile Leu Thr Ser Thr Ser Pro Val Ala Thr Pro Ile Pro Gly
1               5                   10                  15

Thr Gly Tyr Ala
            20

<210> SEQ ID NO 145
<211> LENGTH: 20
<212> TYPE: PRT
<213> ORGANISM: Artificial Sequence
<220> FEATURE:
<223> OTHER INFORMATION: EBV gp350

<400> SEQUENCE: 145

Tyr Ser Leu Arg Leu Thr Pro Arg Pro Val Ser Arg Phe Leu Gly Asn
1               5                   10                  15

Asn Ser Ile Leu
            20

<210> SEQ ID NO 146
<211> LENGTH: 20
<212> TYPE: PRT
<213> ORGANISM: Artificial Sequence
<220> FEATURE:
<223> OTHER INFORMATION: EBV gp350

<400> SEQUENCE: 146

Tyr Val Phe Tyr Ser Gly Asn Gly Pro Lys Ala Ser Gly Gly Asp Tyr

```
                1               5                  10                  15

Cys Ile Gln Ser
            20

<210> SEQ ID NO 147
<211> LENGTH: 20
<212> TYPE: PRT
<213> ORGANISM: Artificial Sequence
<220> FEATURE:
<223> OTHER INFORMATION: EBV gp350

<400> SEQUENCE: 147

Asn Ile Val Phe Ser Asp Glu Ile Pro Ala Ser Gln Asp Met Pro Thr
1               5                   10                  15

Asn Thr Thr Asp
            20

<210> SEQ ID NO 148
<211> LENGTH: 20
<212> TYPE: PRT
<213> ORGANISM: Artificial Sequence
<220> FEATURE:
<223> OTHER INFORMATION: EBV gp350

<400> SEQUENCE: 148

Ile Thr Tyr Val Gly Asp Asn Ala Thr Tyr Ser Val Pro Met Val Thr
1               5                   10                  15

Ser Glu Asp Ala
            20

<210> SEQ ID NO 149
<211> LENGTH: 20
<212> TYPE: PRT
<213> ORGANISM: Artificial Sequence
<220> FEATURE:
<223> OTHER INFORMATION: EBV gp350

<400> SEQUENCE: 149

Asn Ser Pro Asn Val Thr Val Thr Ala Phe Trp Ala Trp Pro Asn Asn
1               5                   10                  15

Thr Glu Thr Asp
            20

<210> SEQ ID NO 150
<211> LENGTH: 20
<212> TYPE: PRT
<213> ORGANISM: Artificial Sequence
<220> FEATURE:
<223> OTHER INFORMATION: EBV gp350

<400> SEQUENCE: 150

Phe Lys Cys Lys Trp Thr Leu Thr Ser Gly Thr Pro Ser Gly Cys Glu
1               5                   10                  15

Asn Ile Ser Gly
            20

<210> SEQ ID NO 151
<211> LENGTH: 20
<212> TYPE: PRT
<213> ORGANISM: Artificial Sequence
<220> FEATURE:
<223> OTHER INFORMATION: EBV gp350

<400> SEQUENCE: 151
```

```
Ala Phe Ala Ser Asn Arg Thr Phe Asp Ile Thr Val Ser Gly Leu Gly
1               5                   10                  15

Thr Ala Pro Lys
            20
```

<210> SEQ ID NO 152
<211> LENGTH: 20
<212> TYPE: PRT
<213> ORGANISM: Artificial Sequence
<220> FEATURE:
<223> OTHER INFORMATION: EBV gp350

<400> SEQUENCE: 152

```
Thr Leu Ile Ile Thr Arg Thr Ala Thr Asn Ala Thr Thr Thr Thr His
1               5                   10                  15

Lys Val Ile Phe
            20
```

<210> SEQ ID NO 153
<211> LENGTH: 20
<212> TYPE: PRT
<213> ORGANISM: Artificial Sequence
<220> FEATURE:
<223> OTHER INFORMATION: EBV gp350

<400> SEQUENCE: 153

```
Ser Lys Ala Pro Glu Ser Thr Thr Thr Ser Pro Thr Leu Asn Thr Thr
1               5                   10                  15

Gly Phe Ala Asp
            20
```

<210> SEQ ID NO 154
<211> LENGTH: 20
<212> TYPE: PRT
<213> ORGANISM: Artificial Sequence
<220> FEATURE:
<223> OTHER INFORMATION: EBV gp350

<400> SEQUENCE: 154

```
Pro Asn Thr Thr Thr Gly Leu Pro Ser Ser Thr His Val Pro Thr Asn
1               5                   10                  15

Leu Thr Ala Pro
            20
```

<210> SEQ ID NO 155
<211> LENGTH: 20
<212> TYPE: PRT
<213> ORGANISM: Artificial Sequence
<220> FEATURE:
<223> OTHER INFORMATION: EBV gp350

<400> SEQUENCE: 155

```
Ala Ser Thr Gly Pro Thr Val Ser Thr Ala Asp Val Thr Ser Pro Thr
1               5                   10                  15

Pro Ala Gly Thr
            20
```

<210> SEQ ID NO 156
<211> LENGTH: 20
<212> TYPE: PRT
<213> ORGANISM: Artificial Sequence
<220> FEATURE:
<223> OTHER INFORMATION: EBV gp350

<400> SEQUENCE: 156

Thr Ser Gly Ala Ser Pro Val Thr Pro Ser Pro Ser Pro Trp Asp Asn
1               5                   10                  15

Gly Thr Glu Ser
            20

<210> SEQ ID NO 157
<211> LENGTH: 20
<212> TYPE: PRT
<213> ORGANISM: Artificial Sequence
<220> FEATURE:
<223> OTHER INFORMATION: EBV gp350

<400> SEQUENCE: 157

Lys Ala Pro Asp Met Thr Ser Ser Ser Pro Val Thr Thr Pro Thr
1               5                   10                  15

Pro Asn Ala Thr
            20

<210> SEQ ID NO 158
<211> LENGTH: 20
<212> TYPE: PRT
<213> ORGANISM: Artificial Sequence
<220> FEATURE:
<223> OTHER INFORMATION: EBV gp350

<400> SEQUENCE: 158

Ser Pro Thr Pro Ala Val Thr Thr Pro Thr Pro Asn Ala Thr Ser Pro
1               5                   10                  15

Thr Pro Ala Val
            20

<210> SEQ ID NO 159
<211> LENGTH: 20
<212> TYPE: PRT
<213> ORGANISM: Artificial Sequence
<220> FEATURE:
<223> OTHER INFORMATION: EBV gp350

<400> SEQUENCE: 159

Thr Thr Pro Thr Pro Asn Ala Thr Ser Pro Thr Leu Gly Lys Thr Ser
1               5                   10                  15

Pro Thr Ser Ala
            20

<210> SEQ ID NO 160
<211> LENGTH: 20
<212> TYPE: PRT
<213> ORGANISM: Artificial Sequence
<220> FEATURE:
<223> OTHER INFORMATION: EBV gp350

<400> SEQUENCE: 160

Val Thr Thr Pro Thr Pro Asn Ala Thr Ser Pro Thr Leu Gly Lys Thr
1               5                   10                  15

Ser Pro Thr Ser
            20

<210> SEQ ID NO 161
<211> LENGTH: 20
<212> TYPE: PRT
<213> ORGANISM: Artificial Sequence
<220> FEATURE:
<223> OTHER INFORMATION: EBV gp350

```
<400> SEQUENCE: 161

Ala Val Thr Thr Pro Thr Pro Asn Ala Thr Ser Pro Thr Leu Gly Lys
1               5                   10                  15

Thr Ser Pro Thr
            20

<210> SEQ ID NO 162
<211> LENGTH: 20
<212> TYPE: PRT
<213> ORGANISM: Artificial Sequence
<220> FEATURE:
<223> OTHER INFORMATION: EBV gp350

<400> SEQUENCE: 162

Ser Ala Val Thr Thr Pro Thr Pro Asn Ala Thr Gly Pro Thr Val Gly
1               5                   10                  15

Glu Thr Ser Pro
            20

<210> SEQ ID NO 163
<211> LENGTH: 20
<212> TYPE: PRT
<213> ORGANISM: Artificial Sequence
<220> FEATURE:
<223> OTHER INFORMATION: EBV gp350

<400> SEQUENCE: 163

Gln Ala Asn Ala Thr Asn His Thr Leu Gly Gly Thr Ser Pro Thr Pro
1               5                   10                  15

Val Val Thr Ser
            20

<210> SEQ ID NO 164
<211> LENGTH: 20
<212> TYPE: PRT
<213> ORGANISM: Artificial Sequence
<220> FEATURE:
<223> OTHER INFORMATION: EBV gp350

<400> SEQUENCE: 164

Gln Pro Lys Asn Ala Thr Ser Ala Val Thr Thr Gly Gln His Asn Ile
1               5                   10                  15

Thr Ser Ser Ser
            20

<210> SEQ ID NO 165
<211> LENGTH: 20
<212> TYPE: PRT
<213> ORGANISM: Artificial Sequence
<220> FEATURE:
<223> OTHER INFORMATION: EBV gp350

<400> SEQUENCE: 165

Thr Ser Ser Met Ser Leu Arg Pro Ser Ser Asn Pro Glu Thr Leu Ser
1               5                   10                  15

Pro Ser Thr Ser
            20

<210> SEQ ID NO 166
<211> LENGTH: 20
<212> TYPE: PRT
<213> ORGANISM: Artificial Sequence
<220> FEATURE:
<223> OTHER INFORMATION: EBV gp350
```

-continued

```
<400> SEQUENCE: 166

Asp Asn Ser Thr Ser His Met Pro Leu Leu Thr Ser Ala His Pro Thr
1               5                   10                  15

Gly Gly Glu Asn
            20

<210> SEQ ID NO 167
<211> LENGTH: 20
<212> TYPE: PRT
<213> ORGANISM: Artificial Sequence
<220> FEATURE:
<223> OTHER INFORMATION: EBV gp350

<400> SEQUENCE: 167

Ile Thr Gln Val Thr Pro Ala Ser Ile Ser Thr His His Val Ser Thr
1               5                   10                  15

Ser Ser Pro Ala
            20

<210> SEQ ID NO 168
<211> LENGTH: 20
<212> TYPE: PRT
<213> ORGANISM: Artificial Sequence
<220> FEATURE:
<223> OTHER INFORMATION: EBV gp350

<400> SEQUENCE: 168

Pro Arg Pro Gly Thr Thr Ser Gln Ala Ser Gly Pro Gly Asn Ser Ser
1               5                   10                  15

Thr Ser Thr Lys
            20

<210> SEQ ID NO 169
<211> LENGTH: 20
<212> TYPE: PRT
<213> ORGANISM: Artificial Sequence
<220> FEATURE:
<223> OTHER INFORMATION: EBV gp350

<400> SEQUENCE: 169

Pro Gly Glu Val Asn Val Thr Lys Gly Thr Pro Pro Gln Asn Ala Thr
1               5                   10                  15

Ser Pro Gln Ala
            20

<210> SEQ ID NO 170
<211> LENGTH: 20
<212> TYPE: PRT
<213> ORGANISM: Artificial Sequence
<220> FEATURE:
<223> OTHER INFORMATION: EBV gp350

<400> SEQUENCE: 170

Pro Ser Gly Gln Lys Thr Ala Val Pro Thr Val Thr Ser Thr Gly Gly
1               5                   10                  15

Lys Ala Asn Ser
            20

<210> SEQ ID NO 171
<211> LENGTH: 20
<212> TYPE: PRT
<213> ORGANISM: Artificial Sequence
<220> FEATURE:
```

-continued

```
<223> OTHER INFORMATION: EBV gp350

<400> SEQUENCE: 171

Thr Thr Gly Gly Lys His Thr Thr Gly His Gly Ala Arg Thr Ser Thr
1               5                   10                  15

Glu Pro Thr Thr
            20

<210> SEQ ID NO 172
<211> LENGTH: 20
<212> TYPE: PRT
<213> ORGANISM: Artificial Sequence
<220> FEATURE:
<223> OTHER INFORMATION: EBV gp350

<400> SEQUENCE: 172

Asp Tyr Gly Gly Asp Ser Thr Thr Pro Arg Pro Arg Tyr Asn Ala Thr
1               5                   10                  15

Thr Tyr Leu Pro
            20

<210> SEQ ID NO 173
<211> LENGTH: 20
<212> TYPE: PRT
<213> ORGANISM: Artificial Sequence
<220> FEATURE:
<223> OTHER INFORMATION: EBV gp350

<400> SEQUENCE: 173

Pro Ser Thr Ser Ser Lys Leu Arg Pro Arg Trp Thr Phe Thr Ser Pro
1               5                   10                  15

Pro Val Thr Thr
            20

<210> SEQ ID NO 174
<211> LENGTH: 20
<212> TYPE: PRT
<213> ORGANISM: Artificial Sequence
<220> FEATURE:
<223> OTHER INFORMATION: EBV gp350

<400> SEQUENCE: 174

Ala Gln Ala Thr Val Pro Val Pro Pro Thr Ser Gln Pro Arg Phe Ser
1               5                   10                  15

Asn Leu Ser Met
            20

<210> SEQ ID NO 175
<211> LENGTH: 20
<212> TYPE: PRT
<213> ORGANISM: Artificial Sequence
<220> FEATURE:
<223> OTHER INFORMATION: EBV gp350

<400> SEQUENCE: 175

Leu Val Leu Gln Trp Ala Ser Leu Ala Val Leu Thr Leu Leu Leu Leu
1               5                   10                  15

Leu Val Met Ala
            20

<210> SEQ ID NO 176
<211> LENGTH: 20
<212> TYPE: PRT
<213> ORGANISM: Artificial Sequence
```

-continued

```
<220> FEATURE:
<223> OTHER INFORMATION: EBV gp350

<400> SEQUENCE: 176

Asp Cys Ala Phe Arg Arg Asn Leu Ser Thr Ser His Thr Tyr Thr Thr
1               5                   10                  15

Pro Pro Tyr Asp
            20

<210> SEQ ID NO 177
<211> LENGTH: 20
<212> TYPE: PRT
<213> ORGANISM: Artificial Sequence
<220> FEATURE:
<223> OTHER INFORMATION: EBV gp350

<400> SEQUENCE: 177

Asn Leu Ser Thr Ser His Thr Tyr Thr Thr Pro Pro Tyr Asp Asp Ala
1               5                   10                  15

Glu Thr Tyr Val
            20

<210> SEQ ID NO 178
<211> LENGTH: 138
<212> TYPE: PRT
<213> ORGANISM: Artificial Sequence
<220> FEATURE:
<223> OTHER INFORMATION: heavy chain VH m72A1

<400> SEQUENCE: 178

Met Gly Trp Arg Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Thr Ser Met Lys Ile Ser Cys Lys Ala Ser Gly Ser Ser Phe
        35                  40                  45

Thr Asp Tyr Thr Met Asn Trp Met Lys Gln Ser His Gly Lys Asn Leu
    50                  55                  60

Glu Trp Ile Gly Leu Ile Asn Pro Tyr Asn Gly Gly Thr Arg Tyr Asn
65                  70                  75                  80

Gln Lys Phe Lys Gly Lys Ala Thr Leu Thr Leu Asp Lys Ser Ser Ser
                85                  90                  95

Thr Ala Tyr Met Glu Val Leu Ser Leu Thr Ser Glu Asp Ser Ala Val
            100                 105                 110

Tyr Tyr Cys Ala Gly Gly Leu Arg Arg Val Asn Trp Phe Ala Tyr Trp
        115                 120                 125

Gly Gln Gly Thr Leu Val Ser Val Ser Ala
    130                 135

<210> SEQ ID NO 179
<211> LENGTH: 119
<212> TYPE: PRT
<213> ORGANISM: Artificial Sequence
<220> FEATURE:
<223> OTHER INFORMATION: heavy chain VH h72A1

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ser Phe Thr Asp Tyr
            20                  25                  30
```

```
Thr Met Asn Trp Met Arg Gln Ser Pro Gly Lys Gly Leu Glu Trp Ile
            35                  40                  45

Gly Leu Ile Asn Pro Tyr Asn Gly Gly Thr Arg Tyr Ala Asp Ser Val
         50                  55                  60

Lys Gly Arg Ala Thr Leu Ser Leu Asp Lys Ser Lys Asn Thr Ala Tyr
 65                  70                  75                  80

Leu Gln Met Asn Ser Leu Arg Ala Glu Asp Thr Ala Ile Tyr Tyr Cys
                 85                  90                  95

Ala Gly Gly Leu Arg Arg Val Asn Trp Phe Ala Tyr Trp Gly Gln Gly
                100                 105                 110

Thr Leu Val Thr Val Ser Ser
            115
```

<210> SEQ ID NO 180
<211> LENGTH: 128
<212> TYPE: PRT
<213> ORGANISM: Artificial Sequence
<220> FEATURE:
<223> OTHER INFORMATION: light chain VL m72A1

<400> SEQUENCE: 180

```
Met Ala Trp Ile Ser Leu Ile Leu Ser Leu Leu Ala Leu Ser Ser Gly
 1               5                  10                  15

Ala Ile Ser Gln Ala Val Leu Thr Gln Glu Ser Ala Leu Thr Thr Ser
             20                  25                  30

Pro Gly Glu Thr Val Thr Leu Thr Cys Arg Ser Ser Thr Gly Ala Val
         35                  40                  45

Thr Thr Ser Asn Tyr Ala Asn Trp Val Gln Glu Lys Pro Asp His Leu
 50                  55                  60

Phe Thr Gly Leu Ile Gly Gly Thr Asn Asn Arg Val Pro Gly Val Pro
 65                  70                  75                  80

Ala Arg Phe Ser Gly Ser Leu Ile Gly Asp Lys Ala Ala Leu Thr Ile
                 85                  90                  95

Thr Gly Ala Gln Thr Glu Asp Glu Ala Ile Tyr Phe Cys Val Leu Trp
                100                 105                 110

His Ser Asn His Trp Val Phe Gly Gly Gly Thr Lys Leu Thr Val Leu
            115                 120                 125
```

<210> SEQ ID NO 181
<211> LENGTH: 111
<212> TYPE: PRT
<213> ORGANISM: Artificial Sequence
<220> FEATURE:
<223> OTHER INFORMATION: light chain VL h72A1

<400> SEQUENCE: 181

```
Asp Ala Gln Leu Thr Gln Ser Pro Ile Leu Leu Ser Ala Ser Val Gly
 1               5                  10                  15

Asp Arg Val Thr Ile Thr Cys Arg Ser Ser Thr Gly Ala Val Thr Thr
             20                  25                  30

Ser Asn Tyr Ala Asn Trp Val Gln Glu Arg Thr Asn Gly Ser Phe Arg
             35                  40                  45

Gly Leu Ile Gly Gly Thr Asn Asn Arg Val Pro Gly Val Pro Ser Arg
         50                  55                  60

Phe Ser Gly Ser Leu Ser Gly Asp Asp Ala Thr Leu Thr Ile Ser Ser
 65                  70                  75                  80

Leu Gln Pro Glu Asp Glu Ala Asp Tyr Phe Cys Val Leu Trp His Ser
```

85                  90                  95
Asn His Trp Val Phe Gly Ala Gly Thr Lys Val Glu Ile Lys Arg
            100                 105                 110

<210> SEQ ID NO 182
<211> LENGTH: 921
<212> TYPE: PRT
<213> ORGANISM: Artificial Sequence
<220> FEATURE:
<223> OTHER INFORMATION: EBV gp350 protein

<400> SEQUENCE: 182

Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
            115                 120                 125

Asp Val Tyr Phe Gln Asp Val Phe Gly Thr Met Trp Cys His His Ala
        130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp

```
                340                 345                 350
Ala Trp Pro Asn Asn Thr Glu Thr Asp Phe Lys Cys Lys Trp Thr Leu
            355                 360                 365

Thr Ser Gly Thr Pro Ser Gly Cys Glu Asn Ile Ser Gly Ala Phe Ala
        370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Asp Pro Asn Thr Thr Thr Gly Leu
            435                 440                 445

Pro Ser Ser Thr His Val Pro Thr Asn Leu Thr Ala Pro Ala Ser Thr
        450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
                485                 490                 495

Asn Gly Thr Glu Ser Lys Ala Pro Asp Met Thr Ser Ser Thr Ser Pro
                500                 505                 510

Val Thr Thr Pro Thr Pro Asn Ala Thr Ser Pro Thr Pro Ala Val Thr
            515                 520                 525

Thr Pro Thr Pro Asn Ala Thr Ser Pro Thr Pro Ala Val Thr Thr Pro
        530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
                565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
        595                 600                 605

Pro Asn Ala Thr Gly Pro Thr Val Gly Glu Thr Ser Pro Gln Ala Asn
    610                 615                 620

Ala Thr Asn His Thr Leu Gly Gly Thr Ser Pro Thr Pro Val Val Thr
625                 630                 635                 640

Ser Gln Pro Lys Asn Ala Thr Ser Ala Val Thr Thr Gly Gln His Asn
                645                 650                 655

Ile Thr Ser Ser Ser Thr Ser Ser Met Ser Leu Arg Pro Ser Ser Asn
            660                 665                 670

Pro Glu Thr Leu Ser Pro Ser Thr Ser Asp Asn Ser Thr Ser His Met
        675                 680                 685

Pro Leu Leu Thr Ser Ala His Pro Thr Gly Gly Glu Asn Ile Thr Gln
    690                 695                 700

Val Thr Pro Ala Ser Ile Ser Thr His His Val Ser Thr Ser Ser Pro
705                 710                 715                 720

Ala Pro Arg Pro Gly Thr Thr Ser Gln Ala Ser Gly Pro Gly Asn Ser
                725                 730                 735

Ser Thr Ser Thr Lys Pro Gly Glu Val Asn Val Thr Lys Gly Thr Pro
            740                 745                 750

Pro Gln Asn Ala Thr Ser Pro Gln Ala Pro Ser Gly Gln Lys Thr Ala
        755                 760                 765
```

```
Val Pro Thr Val Thr Ser Thr Gly Gly Lys Ala Asn Ser Thr Thr Gly
    770                 775                 780
Gly Lys His Thr Thr Gly His Gly Ala Arg Thr Ser Thr Glu Pro Thr
785                 790                 795                 800
Thr Asp Tyr Gly Gly Asp Ser Thr Thr Pro Arg Pro Arg Tyr Asn Ala
                805                 810                 815
Thr Thr Tyr Leu Pro Pro Ser Thr Ser Ser Lys Leu Arg Pro Arg Trp
                820                 825                 830
Thr Phe Thr Ser Pro Pro Val Thr Thr Ala Gln Ala Thr Val Pro Val
                835                 840                 845
Pro Pro Thr Ser Gln Pro Arg Phe Ser Asn Leu Ser Met Leu Val Leu
                850                 855                 860
Gln Trp Ala Ser Leu Ala Val Leu Thr Leu Leu Leu Leu Val Met
865                 870                 875                 880
Ala Asp Cys Ala Phe Arg Arg Asn Leu Ser Thr Ser His Thr Tyr Thr
                885                 890                 895
Thr Pro Pro Tyr Asp Asn Leu Ser Thr Ser His Thr Tyr Thr Thr Pro
                900                 905                 910
Pro Tyr Asp Asp Ala Glu Thr Tyr Val
                915                 920

<210> SEQ ID NO 183
<211> LENGTH: 154
<212> TYPE: PRT
<213> ORGANISM: Artificial Sequence
<220> FEATURE:
<223> OTHER INFORMATION: heavy chain mE1D1

<400> SEQUENCE: 183

Leu Pro Glu Phe Glu Val Lys Leu Gln Glu Ser Gly Pro Glu Leu Val
1               5                   10                  15
Lys Pro Gly Ala Ser Val Lys Met Ser Cys Lys Ala Ser Gly Tyr Thr
                20                  25                  30
Phe Thr Asp Tyr Val Ile Ser Trp Val Lys Gln Arg Thr Gly Gln Gly
                35                  40                  45
Leu Glu Trp Ile Gly Glu Ile Tyr Pro Glu Ser Gly Asn Thr Tyr Tyr
    50                  55                  60
Asn Glu Lys Phe Lys Gly Glu Ala Thr Leu Thr Ala Asp Lys Ser Ser
65                  70                  75                  80
Asn Thr Ala Tyr Met Gln Leu Ser Arg Leu Thr Ser Glu Asp Ser Ala
                85                  90                  95
Val Tyr Phe Cys Ala Glu Gly Tyr Ala Met Asp Phe Trp Gly Gln Gly
                100                 105                 110
Thr Ser Val Thr Val Ser Ser Ala Lys Thr Thr Pro Pro Ser Val Tyr
                115                 120                 125
Pro Leu Ala Pro Gly Ser Ala Ala Gln Thr Asn Ser Met Val Thr Leu
                130                 135                 140
Gly Cys Leu Val Lys Gly Tyr Phe Pro Glu
145                 150

<210> SEQ ID NO 184
<211> LENGTH: 115
<212> TYPE: PRT
<213> ORGANISM: Artificial Sequence
<220> FEATURE:
<223> OTHER INFORMATION: heavy chain hE1D1
```

<400> SEQUENCE: 184

Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Asp Tyr
            20                  25                  30

Val Ile Ser Trp Val Arg Gln Ser Pro Gly Lys Gly Leu Glu Trp Ile
        35                  40                  45

Gly Glu Ile Tyr Pro Glu Ser Gly Asn Thr Tyr Tyr Ala Asp Ser Val
    50                  55                  60

Lys Gly Arg Ala Thr Leu Ser Ala Asp Lys Ser Lys Asn Thr Ala Tyr
65                  70                  75                  80

Leu Gln Met Asn Ser Leu Arg Ala Glu Asp Thr Ala Ile Tyr Phe Cys
                85                  90                  95

Ala Glu Gly Tyr Ala Met Asp Phe Trp Gly Gln Gly Thr Leu Val Thr
            100                 105                 110

Val Ser Ser
        115

<210> SEQ ID NO 185
<211> LENGTH: 130
<212> TYPE: PRT
<213> ORGANISM: Artificial Sequence
<220> FEATURE:
<223> OTHER INFORMATION: light chain mE1D1

<400> SEQUENCE: 185

Asp Ile Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Met Ile
65                  70                  75                  80

Asn Arg Val Glu Ala Glu Asp Leu Gly Val Tyr Phe Cys Ser Gln Ser
                85                  90                  95

Ile His Val Pro Arg Thr Phe Gly Gly Gly Thr Lys Leu Glu Ile Lys
            100                 105                 110

Arg Ala Asp Ala Ala Pro Thr Val Ser Ile Phe Pro Pro Ser Ser Lys
        115                 120                 125

Leu Gly
    130

<210> SEQ ID NO 186
<211> LENGTH: 113
<212> TYPE: PRT
<213> ORGANISM: Artificial Sequence
<220> FEATURE:
<223> OTHER INFORMATION: light chain hE1D1

<400> SEQUENCE: 186

Asp Ile Gln Met Thr Gln Ser Pro Ile Leu Leu Ser Ala Ser Val Gly
1               5                   10                  15

Asp Arg Val Thr Ile Thr Cys Arg Ser Ser Gln Ser Leu Leu His Ser
            20                  25                  30

-continued

```
Asn Gly Asn Thr Tyr Leu His Trp Tyr Gln Gln Arg Thr Asn Gly Ser
            35                  40                  45

Pro Arg Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Glu Ala Asp Tyr Phe Cys Ser Gln Ser
                85                  90                  95

Ile His Val Pro Arg Thr Phe Gly Ala Gly Thr Lys Val Glu Ile Lys
                100                 105                 110

Arg
```